(12) United States Patent
Sabir et al.

(10) Patent No.: US 11,241,330 B1
(45) Date of Patent: Feb. 8, 2022

(54) APPARATUS FOR CREATION OF INJECTABLE SLURRY

(71) Applicant: Brixton Biosciences, Inc., Cambridge, MA (US)

(72) Inventors: Sameer Sabir, Arlington, MA (US); Olivier Kagan, Belmont, MA (US); Charles Sidoti, Boston, MA (US)

(73) Assignee: Brixton Biosciences, Inc., Cambridge, MA (US)

( * ) Notice: Subject to any disclaimer, the term of this patent is extended or adjusted under 35 U.S.C. 154(b) by 0 days.

(21) Appl. No.: 17/221,357

(22) Filed: Apr. 2, 2021

(51) Int. Cl.
| *A61F 7/00* | (2006.01) |
| *B02C 18/10* | (2006.01) |
| *B01F 7/00* | (2006.01) |
| *A61B 18/02* | (2006.01) |
| *B01F 13/00* | (2006.01) |

(52) U.S. Cl.
CPC .............. *A61F 7/0085* (2013.01); *B01F 7/00* (2013.01); *B01F 13/0023* (2013.01); *B02C 18/10* (2013.01); *A61B 2018/0293* (2013.01); *A61M 2205/3606* (2013.01)

(58) Field of Classification Search
CPC combination set(s) only.
See application file for complete search history.

(56) References Cited

U.S. PATENT DOCUMENTS

| 3,570,486 | A | 3/1971 | Engelsher et al. |
| 3,724,077 | A | 4/1973 | Preston et al. |
| 4,018,222 | A | 4/1977 | McAleer et al. |
| 4,036,225 | A | 7/1977 | Maury et al. |
| 4,799,358 | A | 1/1989 | Knopf et al. |
| 4,986,079 | A | 1/1991 | Koseki et al. |
| 5,005,364 | A | 4/1991 | Nelson |
| 5,143,063 | A | 9/1992 | Fellner |
| 5,507,790 | A | 4/1996 | Weiss |
| 5,769,879 | A | 6/1998 | Richards et al. |
| 5,971,953 | A | 10/1999 | Bachynsky |
| 6,033,377 | A | 3/2000 | Rasmussen et al. |

(Continued)

FOREIGN PATENT DOCUMENTS

| CN | 203989291 U | 12/2014 |
| DE | 3125345 A1 | 1/1983 |

(Continued)

OTHER PUBLICATIONS

Anchordoquy, T. J. and Koe, G. S., "Physical stability of nonviral plasmid-based therapeutics." Journal of Pharmaceutical Sciences, vol. 89, No. 3, pp. 289-296 (2000) (8 pages).

(Continued)

*Primary Examiner* — Joseph A Stoklosa
*Assistant Examiner* — Adam J Avigan
(74) *Attorney, Agent, or Firm* — Wilmer Cutler Pickering Hale and Dorr LLP

(57) ABSTRACT

Disclosed herein is a system for creating an injectable and flowable cold slurry, the system comprising a housing; a mount operatively connected to the housing configured to accept a container; a first motor configured to move the mount from a first position to a second position; a second motor; and a drive shaft in communication with the second motor, wherein the drive shaft is configured to rotate to cause an internal volume of the container to be transformed into the injectable and flowable cold slurry.

26 Claims, 36 Drawing Sheets

(56) References Cited

U.S. PATENT DOCUMENTS

| | | | |
|---|---|---|---|
| 6,062,722 A | 5/2000 | Lake | |
| 6,244,052 B1 | 6/2001 | Kasza | |
| 6,430,957 B1 | 8/2002 | Inada et al. | |
| 6,488,651 B1 | 12/2002 | Morris et al. | |
| 6,550,957 B2 | 4/2003 | Mizutani et al. | |
| 6,595,388 B2 | 7/2003 | Mizutani et al. | |
| 6,698,213 B2 | 3/2004 | Voute et al. | |
| 6,706,020 B1 | 3/2004 | Urich | |
| 6,880,384 B2 | 4/2005 | Hvidtfeldt et al. | |
| 6,962,601 B2 | 11/2005 | Becker et al. | |
| 6,966,894 B1 | 11/2005 | Urich | |
| 6,996,995 B2 | 2/2006 | Voute et al. | |
| 7,029,163 B2 | 4/2006 | Barker et al. | |
| 7,351,221 B2 | 4/2008 | Trombley, III et al. | |
| 7,353,658 B2 | 4/2008 | Voute et al. | |
| 7,367,341 B2 | 5/2008 | Anderson et al. | |
| 7,407,631 B2 | 8/2008 | Swon et al. | |
| 7,422,601 B2 | 9/2008 | Becker et al. | |
| 7,507,234 B2 | 3/2009 | Utley et al. | |
| 7,634,917 B2 | 12/2009 | Fuhr et al. | |
| 7,727,183 B2 | 6/2010 | Sharon et al. | |
| 7,727,219 B2 | 6/2010 | Lampeter | |
| 7,771,390 B2 | 8/2010 | Brown | |
| 7,897,141 B2 | 3/2011 | Wheatley et al. | |
| 7,951,108 B2 | 5/2011 | Harper et al. | |
| 7,963,937 B2 | 6/2011 | Pauser et al. | |
| 8,021,037 B2 | 9/2011 | Krueger et al. | |
| 8,037,696 B2 | 10/2011 | Shaham et al. | |
| 8,123,084 B2 | 2/2012 | Reynolds et al. | |
| 8,177,123 B2 | 5/2012 | Voute et al. | |
| 8,365,958 B2 | 2/2013 | Ho et al. | |
| 8,448,457 B2 | 5/2013 | Cutting et al. | |
| 8,505,315 B2 | 8/2013 | Kasza et al. | |
| 8,651,731 B2 | 2/2014 | Wintergerste et al. | |
| 8,672,879 B2 | 3/2014 | Grant et al. | |
| 8,697,430 B2 | 4/2014 | Toguchida et al. | |
| 8,715,622 B2 | 5/2014 | Wheatley et al. | |
| 8,840,608 B2 | 9/2014 | Anderson et al. | |
| 8,863,532 B2 | 10/2014 | Voute et al. | |
| 8,931,665 B2 | 1/2015 | Gold | |
| 8,992,469 B2 | 3/2015 | Bartlett, II et al. | |
| 9,046,292 B2 | 6/2015 | Burke et al. | |
| 9,163,208 B2 | 10/2015 | Runyon | |
| 9,295,530 B2 | 3/2016 | Walter et al. | |
| 9,339,840 B2 | 5/2016 | Kane et al. | |
| 9,498,309 B2 | 11/2016 | Boehm et al. | |
| 9,522,097 B2 | 12/2016 | Tennican | |
| 9,616,176 B2 | 4/2017 | Just | |
| 9,642,002 B2 | 5/2017 | Nehushtan | |
| 9,821,118 B2 | 11/2017 | Adlon et al. | |
| 9,855,536 B2 | 1/2018 | Nguyen et al. | |
| 9,873,098 B2 | 1/2018 | Asada et al. | |
| 9,895,494 B2 | 2/2018 | Fisher et al. | |
| 9,980,076 B1 | 5/2018 | Pratt et al. | |
| 9,980,763 B2 | 5/2018 | Foster et al. | |
| 10,143,982 B2 | 12/2018 | Gettings et al. | |
| 10,183,117 B2 | 1/2019 | Fraunhofer et al. | |
| 10,208,280 B2 | 2/2019 | Joaquim Rodrigues et al. | |
| 10,215,673 B2 | 2/2019 | Schryver et al. | |
| 10,220,148 B2 | 3/2019 | Johannesson et al. | |
| 10,278,895 B2 | 5/2019 | Chou et al. | |
| 10,363,278 B2 | 7/2019 | Beaudry et al. | |
| 10,456,526 B2 | 10/2019 | Wang et al. | |
| 10,478,242 B2 | 11/2019 | Hawkins et al. | |
| 2002/0021741 A1 | 2/2002 | Faries et al. | |
| 2002/0107199 A1 | 8/2002 | Walker | |
| 2002/0166786 A1 | 11/2002 | Asculai et al. | |
| 2003/0032996 A1 | 2/2003 | Hallman | |
| 2003/0151202 A1* | 8/2003 | Fisher | A63F 9/30 273/447 |
| 2003/0181897 A1 | 9/2003 | Thomas et al. | |
| 2004/0176755 A1 | 9/2004 | Lafontaine | |
| 2004/0236273 A1 | 11/2004 | Tanaka et al. | |
| 2005/0203598 A1 | 9/2005 | Becker et al. | |
| 2005/0251120 A1 | 11/2005 | Anderson et al. | |
| 2006/0079869 A1 | 4/2006 | Bischof et al. | |
| 2006/0161232 A1 | 7/2006 | Kasza et al. | |
| 2006/0235375 A1 | 10/2006 | Littrup et al. | |
| 2007/0010861 A1 | 1/2007 | Anderson et al. | |
| 2007/0032774 A1 | 2/2007 | Glade et al. | |
| 2007/0056313 A1 | 3/2007 | Kasza et al. | |
| 2007/0106247 A1 | 5/2007 | Burnett et al. | |
| 2008/0176326 A1 | 7/2008 | Yaghmour | |
| 2008/0236186 A1 | 10/2008 | Kasza et al. | |
| 2008/0247957 A1 | 10/2008 | Wheatley | |
| 2008/0279783 A1 | 11/2008 | Wheatley et al. | |
| 2009/0028797 A1 | 1/2009 | Wheatley et al. | |
| 2009/0118722 A1 | 5/2009 | Ebbers et al. | |
| 2009/0209031 A1 | 8/2009 | Stope | |
| 2009/0234325 A1 | 9/2009 | Rozenberg et al. | |
| 2009/0255276 A1 | 10/2009 | Kasza et al. | |
| 2009/0301107 A1 | 12/2009 | Kammer et al. | |
| 2010/0097879 A1 | 4/2010 | Krueger et al. | |
| 2010/0113615 A1 | 5/2010 | Boyden et al. | |
| 2010/0137304 A1 | 6/2010 | Gilday et al. | |
| 2010/0152880 A1 | 6/2010 | Boyden et al. | |
| 2011/0207215 A1 | 8/2011 | Itchoda et al. | |
| 2012/0071884 A1 | 3/2012 | Cooper et al. | |
| 2012/0295214 A1 | 11/2012 | Wang et al. | |
| 2012/0323232 A1 | 12/2012 | Wolf et al. | |
| 2013/0011332 A1 | 1/2013 | Boyden et al. | |
| 2013/0091890 A1 | 4/2013 | Schryver et al. | |
| 2013/0184695 A1 | 7/2013 | Fourkas et al. | |
| 2013/0190744 A1 | 7/2013 | Avram et al. | |
| 2013/0344221 A1* | 12/2013 | Farrell | B01F 7/00 426/590 |
| 2014/0200511 A1 | 7/2014 | Boyden et al. | |
| 2014/0303697 A1 | 10/2014 | Anderson et al. | |
| 2014/0335614 A1 | 11/2014 | Schryver | |
| 2016/0016134 A1 | 1/2016 | Smith et al. | |
| 2016/0151200 A1 | 6/2016 | Kammer et al. | |
| 2016/0279341 A1 | 9/2016 | Anderson et al. | |
| 2016/0338346 A1 | 11/2016 | Pensak | |
| 2017/0135337 A1 | 5/2017 | Brown et al. | |
| 2017/0156714 A1 | 6/2017 | Pilpel et al. | |
| 2017/0257908 A1 | 9/2017 | Schryver et al. | |
| 2017/0274011 A1 | 9/2017 | Garibyan et al. | |
| 2017/0274078 A1 | 9/2017 | Garibyan et al. | |
| 2018/0064100 A1 | 3/2018 | Morris et al. | |
| 2018/0116868 A1* | 5/2018 | Velis | B01F 13/0023 |
| 2018/0140514 A1 | 5/2018 | Velis et al. | |
| 2018/0177180 A1 | 6/2018 | Chapman et al. | |
| 2018/0250056 A1 | 9/2018 | Avram et al. | |
| 2018/0289537 A1 | 10/2018 | Velis | |
| 2019/0053939 A1* | 2/2019 | Garibyan | A61F 7/0085 |
| 2019/0183558 A1 | 6/2019 | Anderson et al. | |
| 2019/0191693 A1 | 6/2019 | Johnson et al. | |
| 2019/0192424 A1 | 6/2019 | Garibyan et al. | |
| 2019/0320650 A1 | 10/2019 | Johnson et al. | |

FOREIGN PATENT DOCUMENTS

| | | |
|---|---|---|
| DE | 3934024 A1 | 4/1991 |
| DE | 19840540 A1 | 3/2000 |
| DE | 19840542 A1 | 3/2000 |
| EP | 1106065 A2 | 6/2001 |
| JP | 2003534366 A | 11/2003 |
| JP | 2009115056 A | 5/2009 |
| JP | 2010174817 A | 8/2010 |
| KR | 10-2016-0106877 A | 9/2016 |
| WO | WO-93/0930 A1 | 1/1993 |
| WO | WO-98/01174 A1 | 1/1998 |
| WO | WO-2001/91720 A2 | 12/2001 |
| WO | WO-03/095000 A1 | 11/2003 |
| WO | WO-08/55243 A2 | 5/2008 |
| WO | WO-09/09540 A1 | 1/2009 |
| WO | WO-15/19257 A1 | 2/2015 |
| WO | WO-17/25789 A1 | 2/2017 |
| WO | WO-2017/213783 | 12/2017 |
| WO | WO-2018/040275 | 3/2018 |
| WO | WO-18/224496 A1 | 12/2018 |
| WO | WO-19/77381 A1 | 4/2019 |
| WO | WO-2019/077381 | 4/2019 |
| WO | WO-2019/096908 | 5/2019 |

(56) References Cited

FOREIGN PATENT DOCUMENTS

| WO | WO-2019/096913 | 5/2019 |
|---|---|---|
| WO | WO-19/209268 A1 | 10/2019 |
| WO | WO-21/16457 A1 | 1/2021 |

OTHER PUBLICATIONS

Anchordoquy, T. J., et al., "Physical stabilization of DNA-based therapeutics," Drug Discovery Today, vol. 6, No. 9, pp. 463-470 (May 2001) (8 pages).
Ash, "Chronic peritoneal dialysis catheters: overview of design, placement, and removal procedures," Semin Dial., Jul.-Aug. 2003, 16(4):323-334 (12 pages).
Barnard, "The Effects of Extreme Cold on Sensory Nerves," Annals of the Royal College of Surgeons of England, 1980, 62:180-187 (8 pages).
Bejjani, F. J., et al., "Adipocyte Viability Study in an Accredited Cryolab. Effect of Age, Harvesting Technique, Sample Size, Freezing Delay, Freezing Duration, and Shipping," pp. 1-20, academia.edu (Apr. 2015) (20 pages).
Benner, J. and Konig, E., "The Growing Role of Biobanking in Today's Medical Environment," BioProcess Int., pp. 10, 12, and 14 (Mar. 2010) (3 pages).
Brink et al., "Abdominoplasty with direct resection of deep fat," Plast Reconstr Surg., May 2009, 123(5):1597-1603, doi: 10.1097/PRS.0b013e3181a07708 (7 pages).
Burgoyne, Francesca, "Preventing suspension settling during injection," Chips and Tips, Royal Society of Chemistry, Aug. 21, 2007—https://blogs.rsc.org/chipsandtips/2007/08/21/preventing-suspension-settling-during-injection/?doing_wp_cron=1576600990.3217470645904541015625 (14 pages).
Calandria, "Cryoanalgesia for Post-Herpetic Neuralgia: A New Treatment," International Journal of Dermatology, doi: 10.1111/j.1365-4632.2010.04792.x, pp. 1-5 (2010) (5 pages).
Conaway, "Ice Packs in Diabetic Neuropathy," The Physical Therapy Review, 1961, 41 (8):586-588 (3 pages).
Ding et al., "Association between non-subcutaneous adiposity and calcified coronary plaque: a substudy of the Multi-Ethnic Study of Atherosclerosis," Am J Clin Nutr., Sep. 2008, 88(3):645-650 (6 pages).
Dua, J.S., et al., "Liposome: Methods of Preparation and Applications," Int'l J. of Pharmaceuticals Studies & Research, vol. III, Issue II, Apr.-Jun. 2012, pp. E-ISSN 2229-4619 (7 total pages).
Ehrhardt, R. and Thompson, M., "The Big Freeze," Innovations in Pharmaceutical Technology, Issue 54, pp. 44-47 (Sep. 2015) (4 pages).
European Patent Office, Extended European Search Report, Application No. 17757262.5, dated Aug. 26, 2019 (14 total pages).
Extended European Search Report for 17847328.6 dated Dec. 7, 2020 (14 pages).
Extended European Search Report dated Aug. 26, 2019 for Application No. EP 17757262.5 (14 total pages).
Extended European Search Report dated Jun. 26, 2018 for Application No. EP 15836780.5 (10 total pages).
Fox et al., "Abdominal visceral and subcutaneous adipose tissue compartments: association with metabolic risk factors in the Framingham Heart Study," Circulation, 116:39-48 (Jul. 3, 2007) (10 pages).
Fruhstorfer, et al., "The Effects of Thermal Stimulation on Clinical and Experimental Itch," Pain, 1986, 24(2):259-269 (11 pages).
Gage, A.A., "Experimental cryosurgery investigations in vivo," Cryobiology, vol. 59, pp. 229-243 (2009) (15 pages).
Garaulet et al., "Relationship between fat cell size and No. and fatty acid composition in adipose tissue from different fat depots in overweight/obese humans," Int J Obes (Lond), Jun. 2006, 30(6):899-905 (7 pages).
Garbay, et al., "Myelin Synthesis in the Peripheral Nervous System," Progress in Neurobiology, 2000, 61:267-304 (38 pages).
Garibyan, L., et al., Neural Selective Cryoneurolysis with Ice Slurry Injection in a Rat Model, Anesthesiology, vol. 133, No. 1, pp. 185-194 (Jul. 2020) (10 pages).
Garibyan, L., et al., "Subcutaneous Fat Reduction with Injected Ice Slurry," Plas. Reconstr. Surg., vol. 145, No. 4, 725e-733e (Apr. 2020) (9 pages).
Ge, et al., "Calculations of Freezing Point Depression, Boiling Point Elevation, Vapor Pressure and Enthalpies of Vaporization of Electrolyte Solutions by a Modified Three-Characteristic Parameter Correlation Model," Journal of Solution Chemistry, 2009, 38:1097-1117 (21 pages).
Ge, et al., "Estimation of Freezing Point Depression, Boiling Point Elevation, and Vaporization Enthalpies of Electrolyte Solutions," Industrial & Engineering Chemistry Research, 2009, 48(4):2229-2235 (7 pages).
Glass, J. D., et al. "Lumbar Intraspinal Injection of Neural Stem cells in Patients with Amyotrophic Lateral Sclerosis: Results of a Phase I Trial in 12 patients," Stem Cells—Regenerative Medicine, vol. 30, pp. 1144-1151 (2012) (9 pages).
Gradinger et al., "Chapter 63: Abdominoplasty, The Art of Aesthetic Surgery: Principles and Techniques," Foad Nahai ed.—St. Louis, Missouri, 74 total pages: pp. 2352-2422 with 3 cover pages (2005) (74 pages).
Halkier-Sorensen, et al., "The Relevance of Low Skin Temperature Inhibiting Histamine-Induced Itch to the Location of Contact Urticarial Symptoms in the Fish Processing Industry," Contact Dermatitis, 1989, 21(3):179-183 (5 pages).
Han, et al., "Efficacy and Safety of High Concentration Lidocaine for Trigeminal Nerve Block in Patients with Trigeminal Neuralgia," International Journal of Clinical Practice, https://doi.org/10.1111/j.1742-1241 .2007.01568.x, first published Nov. 23, 2007 (Abstact Only: 3 total pages).
Hargreaves, et al., "A New and Sensitive Method for Measuring Thermal Nociception in Cutaneous Hyperalgesia," Pain, 1988, 32:77-88 (12 pages).
International Preliminary Report on Patentability dated Aug. 30, 2012 for Application No. PCT/US2011/024766 (9 total pages).
International Preliminary Report on Patentability dated Mar. 14, 2019 for Application No. PCT/US2017/048995 (11 total pages).
International Preliminary Report on Patentability dated Mar. 9, 2017 for Application No. PCT/US2015/047292 (8 total pages).
International Preliminary Report on Patentability dated Mar. 9, 2017 for Application No. PCT/US2015/047301 (10 total pages).
International Preliminary Report on Patentability dated Sep. 7, 2018 for Application No. PCT/US2017/019268 (8 total pages).
International Search Report and Written Opinion for International Application No. for PCT/US2015/047301 dated Dec. 14, 2015 (19 total pages).
International Search Report and Written Opinion for International Application No. PCT/US2015/047292 dated Dec. 7, 2015 (9 total pages).
International Search Report and Written Opinion for PCT/US2020/043280 dated Nov. 9, 2020 (14 pages).
International Search Report and Written Opinion dated Apr. 12, 2011 for Application No. PCT/US2011/024766 (11 total pages).
International Search Report and Written Opinion dated May 15, 2017 for Application No. PCT/US2017/019268 (8 total pages).
International Search Report and Written Opinion dated Nov. 3, 2017 for Application No. PCT/US2017/048995 (16 total pages).
Ivana Sramkova et al., "A Novel Approach to Lab-In-Syringe—Single Drop Microextraction and On-Drop Sensing of Ammonia," to appear in Analytica Chimica Acta, 10.1016/j.aca.2016.06.039, 2016 (44 pages).
Kauffeld, et al., "Ice Slurry Applications," Int. J. Refrig., 2010, 33(8):1491-1505 (Autho Manuscript—35 total pages).
Kasza, K., "Medical Ice Slurry Coolants for Inducing Targeted Organ/Tissue Protective Cooling," Argonne National Laboratory, pp. 1-8 (Jun. 2008) (9 pages).
Lampe, et al., "Rapid Induction of Heterogeneous Ice Nucleation in a Biologically Compatible Coolant," International Journal of Transport Phenomena, 2011, 12(3-4):307-317 (Author Manuscript—23 total pages).

(56) References Cited

OTHER PUBLICATIONS

Langert, K. A. and Brey, E. M., "Strategies for Targeted Delivery to the Peripheral Nerve," Frontiers in Neuroscience, vol. 12, Article 887, pp. 1-10 (Nov. 2018) (10 pages).
Laven et al., "A pilot study of ice-slurry application for inducing laparoscopic renal hypothermia," BJU Int., 99(1):166-170 (2006) (5 pages).
Laverson, "Improving abdominoplasty results: reconstruction of the linea alba sulcus by direct fat excision," Aesthet Surg J., Nov.-Dec. 2006, 26(6):682-686, doi: 10.1016/j.asj.2006.10.01 (5 pages).
Lenz, et al., "The Freezing Threshold of the Peripheral Motor Nerve: An Electrophysiological and Light-Microscopical Study on the Sciatic Nerve of the Rabbit," Cryobiology, 1975, 12(5):486-496 (11 pages).
Matthias, D. M., et al., "Freezing temperatures in the vaccine cold chain: A systematic literature review," Vaccine, vol. 25, pp. 3980-3986 (available online Mar. 7, 2007) (7 pages).
Mitchell, et al., "Degeneration of Non-Myelinated Axons in the Rat Sciatic Nerve Following Lysolecithin Injection," Aeta Neuropathologica, 1982, 56(3):187-193 (7 pages).
Modak, et al., "Agglomeration Control of Ice Particles in Ice-Water Slurry System Using Surfactant Additives," HVAC&R Research, Oct. 2002, 8(4):453-466 (14 pages).
No Author Listed, World Fine Chemicals Handbook. Institute of Science and Technology Information,Ministry of Chemical Industry, Ed. May 31, 1986; 187-190 (6 pages).
No Author, "Biomaterial Transporter Freezes Samples for up to 8 Hours with Lid off," Clinical Lab Products, three total pages (Sep. 15, 2014), last retrieved on Mar. 11, 2021 from https://clpmag.com/lab-equipment/biomaterial-transporter-freezes-samples-8-hours-lid/ (3 pages).
No Author, "Polysorbate-20," last retrieved on Mar. 15, 2013 from https://web.archive.org/web/20130315082056/http://www.ewg.org:80/skindeep/ingredient/705137/ POLYSORBATE-20 (3 total pages).
No Author, Isotonic (https://biologydictionary.net/isotonic/) accessed Jun. 21, 2018, pp. 1-4 (Year: 2018) (4 pages).
Partial Supplementary European Search Report dated Mar. 22, 2018 for Application No. EP 15836780.5 (12 total pages).
Partial Supplementary European Search Report for 17847328.6 dated Mar. 24, 2020 (16 pages).
PCT International Search Report and Written Opinion for PCT/US2017/19268 dated May 15, 2017 (8 total pages).
Peltonen, S., et al., "Barriers of the peripheral nerve," Tissue Barriers, vol. 1, Issue 3, e24956-1-e24956-6 (Jul./Aug./Sep. 2013) (6 pages).
Pradel, et al., "Cryosurgical Treatment of Genuine Trigeminal Neuralgia," British Journal of Oral and Maxillofacial surgery, 2002, 40:244-247 (4 pages).
Pramanick, et al., "Excipient Selection in Parenteral Formulation Development," Pharma Times, Mar. 2013, 45(3):65-77 (13 pages).
Rathmell et al., "Chapter 14—Intercostal Nerve Block and Neurolysis," Atlas of Image-Guided Intervention in Regional Anesthesia and Pain Medicine, James P. Rathmell (ed.), Lippincott Williams & Wilkins (Philadelphia, PA), Second Edition, 5 total pages: pp. 201-203 with cover pages (2012) (5 pages).
Rengachary, S.S., et al., "Effect of Glycerol on Peripheral Nerve: An Experimental Study," vol. 13, No. 6, pp. 681-688 (1983) (8 pages).
Schallenberger, M., et al., "The effect of temperature exposure during shipment on a commercially available demineralized bone matrix putty," Cell and Tissue Banking, vol. 17, No. 4, pp. 677-687 (published online Aug. 25, 2016) (11 pages).
Shikanov, et al., "Microparticulate ICE Slurry for Renal Hypothermia: Laparoscopic Partial Nephrectomy in a Porcine Model," Urology, 2010, 76(4)1012-1016 (5 pages).
Smyth, T. J., et al. "Moisture Content Impacts the Stability of DNA Adsorbed onto Gold Microparticles." Journal of Pharmaceutical Sciences vol. 100, No. 11, pp. 4845-4854 (Nov. 2011) (10 pages).
Suzuki, et al., "Particle Size Depression and Drag Reduction of Ice Slurry Treated with Combination Additives of Surfactants and Poly(vinyl alcohol)," Journal of Chemical Engineering of Japan, 2010, 43(6):482-486 (5 pages).
Syringe Stirrer neMIX, CETONI GMBH—https://www.cetoni.com/products/syringe-stirrer-nemix/, retrieved Dec. 17, 2019 (9 pages).
Van Eps et al., "Distal limb cryotherapy for the prevention of acute laminitis," Clin Tech Equine Pract., 2004, 3:64-70 (7 pages).
Vanden Hoek, et al., "Induced Hypothermia by Central Venous Infusion: Saline Ice Slurry Versus Chilled Saline," Grit Care Med., 2004, 32(9)(Suppl.):S425-S431 (7 pages).
VP 710D3—Multi Stirrus, V&P Scientific, Inc.—http://vp-sci.com/vp-710d3.html, retrieved Dec. 17, 2019 (3 pages).
Wang, J., et al., "Transporting Cells in Semi-Solid Gel Condition and at Ambient Temperature," PloS One, vol. 10, No. 6, e0128229, pp. 1-9 (Jun. 22, 2015) (9 pages).
Yamamoto et al., "Adipose depots possess unique developmental gene signatures,"Obesity (Silver Spring), May 2010, 18(5):872-878. doi: 10.1038/oby.2009.512 (Epub Jan. 28, 2010) (7 pages).
Yao et al., "Medical Polymer Materials," Chemical Industry Press, Apr. 30, 2008, pp. 908-910 (5 pages).

* cited by examiner

| ICE PERCENTAGE CALCULATIONS | | |
|---|---:|---|
| Mixture: | Value | Units |
| Volume normal saline | 80 | mL |
| Volume Glycerol | 20 | mL |
| Temperature setpoint | −10 | °C |
| Mass H2O | 79.6 | g |
| Mass NaCl | 0.72 | g |
| % Glycerol | 20% | L/L solution |
| Mass Glycerol | 25.2 | g |
| Ice percentage | 30% | ice by mass |

Fig 2

APPARATUS FOR CREATION OF INJECTABLE SLURRY

This patent disclosure contains material that is subject to copyright protection. The copyright owner has no objection to the facsimile reproduction of the patent document or the patent disclosure as it appears in the U.S. Patent and Trademark Office patent file or records, but otherwise reserves any and all copyright rights.

TECHNICAL FIELD

The present invention relates generally to apparatuses, systems, and methods for creating injectable cold slurries. More particularly, the present invention relates to a syringe with an internal mechanism for blending internal syringe contents to create an injectable cold slurry.

BACKGROUND

Cold slurries (e.g., ice slurries) are known in the art as compositions that are made of sterile ice particles of water, varying amounts of excipients or additives such as freezing point depressants, and, optionally, one or more active pharmaceutical ingredients, as described in U.S. application Ser. No. 15/505,042 ("'042 Application"; "Publication No. US2017/0274011), incorporated in its entirety herein. The cold slurries can be delivered, preferably via injection, to a tissue of a subject, preferably a human patient, to cause selective or non-selective cryotherapy and/or cryolysis for prophylactic, therapeutic, or aesthetic purposes. Injectable cold slurries may be used for treatment of various disorders that require inhibition of nerve conduction. For example, U.S. application Ser. No. 15/505,039 ("'039 Application"; Publication No. US2017/0274078), incorporated in its entirety herein, discloses the use of slurries to induce reversable degeneration of nerves (e.g., through Wallerian degeneration) by causing crystallization of lipids in the myelin sheath of nerves. The '039 Application also discloses using injectable cold slurries to treat various other disorders that require inhibition of somatic or autonomic nerves, including motor spasms, hypertension, hyperhidrosis, and urinary incontinence.

A method of preparing a cold slurry is shown in U.S. application Ser. No. 16/080,092 ("'092 Application"; Publication No. US2019/0053939). However, the '092 Application requires installation of a medical cold slurry production system at the point of care. Also, this requires the point of care to be concerned with maintaining sterility of the cold slurry during and following manufacture.

Co-pending U.S. application Ser. No. 17/062,955 ("'955 application") discloses a method of easily transporting a sterile biomaterial to a point of care using standard shipping techniques, where the biomaterial can be transformed into a flowable and injectable cold slurry at a point of care without requiring manufacturing equipment to be available at the point of care and without compromising the sterility of the biomaterial at the point of care. The disclosure in the present application is compatible with the methods and systems disclosed in the '955 application.

There exists a need for apparatuses, systems, and methods that allow for preparation of a flowable and injectable cold slurry at a clinical point of care without compromising the sterility of the slurry during preparation and without requiring manufacturing equipment or slurry components to be available at the point of care. The present disclosure provides for improved apparatuses, systems, and methods of transforming a composition into a flowable and injectable cold slurry using components internal and/or external to a container holding the composition, such as a syringe containing a crystallized solution adapted to interact with external hardware to agitate the solution to form a slurry. The disclosure provides for apparatuses, systems, and methods that preserve the sterility of the composition and reduce the time required to provide a therapeutic substance to a patient.

SUMMARY

In one aspect, the invention provides for a system for creating an injectable and flowable cold slurry, the system comprising: a housing; a mount operatively connected to the housing configured to accept a container; a first motor configured to move the mount from a first position to a second position; a second motor; and a drive shaft in communication with the second motor, wherein the drive shaft is configured to rotate to cause an internal volume of the container to be transformed into the injectable and flowable cold slurry.

In some embodiments, the container is a syringe, and wherein the syringe comprises a blade shaft. In some embodiments, the blade shaft comprises a plurality of blades. In some embodiments, the blade shaft is configured to engage with the drive shaft, and wherein the blade shaft is configured to rotate to cause the internal volume of the syringe to be transformed into the injectable and flowable cold slurry. In some embodiments, the system further comprises one or more rails, wherein the mount is configured to move along the rails from the first position to the second position. In some embodiments, the first motor is selected from a brushless DC motor or a linear actuator. In some embodiments, the second motor is selected from a brushless DC motor or a spindle motor. In some embodiments, the system further comprises a pulley in communication with the second motor, wherein the pulley is configured to rotate the drive shaft. In some embodiments, the system further comprises one or more pulleys in communication with the first motor, wherein the one or more pulleys are configured to move the mount from the first position to the second position. In some embodiments, the movement from the first position to the second position is along a longitudinal axis. In some embodiments, the system further comprises a worm and a worm gear, wherein the worm is in communication with the worm gear, and wherein the worm gear is configured to rotate a pulley to move the mount from the first position to the second position.

In another aspect, the invention provides for a system for creating an injectable and flowable cold slurry, the system comprising: a sled configured to accept a syringe; a first motor configured to move the sled from a first position to a second position; a second motor; a drive shaft in communication with the second motor; and a pulley in communication with the second motor and the drive shaft, wherein the drive shaft is configured to rotate to cause an internal volume of the syringe to be transformed into the injectable and flowable cold slurry.

In some embodiments, the system further comprises the syringe, wherein the syringe comprises a blade shaft. In some embodiments, the blade shaft comprises a plurality of blades. In some embodiments, a plunger of the syringe comprises a hollow portion, and wherein the blade shaft is configured to retract into the hollow portion of the plunger. In some embodiments, the system further comprises one or more rails, wherein the rails are configured to move the sled from the first position to the second position. In some embodiments, the first motor is selected from a brushless DC motor or a linear actuator. In some embodiments, the second motor is selected from a brushless DC motor or a spindle motor. In some embodiments, the system further comprising one or more pulleys in communication with the first motor, wherein the one or more pulleys are configured to move the sled from the first position to the second position. In some embodiments, the system further comprises a safety door.

In another aspect, the invention provides for an apparatus for creating an injectable and flowable cold slurry, the apparatus comprising: a sled configured to accept a syringe; a first motor configured to move the sled from a first position to a second position; a drive shaft; and a second motor configured to cause rotation of the drive shaft, wherein the rotation of the drive shaft causes an internal volume of the syringe to be formed into the injectable and flowable cold slurry.

In some embodiments, the sled further comprises a dock configured to accept the syringe. In some embodiments, the sled comprises a front holder mount and a back-holder mount, and wherein the front holder mount is configured to be moved to an open position to accept the syringe. In some embodiments, the apparatus further comprises one or more pulleys in communication with the first motor, wherein the one or more pulleys are configured to move the sled from the first position to the second position.

In another aspect, the invention provides for an apparatus for transforming an internal volume of a container into an injectable and flowable cold slurry, the apparatus comprising: a mount configured to accept the container; a drive shaft; and a motor in communication with the drive shaft, wherein the motor is configured to rotate the drive shaft to transform the internal volume of the container into the injectable and flowable cold slurry.

In some embodiments, the apparatus further comprises a second motor configured to move the mount from a first position to a second position. In some embodiments, the container is a syringe, and wherein the syringe comprises a blade shaft. In some embodiments, the blade shaft comprises a first bayonet connector configured to engage with a second bayonet connector, and wherein the drive shaft comprises the second bayonet connector. In some embodiments, the apparatus further comprising one or more pulleys in communication with the first motor, wherein the one or more pulleys are configured to move the sled from the first position to the second position. In some embodiments, the apparatus further comprises one or more rails, wherein the mount is configured to move along the rails from the first position to the second position.

In one aspect, the invention provides for a system for creating an injectable and flowable cold slurry, the system comprising: a housing configured to accept a container; a first rotating magnet; and a first motor, wherein the first motor is configured to spin the first rotating magnet to cause an internal volume of the container to be transformed into the injectable and flowable cold slurry.

In another aspect, the invention provides for an apparatus for creating an injectable and flowable cold slurry, the apparatus comprising: a housing configured to accept a container; a first rotating magnet; and a first motor, wherein the first motor is configured to spin the first rotating magnet to cause an internal volume of the container to be transformed into the injectable and flowable cold slurry.

In some embodiments, the container is a syringe. In some embodiments, the container comprises a blade and a magnetic component. In some embodiments, the first rotating magnet is configured to rotate the magnetic component. In some embodiments, the container comprises a plurality of blades. In some embodiments, the plurality of blades comprises one or more blade rows positioned along a long central shaft, and wherein the long central shaft is configured to fit inside of the container. In some embodiments, the long central shaft comprises a plurality of magnetic components. In some embodiments, the blade comprises an "X" shape. In some embodiments, the system further comprises a compartment configured to hold at least one battery. In some embodiments, the housing has dish outs, wherein the dish outs are configured to allow a user to remove a syringe from the housing. In some embodiments, the system further comprises a second rotating magnet and a second motor. In some embodiments, the housing is further configured to accept the container in a position between the first rotating magnet and the second rotating magnet. In some embodiments, the housing is further configured to accept the container in a position between the first motor and the second motor.

In another aspect the invention provides for an apparatus for creating an injectable and flowable cold slurry, the apparatus comprising: a housing; a first rotating magnet; and a first motor, wherein the first motor is configured to spin the first rotating magnet to cause an internal volume of a container to be transformed into the injectable and flowable cold slurry.

In some embodiments, the apparatus is handheld. In some embodiments, the container is a syringe. In some embodiments, the container comprises a blade and a magnetic component. In some embodiments, the first rotating magnet is configured to agitate the magnetic component. In some embodiments, the container comprises a plurality of blades.

In another aspect, the invention provides for a system for creating an injectable and flowable cold slurry, the system comprising: a housing configured to accept a container; a magnetic cup; and a motor, wherein the motor is configured to spin the magnetic cup to cause an internal volume of the container to be transformed into the injectable and flowable cold slurry.

In some embodiments, the system further comprises a linear actuator, wherein the linear actuator is configured to move the motor from a first position to a second position along a linear axis. In some embodiments, the container is a syringe. In some embodiments, the container comprises a blade and a magnetic component. In some embodiments, the magnetic cup is configured to agitate the magnetic component. In some embodiments, the container comprises a plurality of blades.

In another aspect, the invention provides for an apparatus for creating an injectable and flowable cold slurry, the apparatus comprising: a housing configured to accept a container, wherein the container comprises a rotor; and a plurality of stator coils, wherein the plurality of stator coils is configured to spin the rotor to cause an internal volume of the container to be transformed into the injectable and flowable cold slurry.

In some embodiments, the container is a syringe. In some embodiments, the container comprises a blade. In some embodiments, the blade is attached to the rotor.

In another aspect, the invention provides for a system for determining a status of a docking station configured to create an injectable and flowable cold slurry, the system comprising: a processor; and a memory storing processor-executable instructions that, when executed by the processor, cause the processor to: perform a self-test to determine whether a docking station is one of operational, non-operational, or operational with a non-blocking issue; if the docking station is determined to be operational or operational with a non-blocking issue, then the instructions cause the processor to initiate a blending operation of the docking station and determines whether the blending operation is a success or a failure; and if the docking station is determined to be non-operational, then the instructions cause the processor to inform a user that the docking station is non-operational.

In another aspect, the invention provides for a non-transitory computer-readable storage medium comprising computer-readable instructions for determining a status of a docking station configured to create an injectable and flowable cold slurry that, when executed by a processor cause the processor to: perform a self-test to determine whether a docking station is one of operational, non-operational, or operational with a non-blocking issue; if the docking station is determined to be operational or operational with a non-blocking issue, the computer-readable instructions cause the processor to initiate a blending operation of the docking station and determine whether the blending operation is a success or a failure; and if the docking station is determined to be non-operational, inform a user that the docking station is non-operational.

In some embodiments, the success of the blending operation further causes the processor to indicate to a user that a syringe is ready for injection of the injectable and flowable cold slurry into a patient. In some embodiments, the failure of the blending operation further causes the processor to indicate to a user that a syringe is not ready for injection of an internal contents of a syringe into a patient. In some embodiments, the self-test comprises determining if a door is closed or open, and wherein the door is configured to provide a barrier to the docking station. In some embodiments, the self-test comprises determining if a syringe is present in the docking station. In some embodiments, the self-test comprises moving a holder mount from a first position to a second position and spinning a motor. In some embodiments, the self-test comprises checking a temperature reading of a PCB temperature sensor. In some embodiments, the blending operation is initiated after the processor determines that a syringe is present in the docking station. In some embodiments, the success of the blending operation further causes the processor to measure a temperature of an internal volume of a syringe. In some embodiments, if the temperature of the internal volume of the syringe is greater than about −6.5° C., the processor the processor indicates to the user that the syringe may soon expire. In some embodiments, if the temperature of the internal volume of the syringe is greater than about −6° C., the processor the processor indicates to the user that the syringe has expired.

BRIEF DESCRIPTION OF THE DRAWINGS

The following figures depict illustrative embodiments of the invention.

FIG. 2 is a table showing the breakdown by volume and weight of components of an exemplary biomaterial that can form an injectable cold slurry.

FIG. 34 is a cross-sectional side view of a syringe dispensing slurry for administration to a patient with a rotor located inside of the syringe barrel.

FIG. 35 is a cross-sectional plan view taken along line 35-55 of FIG. 34 showing the rotor with fluid passages to allow slurry to pass through.

DETAILED DESCRIPTION

Figure 1:
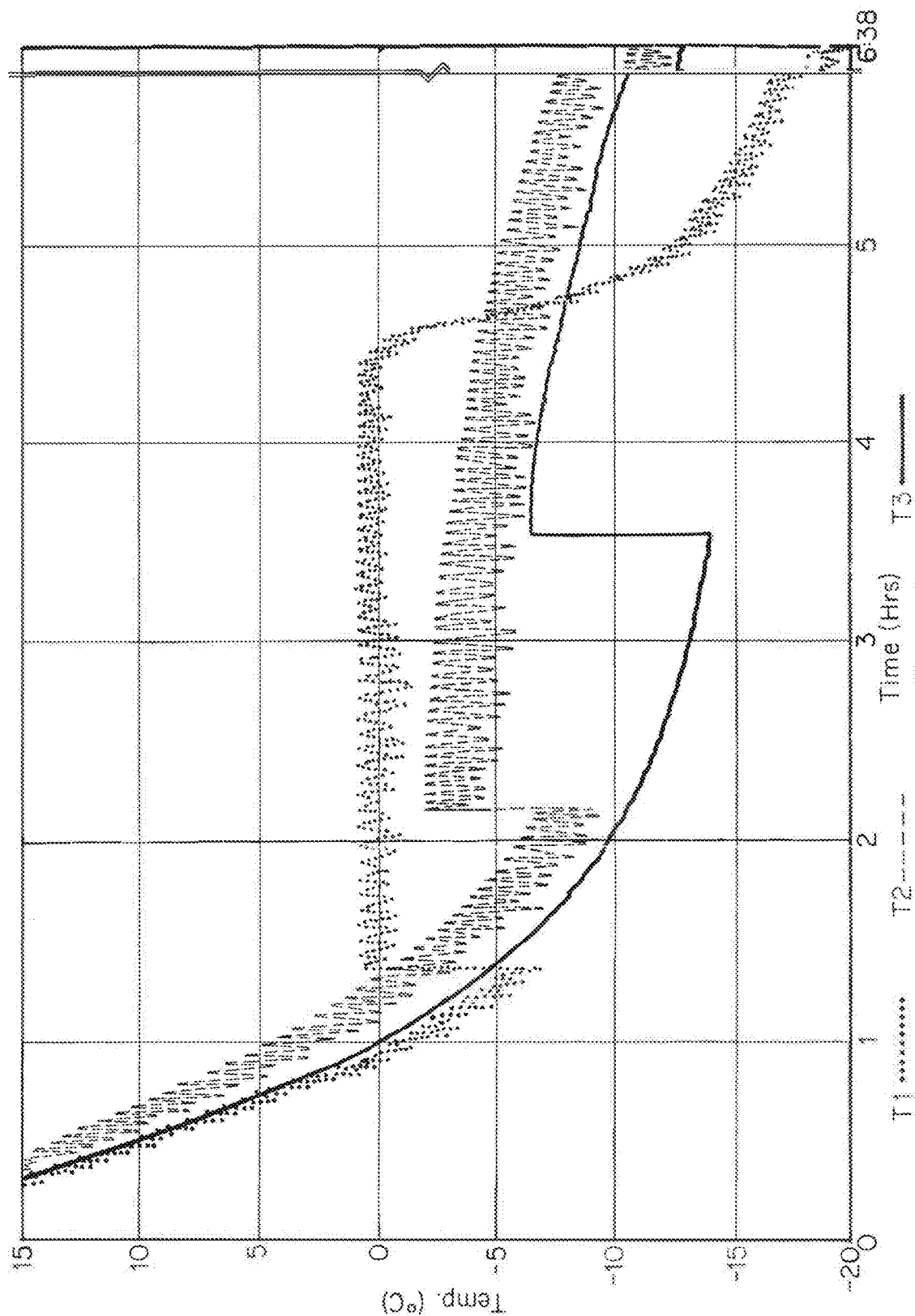
FIG. 1 depicts a freezing point depression graph for liquid water, a solution containing 10% glycerin volume by volume (v/v), and a solution containing 20% glycerin (v/v).

The present disclosure is drawn to apparatuses, devices, systems, and methods of preparation of injectable biological material, such as a cold slurry. The present disclosure provides for apparatuses, devices, systems, and methods that allow for blending of a solution having crystals to form an injectable and flowable cold slurry for administration to a patient at a clinical point of care. The present disclosure provides a container, such as a syringe, that can be pre-loaded with a biomaterial, sterilized after the biomaterial has been loaded into the container, and shipped to the point of care without compromising the sterility of the container. The biomaterial inside the container can then be transformed into an injectable and flowable cold slurry at the point of care. The biomaterial can be transformed into an injectable and flowable cold slurry by subjecting the syringe to sub-0° C. temperatures, and manipulating physical components provided inside the container. The physical components inside the container can be manipulated using components that are shipped with the container, components that are part of the shipping vessel in which the container is shipped, or components that are stored at the point of care, any of which may be handheld components. Thus, in some embodiments, the biomaterial can be transformed into an injectable and flowable cold slurry at the point of care without compromising its sterility or requiring the point of care to take any extra steps to maintain sterility.

In some embodiments, the biomaterial is a cold slurry (e.g., ice slurry) that can be delivered via injection directly to tissue of a human patient or a subject (e.g., a human who is not a patient or a non-human animal) for prophylactic, therapeutic, or aesthetic purposes as disclosed in U.S. application Ser. No. 15/505,042 (Publication No. US2017/0274011), incorporated in its entirety herein. The injectable slurry can be used for selective or non-selective cryotherapy or cryolysis. In some embodiments, the therapeutically effective injectable slurry is comprised entirely of water and non-active excipient materials. In other embodiments, the slurry further comprises a known active pharmaceutical compound.

In some embodiments, a syringe containing a biomaterial is received at a clinical point of care. The biomaterial may be received in a crystallized (or partially crystallized) state or may be received in an aqueous state. The syringe with the biomaterial may be cooled, such as by placing the syringe in a freezer to form a crystallized (or partially crystallized) composition.

In some embodiments, the syringe containing the biomaterial is adapted to transform a crystallized, or partially crystallized, composition into a flowable and injectable cold slurry. The syringe may contain within its internal volume one or more of blades, magnets, or other components capable of agitating the internal syringe contents. The syringe is configured to interact with an external apparatus, such as a docking station available (or received) at the point of care. The syringe interacts with the external apparatus, such as the docking station, such that when the external apparatus is activated using a power source, the internal syringe contents are agitated (e.g., blended) to break up the crystallized internal contents to form an injectable and flowable cold slurry with a certain percentage of ice particles. For example, a drive shaft in a docking station may connect with a blade shaft inside of the plunger of the syringe and blending is effectuated by a motor located in the docking station. The motor rotates the drive shaft and blade shaft to cause spinning of the blades located within the syringe body to create an injectable and flowable cold slurry. In some embodiments, the syringe contains magnets that may be coupled to blades within its internal volume, which are adapted to rotate and cause blending of the internal syringe contents when interacting with a docking station having rotating magnets. A power source activates the rotating magnets on the docking station which in turn cause rotation of the magnets inside of the syringe to form an injectable and flowable cold slurry. In some embodiments, the syringe has magnets within its barrel which rotate in response to an external handheld component that has a spinning magnet. In some embodiments, the syringe and docking station form a brushless motor whereby the syringe has a rotor (with magnets) within its internal volume which spins to agitate (or blend) its internal contents when coils external to the syringe are activated using a power source. In some embodiments, the docking station (or housing external to the docking station, or handheld component) has one or more lights (e.g., LED light) to indicate operational status and safety parameters of the docking station and syringe.

In some embodiments, the final product to be administered via injection to a human patient or a subject (such as a human who is not a patient or a non-human animal) is a cold slurry comprised of sterile ice particles of water and varying amounts of excipients or additives such as freezing point depressants. For example, the percentage of ice particles in the cold slurry can constitute less than about 10% by weight of the slurry, between about 10% by weight and about 20% by weight, between about 20% by weight and about 30% by weight, between about 30% by weight and about 40% by weight, between about 40% by weight and about 60% by weight, more than about 60% by weight, and the like. The sizes of the ice particles will be controlled to allow for flowability through a vessel of various sizes (e.g. needle gauge size of between about 7 and about 43) as described in U.S. application Ser. No. 15/505,042 (Publication No. US2017/0274011) and incorporated herein. Further, other methods may be used to condition the size of the ice particles to allow for flowability through a vessel of various sizes. In some embodiments, the majority of ice particles have a diameter that is less than about half of the internal diameter of the lumen or vessel used for injection. For example, ice particles can be about 1.5 mm or less in diameter for use with a 3 mm catheter.

There are a variety of techniques that may be used to prepare a solution that can form a cold slurry. This disclosure is not limited to any particular method or technique.

In some embodiments, one or more excipients may be included in the slurry. An excipient is any substance, not itself a therapeutic agent, used as a diluent, adjuvant, and/or vehicle for delivery of a therapeutic agent to a subject or patient, and/or a substance added to a composition to improve its handling, stability, or storage properties. Excipients can constitute less than about 10% volume by volume (v/v) of the slurry, between about 10% v/v and about 20% v/v of the slurry, between about 20% v/v and about 30% v/v, between about 30% v/v and 40% v/v, and greater than about 40% v/v. Various added excipients can be used to alter the phase change temperature of the slurry (e.g., reduce the freezing point), alter the ice percentage of the slurry, alter the viscosity of the slurry, prevent agglomeration of the ice particles, prevent dendritic ice formation (i.e., crystals with multi-branching "tree-like" formations, such as those seen in snowflakes), keep ice particles separated, increase thermal conductivity of fluid phase, or improve the overall prophylactic, therapeutic, or aesthetic efficacy of the injectable slurry.

One or more freezing point depressants can be added as excipients to form slurries with freezing points below 0° C. Depressing the freezing point of the slurry allows it to maintain flowability and remain injectable while still containing an effective percentage of ice particles. Suitable freezing point depressants include salts (e.g., sodium chloride, betadex sulfobutyl ether sodium), ions, Lactated Ringer's solution, sugars (e.g., glucose, sorbitol, mannitol, hetastarch, sucrose, (2-Hydroxypropyl)β-cyclodextrin, or a combination thereof), biocompatible surfactants such as glycerol (also known as glycerin or glycerine), other polyols (e.g., polyvinyl alcohol, polyethylene glycol 300, polyethylene glycol 400, propylene glycol), other sugar alcohols, or urea, and the like. Other exemplary freezing point depressants are disclosed in U.S. application Ser. No. 15/505,042 (Publication No. US2017/0274011) and are incorporated in their entirety herein.

The concentrations of freezing point depressants will determine the ice particle percentage of the slurry and its flowability and injectability. The degree of freezing point depression can be calculated using the following formula as described in U.S. application Ser. No. 15/505,042 (Publication No. US2017/0274011), incorporated herein:

$$\Delta T_F = K_F b i$$

wherein $\Delta T_F$ is the freezing point depression (as defined by $T_{F\ (pure\ solvent)} - T_{F\ (solution)}$), $K_F$ is the cryoscopic constant, b is molality, and i is the Van't Hoff factor representing the number of ion particles per individual molecule of solute. Other methods of computing freezing point depression can also be used, as disclosed in U.S. application Ser. No. 15/505,042 (Publication No. US2017/0274011).

Referring to FIG. 1, a freezing point depression graph is shown for pure water T1, a mixture of water and 10% (v/v) glycerin T2, and a mixture of water and 20% (v/v) glycerin T3. In this graph, all the substances were placed in a freezer having a constant temperature of −20° C. The temperature was measured using a thermometer placed in each substance. The graph shows that a mixture of water and glycerin will have a different freezing point than that of pure water, which means the solution can be cooled to below 0° C. and only be partially crystallized. The graph shows that cooling causes pure water T1 to crystallize at an equilibrium freezing point of 0° C. This is indicated by the period of time where the pure water remains at a temperature of about 0° C., from about 1.3 hours to about 4.4 hours, which begins immediately after pure water T1 passes a supercooling point at about −6° C. Having an equilibrium window of crystallization (i.e., the "flat line" portion of pure water T1 in FIG. 1) is typical for a pure solvent. For the 10% glycerin solution T2, cooling causes the solution to begin crystallizing at an initial freezing point of about −3° C. after about 2.2 hours, and the crystallization continues as the temperature of the solution drops further to about −8° C. after about 6 hours. The initial crystallization occurs immediately after 10% glycerin solution T2 passes a supercooling point at about −8° C. (which can vary from sample to sample, e.g., supercooling point of between about −15° C. and about −3° C.), shown at around 2.2 hours. Having a descending temperature window of crystallization for the 10% glycerin solution T2 is typical for a solution (i.e., impure mixture). Similarly, for the 20% glycerin solution T3, cooling causes the solution to begin crystallizing at an initial freezing point of about −7° C. after about 3.5 hours (following an initial supercooling point which can vary from sample to sample, e.g., between about −25° C. and about −5° C.), and the crystallization continues as the temperature of the solution drops further to about −11° C. after about 6 hours and continues to decline thereafter past 6.5 hours. The initial crystallization occurs immediately after 20% glycerin solution T3 passes a supercooling point at about −14° C., shown at around 3.5 hours. Similar to the trace for 10% glycerin solution T2, the descending temperature window of crystallization for 20% glycerin solution T3 is typical for a solution.

Referring to FIG. 2, this chart shows the components of an exemplary biomaterial that can form a slurry. This chart shows that the percentage of ice for an exemplary biomaterial can be calculated for a particular temperature. The exemplary slurry contains 30% ice by mass (weight by weight; w/w) at −10° C. This exemplary slurry has 80 mL of saline (0.9% NaCl) and 20 mL of glycerol (i.e., glycerin). In weight, such a slurry has about 79.6 g of pure water, about 0.72 g of sodium chloride, and about 25.2 g of glycerol (approximately 20% v/v). In other embodiments, the slurry could contain higher or lower percentages of glycerol by adjusting the relative volume of glycerol to saline. For example, other suitable slurries contain about 10% glycerol (v/v), between about 10% and about 20% glycerol, about 30% glycerol, or more than about 30% glycerol. If an active pharmaceutical compound is to be added to the slurry, the concentration of saline can be adjusted accordingly to maintain the desired concentration of excipients such as glycerol. The percentage of ice will vary depending on the composition of the biomaterial.

Figure 3:
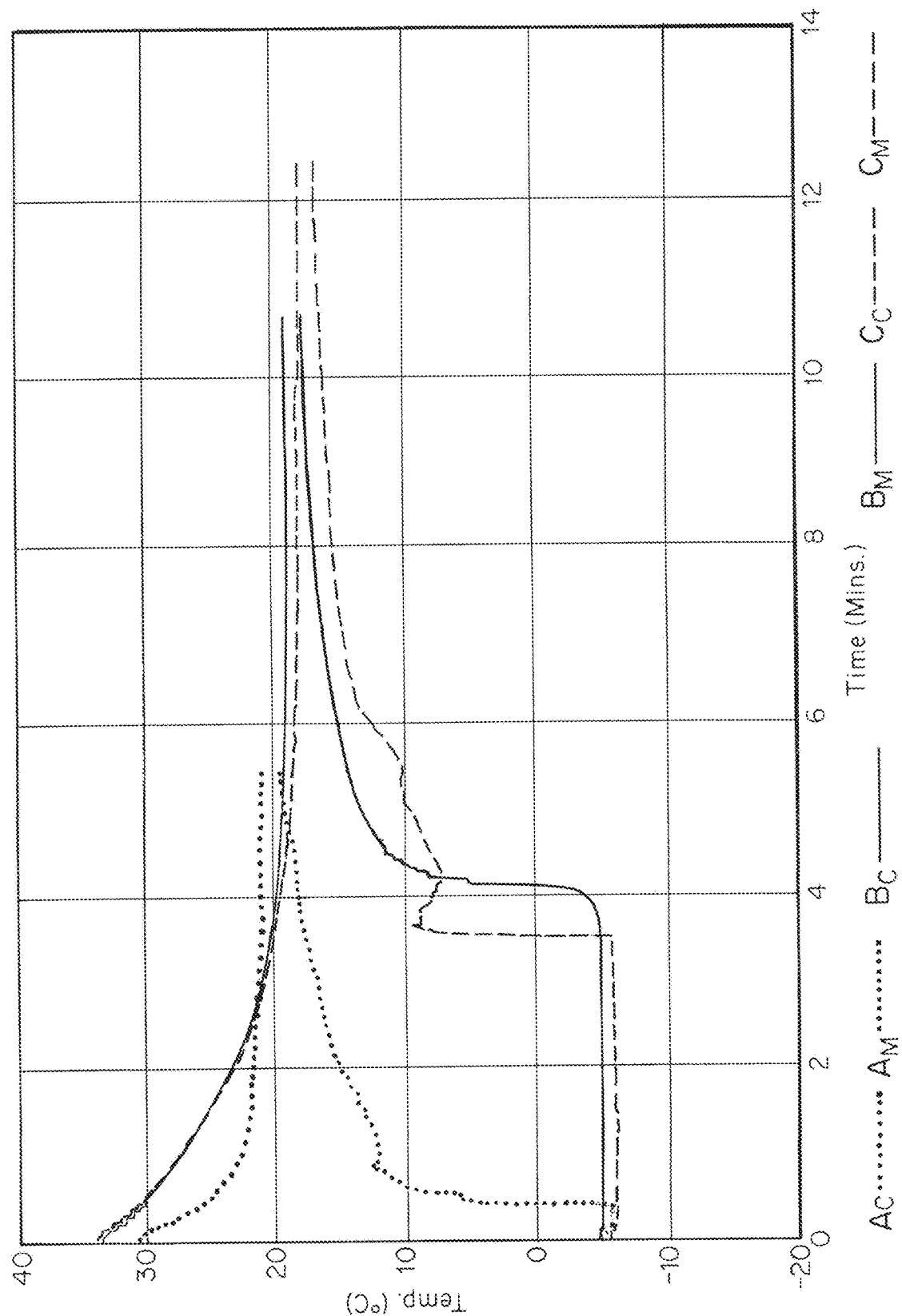
FIG. 3 is a graph showing the characterization of ice content of cold slurries having crystallization set points of −5.5° C. and −8.1° C.

Referring to FIG. 3, different slurry compositions (batches) are characterized with respect to their temperature profiles and ice content. The different slurry batches were placed into a copper plate that is heated to 40° C. and has thermocouple wires that measure changes in temperature of the slurry over time. The plotted data shows temperature change over time for three different slurry batches. The temperatures are measured at two different positions for each slurry: embedded inside of the copper plate (traces $A_C$, $B_C$, and $C_C$) and in the middle of the copper plate exposed to the outside of the plate (traces $A_M$, $B_M$, and $C_M$). The temperature traces show three separately created slurry batches: a slurry composition having 15% glycerin (having a temperature setpoint of −8.1° C.) is represented by traces $A_C$ and $A_M$, and two different slurry batches both having 10% glycerin (having a temperature setpoint of −5.5° C.) are represented by traces $B_C$ and $B_M$, as well as traces $C_C$ and $C_M$. When a slurry batch is first introduced into the copper plate, the thermocouple wire embedded inside the plate (traces $A_C$, $B_C$, and $C_C$) initially measures the warm temperature of the heated plate (e.g., 31° C. for trace $A_C$ at timepoint 0) and then reaches an equilibrium at a lower temperature due to the cooling effect of the introduced slurry (e.g., 22° C. for trace $A_C$ at around 2 minutes). On the other hand, for the thermocouple wire located in the middle of the plate, when a slurry is first introduced into the copper plate it immediately contacts the thermocouple wire since that wire is exposed. This causes an initially negative temperature reading in the middle position due to the crystallized slurry contacting the wire (e.g., −5° C. for trace $A_M$ at timepoint 0) followed by an equilibrium at a warmer temperature as the slurry begins to melt on the heated plate (e.g., 18° C. for trace $A_M$ at around 4 minutes). The thermocouple wire exposed to the outside of the plate (traces $A_M$, $B_M$, and $C_M$) can be used to detect phase transitions during which the crystallized slurry begins to melt. The graph shows that the two slurry compositions with 10% glycerin reach their phase transition at similar timepoints (at around 4 minutes for trace $B_M$, and at around 2.7 minutes for trace $C_M$), which differ from the phase transition for the 15% glycerin slurry (phase transition occurs at around 0.2 minutes for trace $A_M$). The graph also shows that the two slurry batches having the same composition (10% glycerin: traces $B_C$ and $B_M$ and traces $C_C$ and $C_M$) reach equilibrium (as measured by the two thermocouple wire positions) in a similar time frame and at similar temperatures of between about 15° C. and 19° C. depending on the location of the thermocouple (middle/bottom). On the other hand, the slurry with a different composition (15% glycerin: traces $A_C$ and $A_M$) has a different temperature profile from the other two, reaching an equilibrium sooner at the temperature of between about 19° C. and 22° C. depending on the location of the thermocouple (middle/bottom). FIG. 3 therefore demonstrates that slurries of different compositions have different temperature profiles and batch to batch consistency exists across slurries having the same composition (e.g., the slurry represented by $B_C$ and $B_M$ and slurry represented by $C_C$ and $C_M$ have similar temperature profiles which is different from that of slurry represented by $A_C$ and $A_M$).

Figure 4:
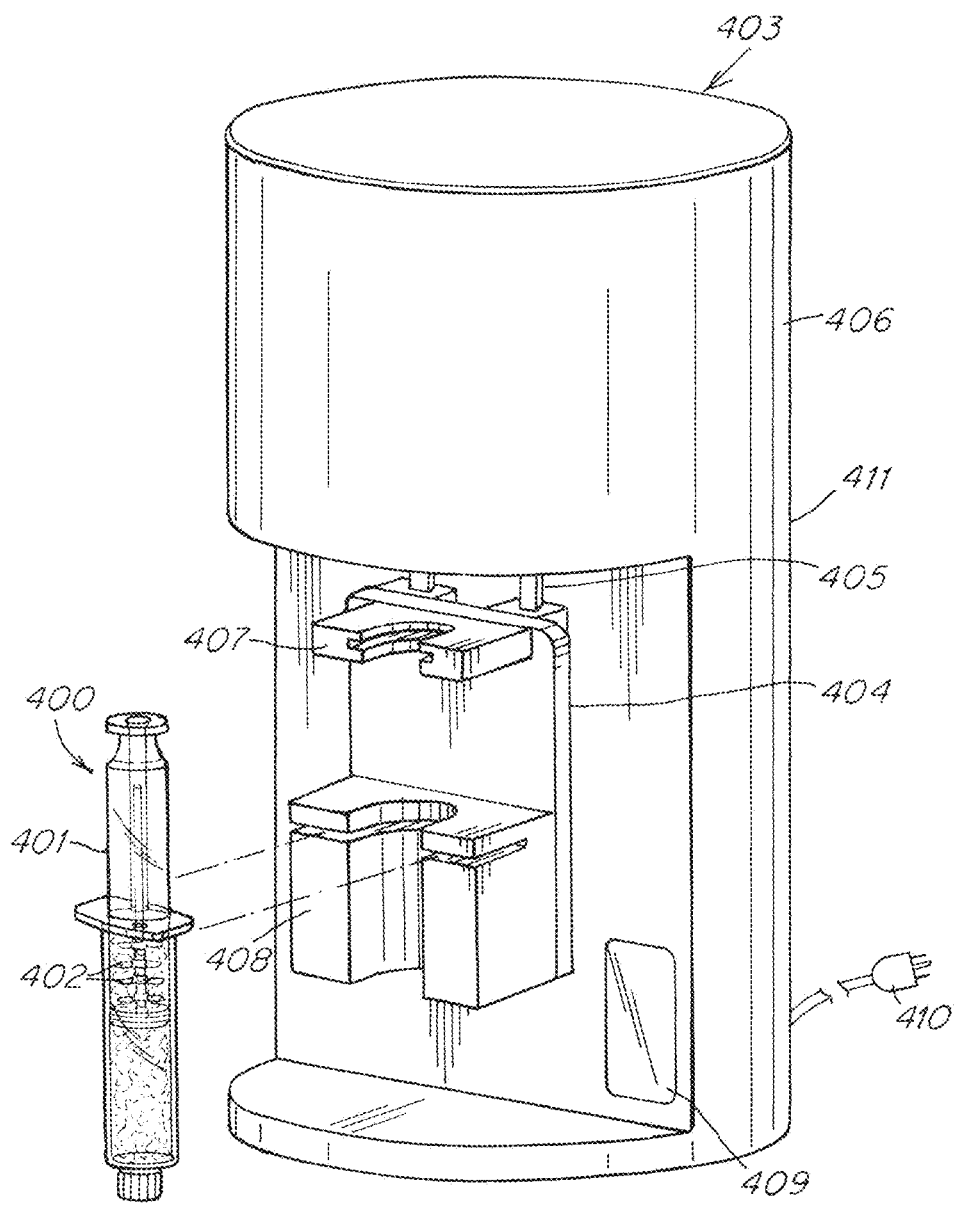
FIG. 4 is an exploded perspective view of a docking station configured to blend internal contents of a syringe and complementary syringe containing a biomaterial to be transformed into an injectable and flowable cold slurry.

The syringe containing a biomaterial may undergo temperature changes (e.g., by being placed in a freezer) to cause partial or full crystallization of the internal syringe contents which can then be subjected to mixing/blending to form a flowable and injectable slurry. Referring to FIG. 4, an exploded perspective view is shown of a docking station 403 and a syringe 400 that includes internal components that can be used to blend the biomaterial in the syringe. The depicted syringe 400 has a plunger 401 containing internal blades 402. Docking station 403 is configured to accept a syringe and to blend an internal volume of the syringe to create an injectable and flowable cold slurry. Sled 404 has an upper dock 407 and a lower dock 408, each comprising a semi-circular cutout slot configured to hold syringe 400. The slot in upper dock 407 is configured to hold plunger 401 in place, while the slot in lower dock 408 is configured to hold the barrel flange of syringe 400. Sled 404 can alternatively be adapted to hold a syringe by way of a variety of mechanisms known in the art such as by magnetic coupling or other methods of mechanical fitting (e.g., snap into place with tight fitting hinges or manual opening and closing of components). Syringe 400 is therefore configured to interact with sled 404 by fitting into slots in upper dock 407 and lower dock 408, as depicted in FIG. 4. Alternatively, the syringe may be placed inside of a packaging, or received at the point of care in a packaging, that has built-in features to allow the packaging itself to connect with sled 404 (e.g., the packing can be configured to interact with upper dock 407 and lower dock 408 of the sled 404; not depicted). Rails 405 of docking station 403 are adapted to allow sled 404 to be moved from a resting position in docking station 403 (as depicted in FIG. 4) to an engaged position whereby the syringe is locked in place within front chamber 406 which allows the docking station 403 to begin blending the contents of syringe 400. Docking station 403 also includes housing 411 that encloses internal blending components. Docking station 403 has a control panel 409 that can visually display a variety of operational settings and modes such as blending speed, power, mode, time remaining, slurry temperature, etc. Control panel 409 can also include buttons or a touch screen to allow a user to change the operational settings/mode. Alternatively, the settings/mode may also be changed using any method known in the art such as a remote control.

Docking station 403 may be connected to a power supply through any method known in the art. For example, docking station 403 may have a cord insertion terminal that allows connection of the docking station 403 to a wall outlet power supply via power cord 410. Docking station 403 may be configured to operate using AC power, DC power, and a combination thereof. Alternatively, or in addition, to the wall supplied power, docking station 403 may have an internal battery compartment that can hold one, two, three or more batteries. Any standard battery size may be used with the present disclosure such as 3LR12, D, C, AA, AAA, AAAA, A23, PP3, CR2032, LR44 batteries, etc. Also, any standard battery type may be used with the present disclosure such as lead acid, lithium ion, lithium polymer, nickel metal hydride, nickel cadmium, etc.

Figure 5:
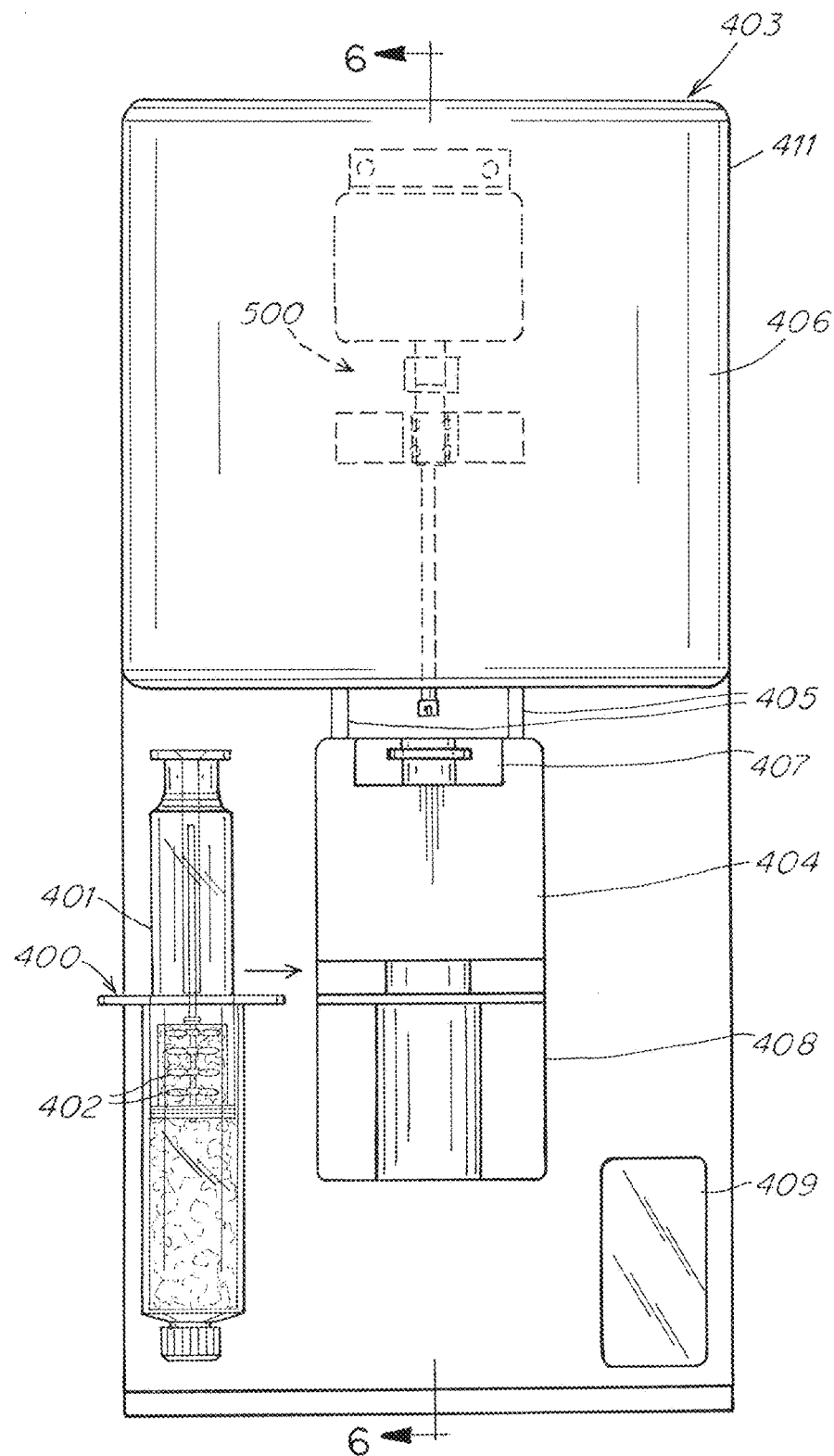
FIG. 5 is a front elevational view of a docking station configured to blend internal contents of a syringe and a syringe containing a biomaterial to be transformed into an injectable and flowable cold slurry.

FIG. 5 depicts a front elevational view of docking station 403 (as shown in FIG. 4) showing syringe 400 (having plunger 401 and blades 402) being loaded onto sled 404. The slot in upper dock 407 of sled 404 is configured to hold plunger 401 in place, while the slot in lower dock 408 is configured to hold the barrel flange of syringe 400. Once syringe 400 is secured in place, rails 405 move sled 404 upward to allow syringe 400 to engage with blending components 500 (described in more detail below) located internally within front chamber 406 within housing 411, which allows blending of the syringe's internal contents. Control panel 409 visually displays a variety of blending operation settings and modes.

Figure 6:
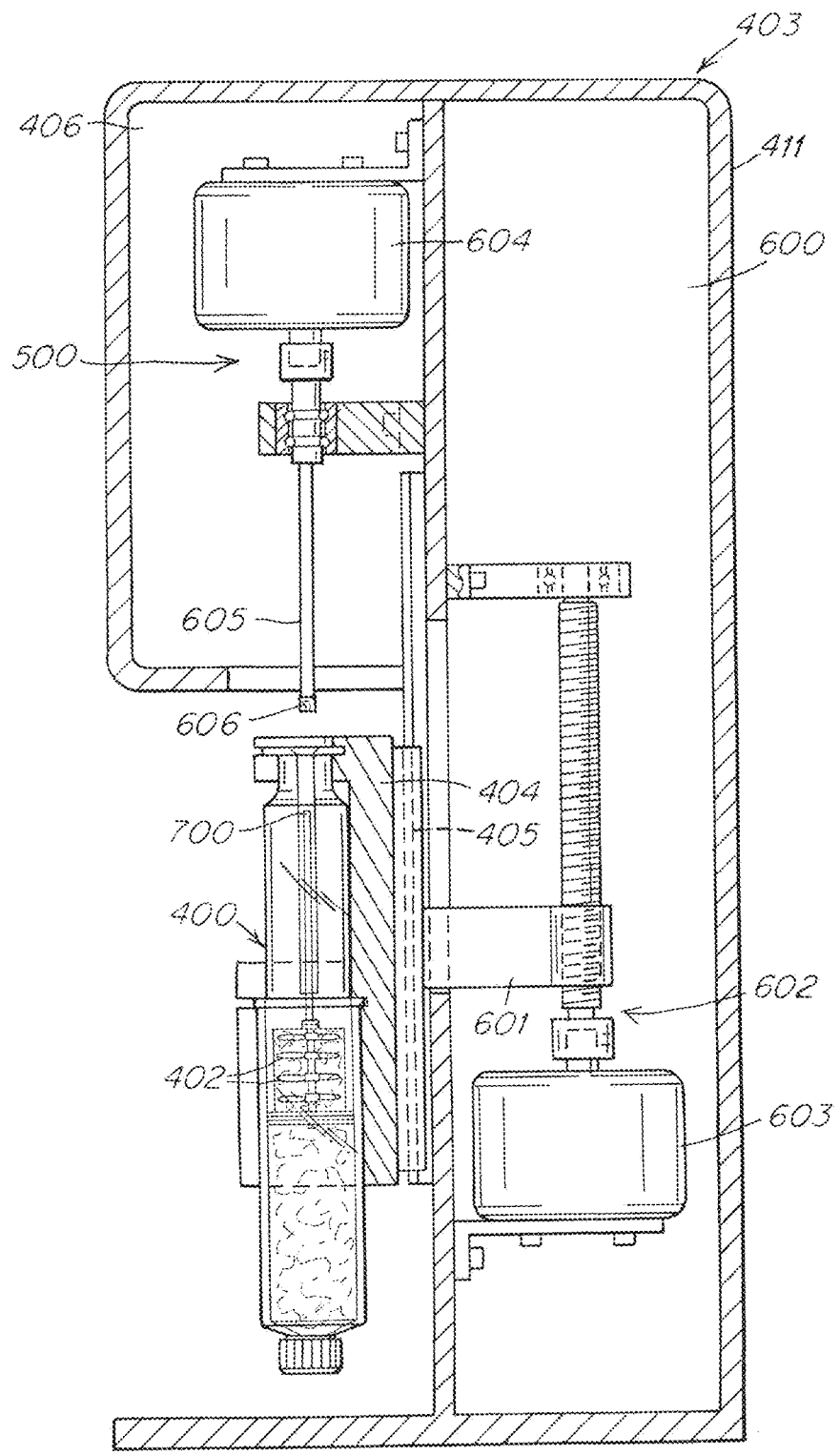
FIG. 6 is a cross-sectional side view taken along line 6-6 of FIG. 5 but with the syringe in the docked position.

Referring to FIG. 6, a cross-sectional side view of docking station 403 is illustrated with syringe 400 (having plunger 401 and blades 402) loaded onto sled 404. Sled 404 is connected to follower arm 601 which is located within back chamber 600 of docking station 403. Follower arm 601 allows sled 404 to move up and down rails 405 by engaging with leadscrew drive assembly 602. Leadscrew drive assembly 602 is in turn driven by lower brushless DC motor 603 located in the bottom portion of back chamber 600. Once sled 404 is moved to its upper-most position along rails 405, syringe 400 is ready for engagement with blending components 500 located within front chamber 406 (within housing 411). Blending components 500 are comprised of upper brushless DC motor 604 and drive shaft 605. The bottom portion of drive shaft 605 comprises male bayonet connector 606 which engages with syringe 400 through plunger 401 to allow blending of the syringe's internal contents, as described in more detail below.

Figure 7:
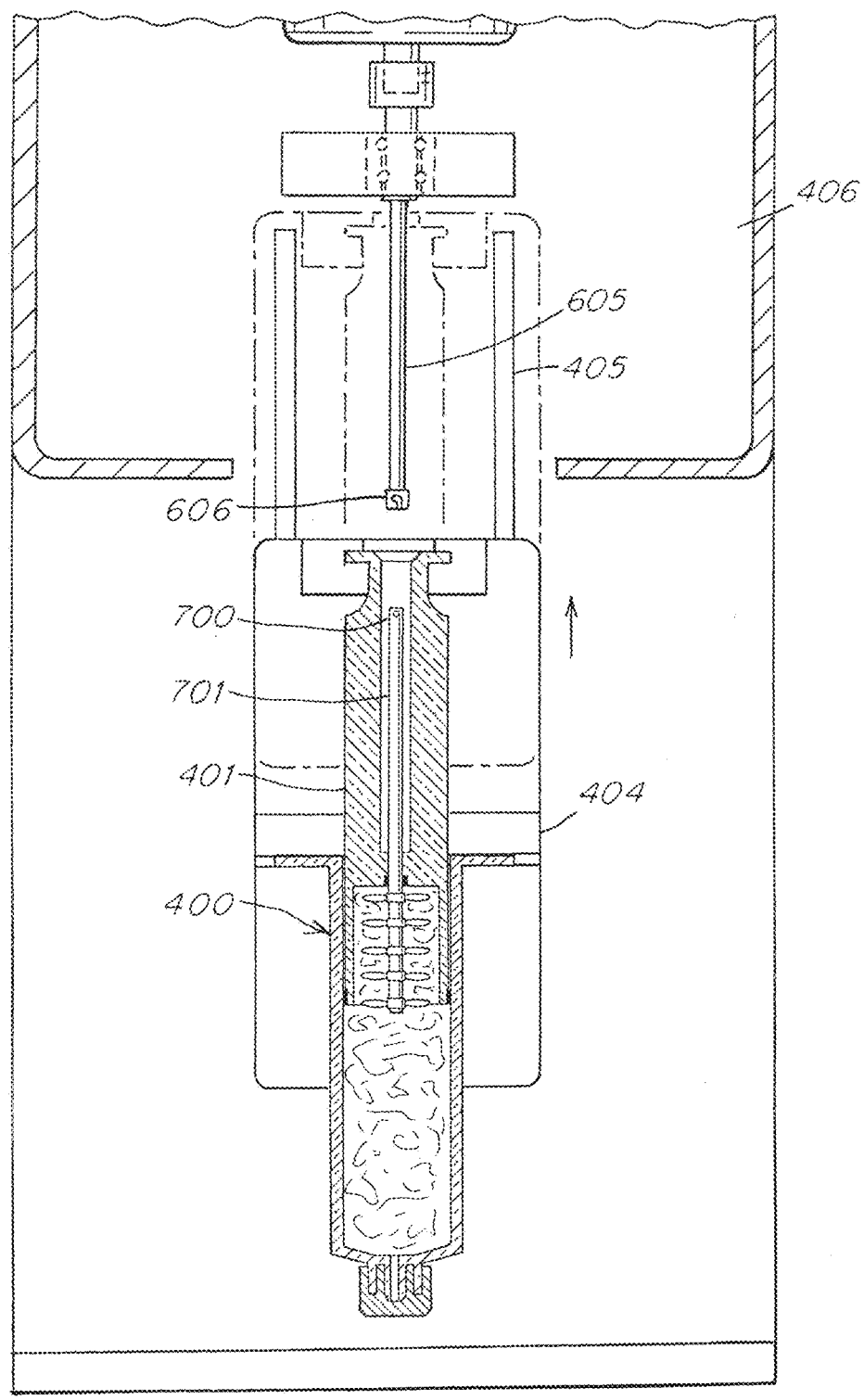
FIG. 7 is a fragmentary, partially broken away schematic front view of a portion of a docking station configured to blend internal contents of a syringe and a syringe in the docked position.

FIG. 7 depicts a fragmentary, partially broken away, front view of a portion of docking station 403 with syringe 400 docked. Sled 404 moves syringe 400 upward along rails 405 as shown to allow male bayonet connector 606 on the end of drive shaft 605 (located in front chamber 406) to connect with female bayonet connector 700 of the upper portion of blade shaft 701 (located within plunger 401). Once drive shaft 605 is engaged with blade shaft 701, the mixing or blending can be initiated to transform an internal volume of syringe 400 into an injectable and flowable slurry.

Figure 8:
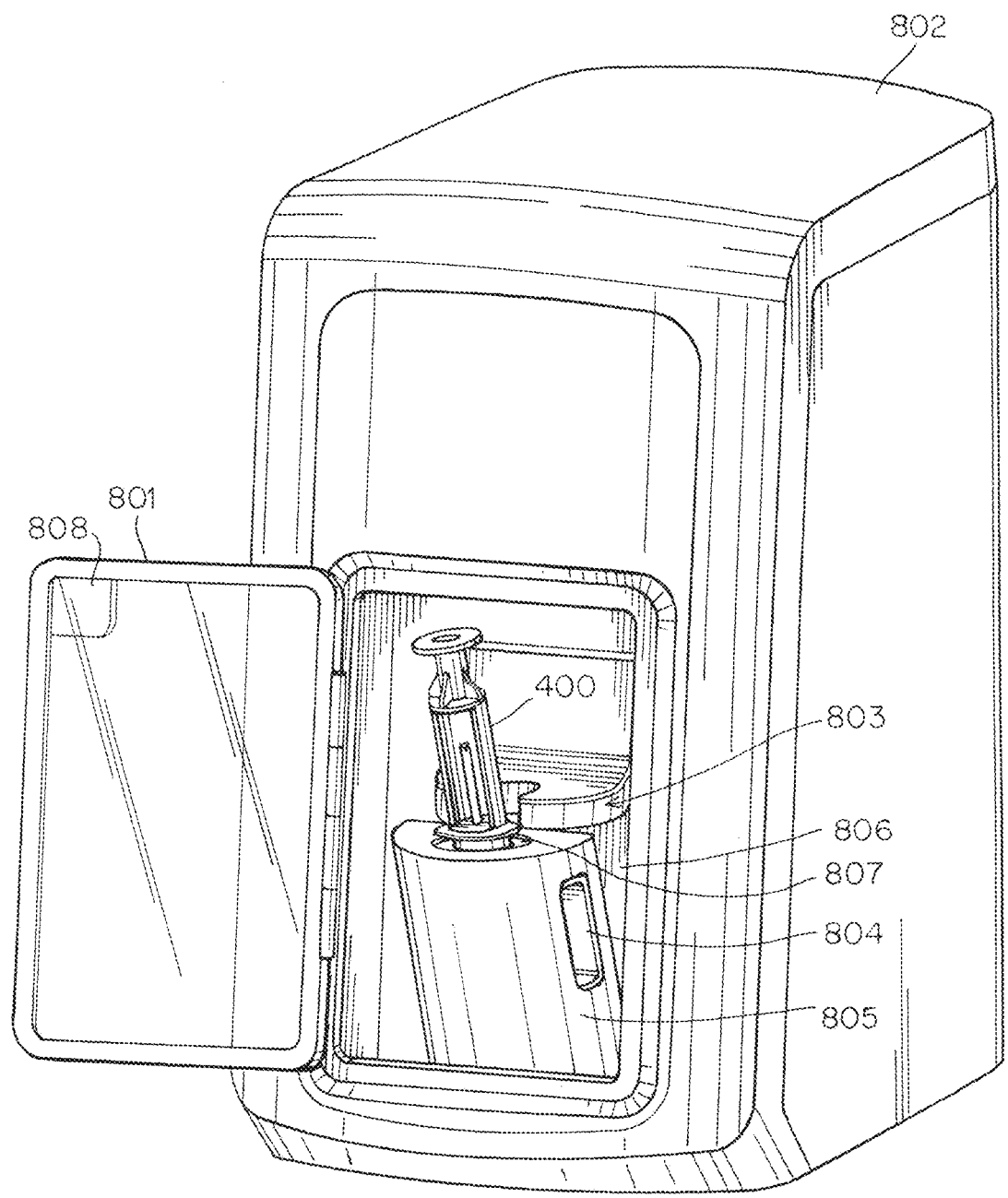
FIGS. 8-9 are perspective views of a housing surrounding a docking station configured to blend internal contents of a syringe and a syringe in the docked position, with the front holder mount in the open and closed position respectively.
Figure 9:
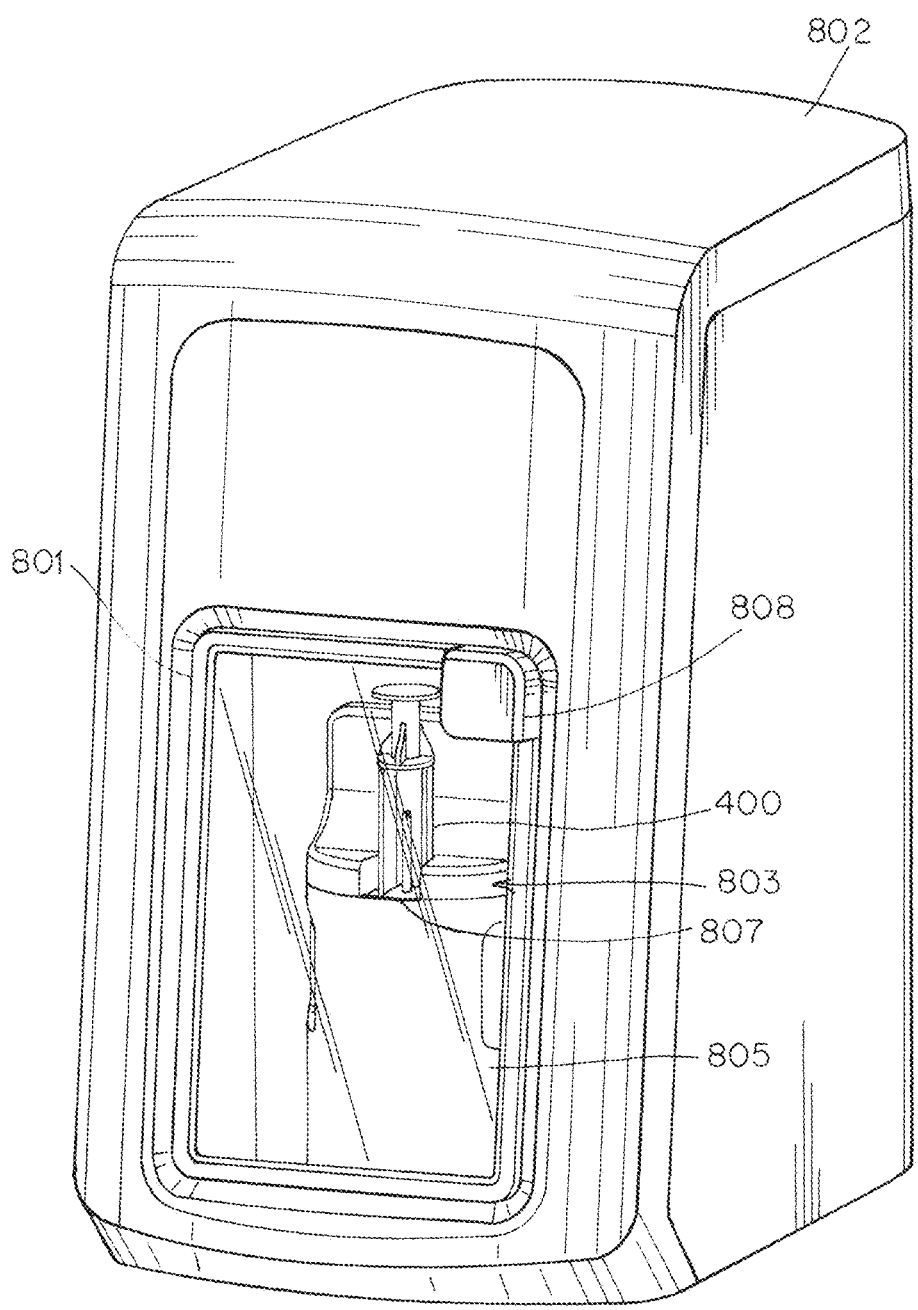

FIGS. 8 and 9 are each a perspective view of a docking station 803 located within housing 802. Housing 802 has a safety door 801 which has open and closed positions. Safety door 801 may be open and closed using door handle 808. FIG. 8 shows housing 802 with an open safety door 801. FIG. 9 shows housing 802 with a closed safety door 801. Docking station 803 has handle portion 804 which allows a user to disengage front holder mount 805 from back holder mount 806. Docking station 803 also has dock 807 which is configured to receive syringe 400. In operation, a user opens safety door 801 using door handle 808 and pulls handle portion 804 in the direction away from back holder mount 806 which causes front holder mount 805 to lower at an angle towards the user. The user then inserts syringe 400 into dock 807. The user may then push front holder mount 805 towards back chamber 806 to reengage (e.g., lock) the two holder mounts (front holder mount 805 and back holder mount 806), or the user may use handle portion 804 to move the front holder mount 805 in the direction of back holder mount 806 to reengage the two holder mounts. Then, the user closes safety door 801 as shown in FIG. 9 before initiating mixing/blending. The blending action of docking station 803 may be engaged using an LED screen (not depicted) located on safety door 801 or on housing 802. The LED screen may have various operation choices for the user to select (e.g., via touchscreen) such as ON/OFF, blending speed, blending time, and/or final desired slurry consistency. The LED screen (or safety door 801 or housing 802) may also have an LED light that indicates operational status of the syringe and docking station (e.g., see FIGS. 38-41).

Figure 10:
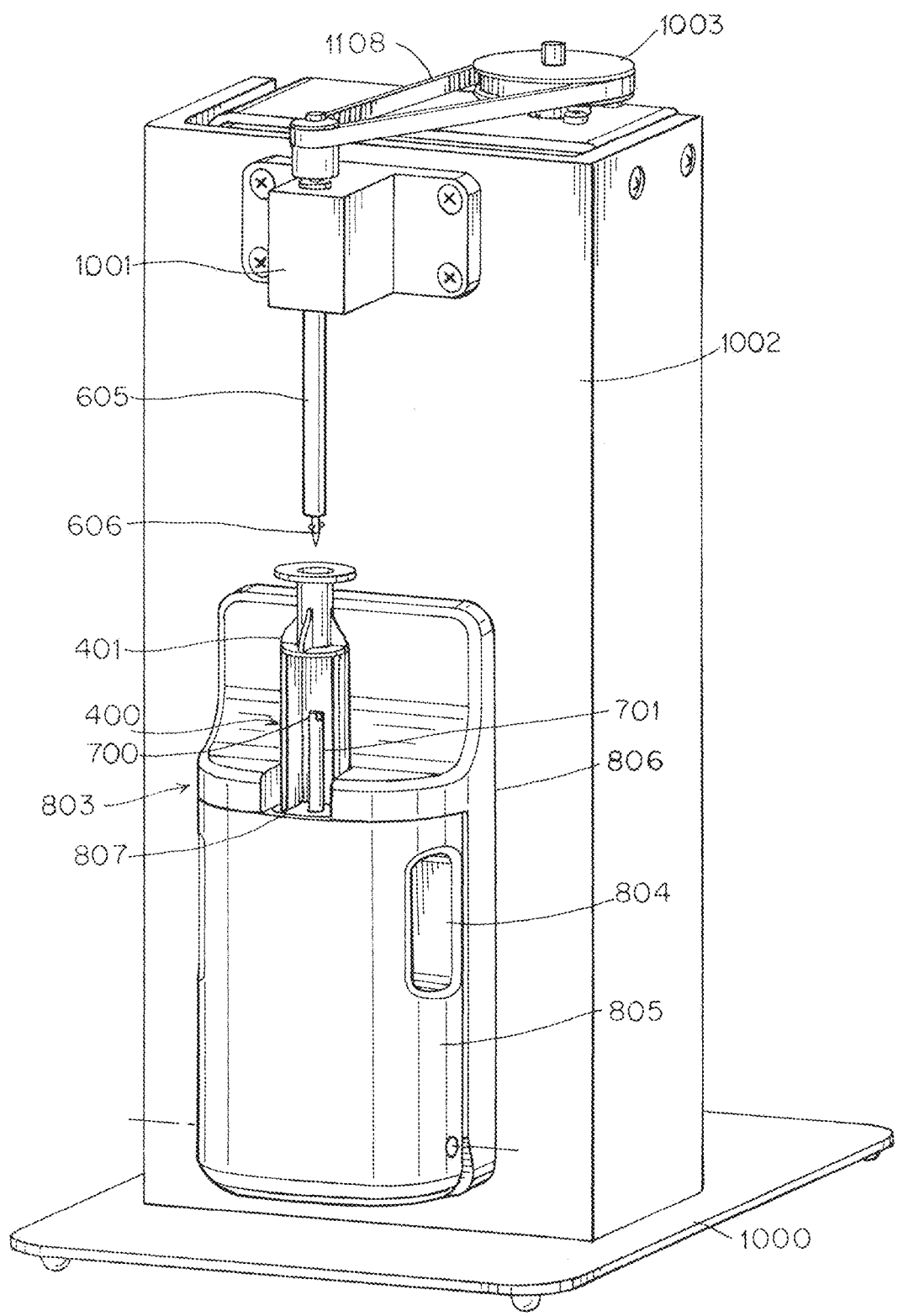
FIG. 10 is a perspective view of a docking station, a mount plate, and components configured to blend internal contents of a syringe and a syringe in the docked position, with the housing removed.

FIG. 10 depicts a perspective view of docking station 803, mount plate 1002, and a baseplate 1000. Back holder mount 806 is secured to mount plate 1002. Mount plate 1002 is a vertical mount plate that is secured to baseplate 1000 which is a horizontal plate. The components depicted in FIG. 10 may be located within a housing (not depicted; see FIGS. 8 and 9 for an example of housing 802). Front holder mount 805 of docking station 803 has handle portion 804 which allows a user to disengage front holder mount 805 from back holder mount 806. Docking station 803 also has dock 807 which is configured to receive syringe 400. Mounting block 1001 is secured to mount plate 1002 and is configured to hold drive shaft 605. The bottom portion of drive shaft 605 comprises male bayonet connector 606 which is configured to engage with female bayonet connector 700 on blade shaft 701 of plunger 401 to activate the blending functionality of the docking station via spindle pulley 1003 and spindle belt 1108 (as described in greater detail below).

Figure 11:
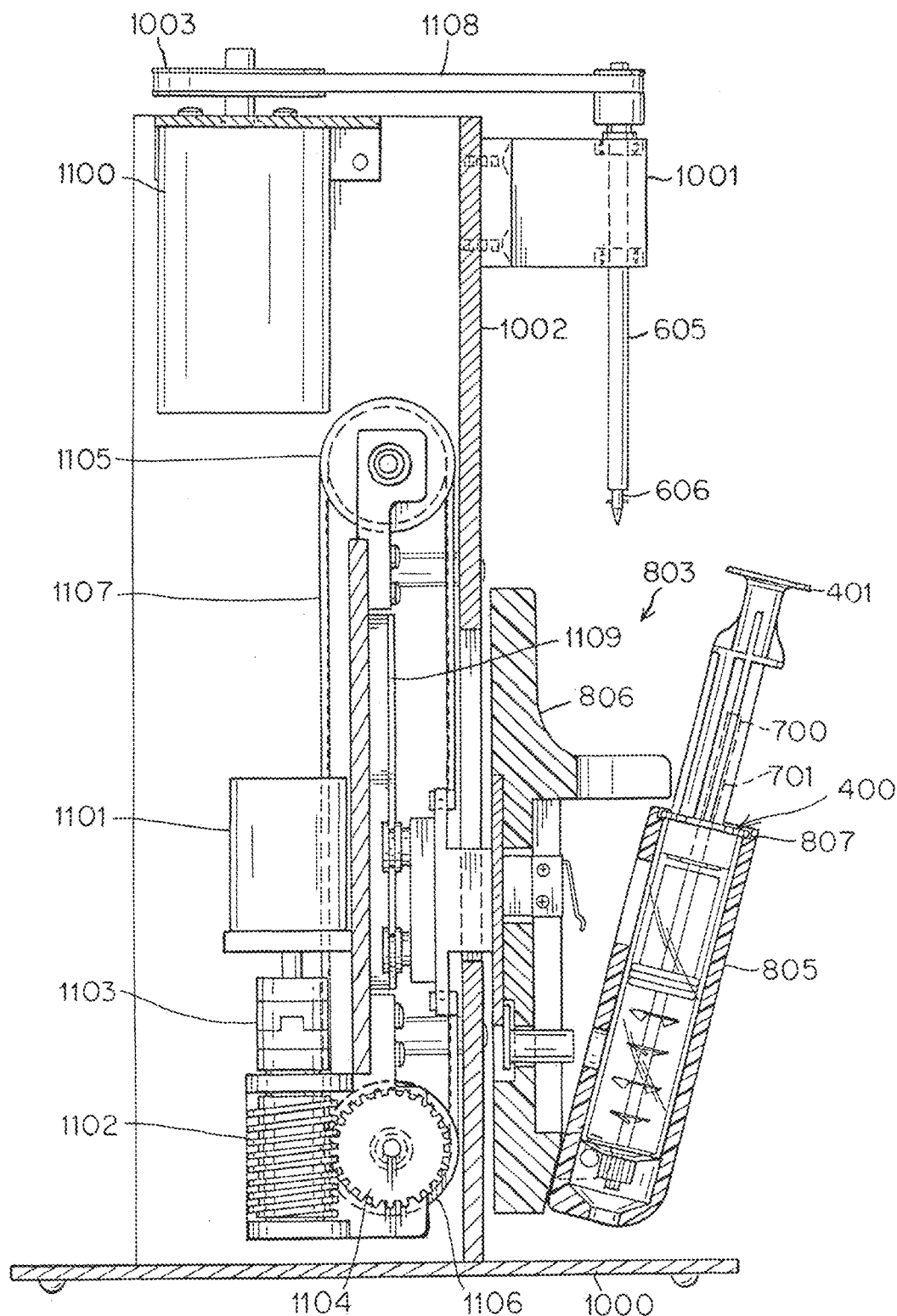
FIGS. 11-13 are cross-sectional side views of the docking station, mount plate, and components of FIG. 10, configured to blend internal contents of a syringe and a syringe in the prior to loading, blending, and after blending positions respectively.
Figure 12:
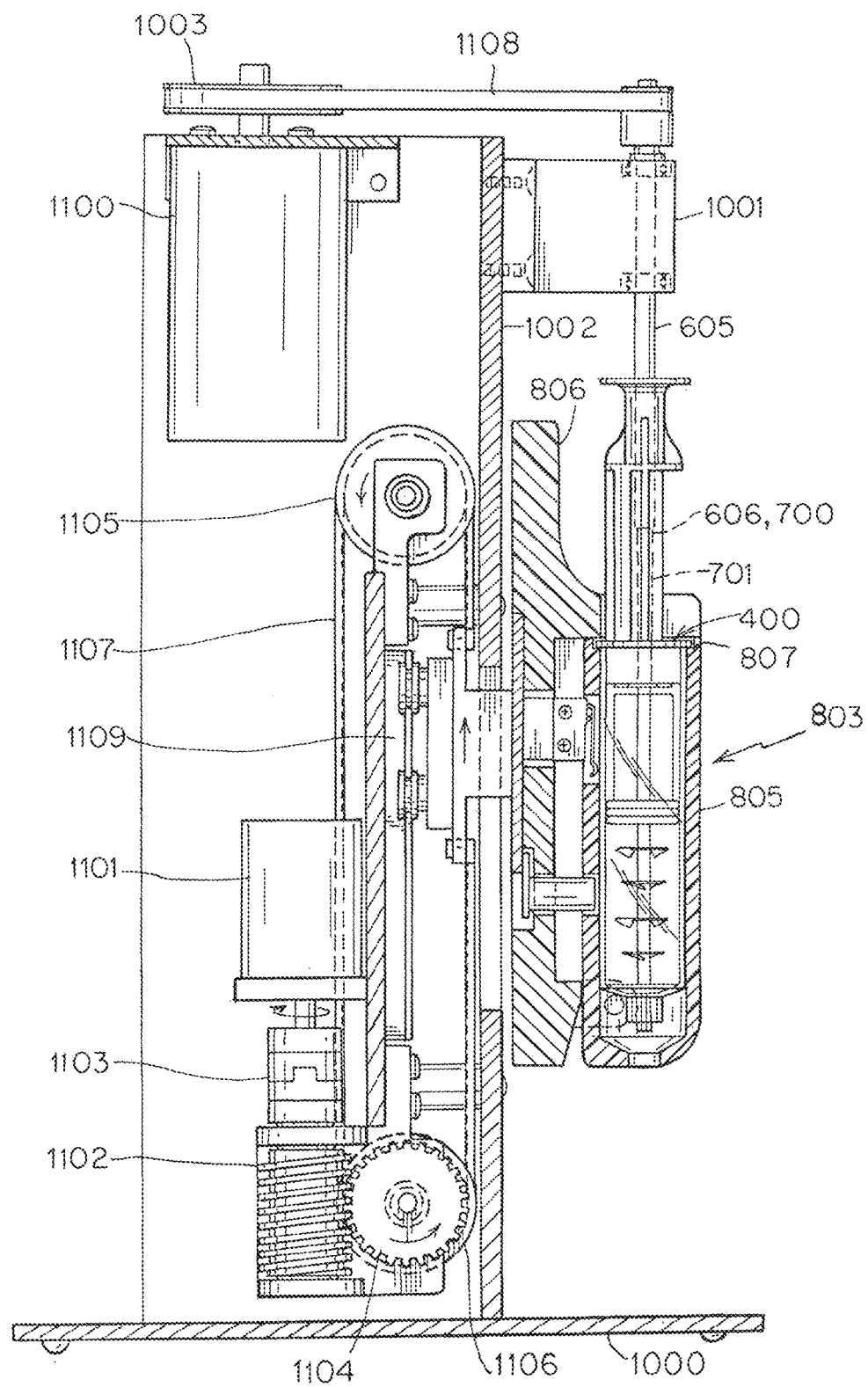
Figure 13:
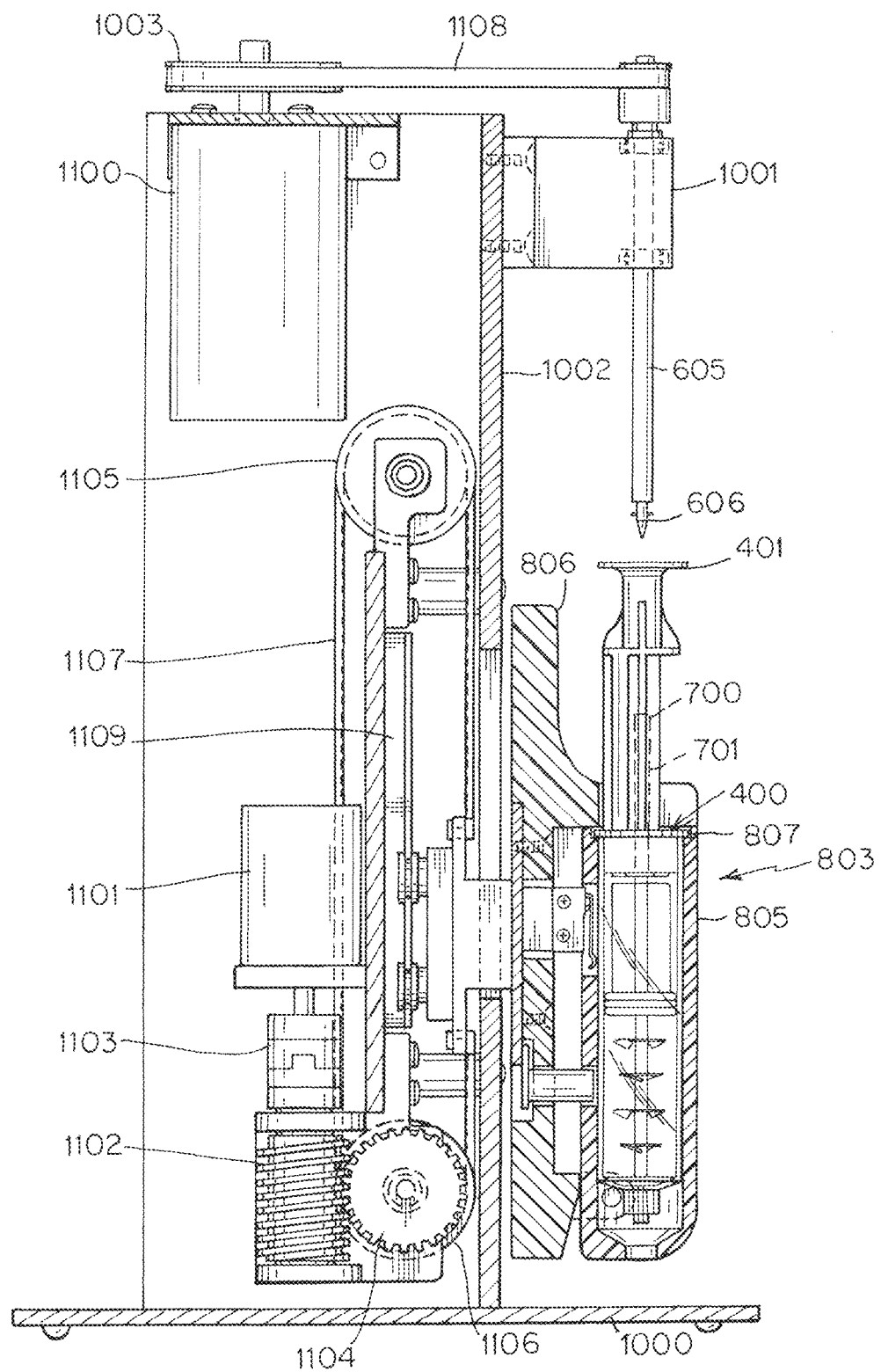

FIGS. 11-13 depict a cross-sectional side view of docking station 803, mount plate 1002, baseplate 1000, and various components that drive the blending of the syringe's internal contents. FIG. 11 depicts syringe 400 within dock 807, with front holder mount 805 in its downward (e.g., open and/or unlocked) position. The downward position allows dock 807 to receive syringe 400. FIGS. 12 and 13 show syringe 400 in dock 807 with front holder mount 805 in its upward (e.g., closed and/or locked) position. Referring to FIGS. 11-13, a brushless DC motor 1101 is located above helical shaft 1103 and worm 1102. Worm 1102 engages a worm gear 1104. Worm gear 1104 is connected axially to a lower timing pulley 1106. Lower timing pulley 1106 is configured to interact with upper timing pulley 1105 via stepper belt 1107. When active, brushless DC motor 1101 rotates worm 1102 via shaft 1103 (see FIG. 12). The rotation of worm 1102 causes rotation of worm gear 1104. The rotation of worm gear 1104 in turn causes rotation of lower timing pulley 1106 and upper timing pulley 1105. Rotation of lower timing pulley 1106 and upper timing pulley 1105 moves stepper belt 1107 such that back holder mount 806 (which can also be referred to as a sled) moves upward along rails 1109 towards spindle motor 1100. Movement of back holder mount 806 (or sled) towards spindle motor 1100 allows male bayonet connector 606 on lower portion of drive shaft 605 to connect with female bayonet connector 700 of the upper portion of blade shaft 701 located within plunger 401 of syringe 400. Mounting block 1001 is secured to mount plate 1002 and is configured to hold drive shaft 605. Once the blade shaft 701 and drive shaft 605 are engaged (see FIG. 12), the blending functionality of the docking station can be initiated by activating a spindle motor 1100. Spindle motor 1100 revolves to cause rotation of spindle pulley 1003 which is attached to drive shaft 605 via a spindle belt 1108. Spindle pulley 1003 rotates and thereby causes rotation of drive shaft 605 to initiate blending of the internal contents of syringe 400 via blade shaft 701 and attached blades 402. Once blending is complete, back holder mount 806 (or sled) moves downward along rails 1109 away from spindle motor 1100 to disengage male bayonet connector 606 on lower portion of drive shaft 605 from female bayonet connector 700 of the upper portion of blade shaft 701. The user may then place front holder mount 805 back to its downward (e.g., open and/or unlocked) position (see FIG. 11) and retrieve syringe 400 having cold slurry ready for injection into a patient at a target location.

Figure 14:
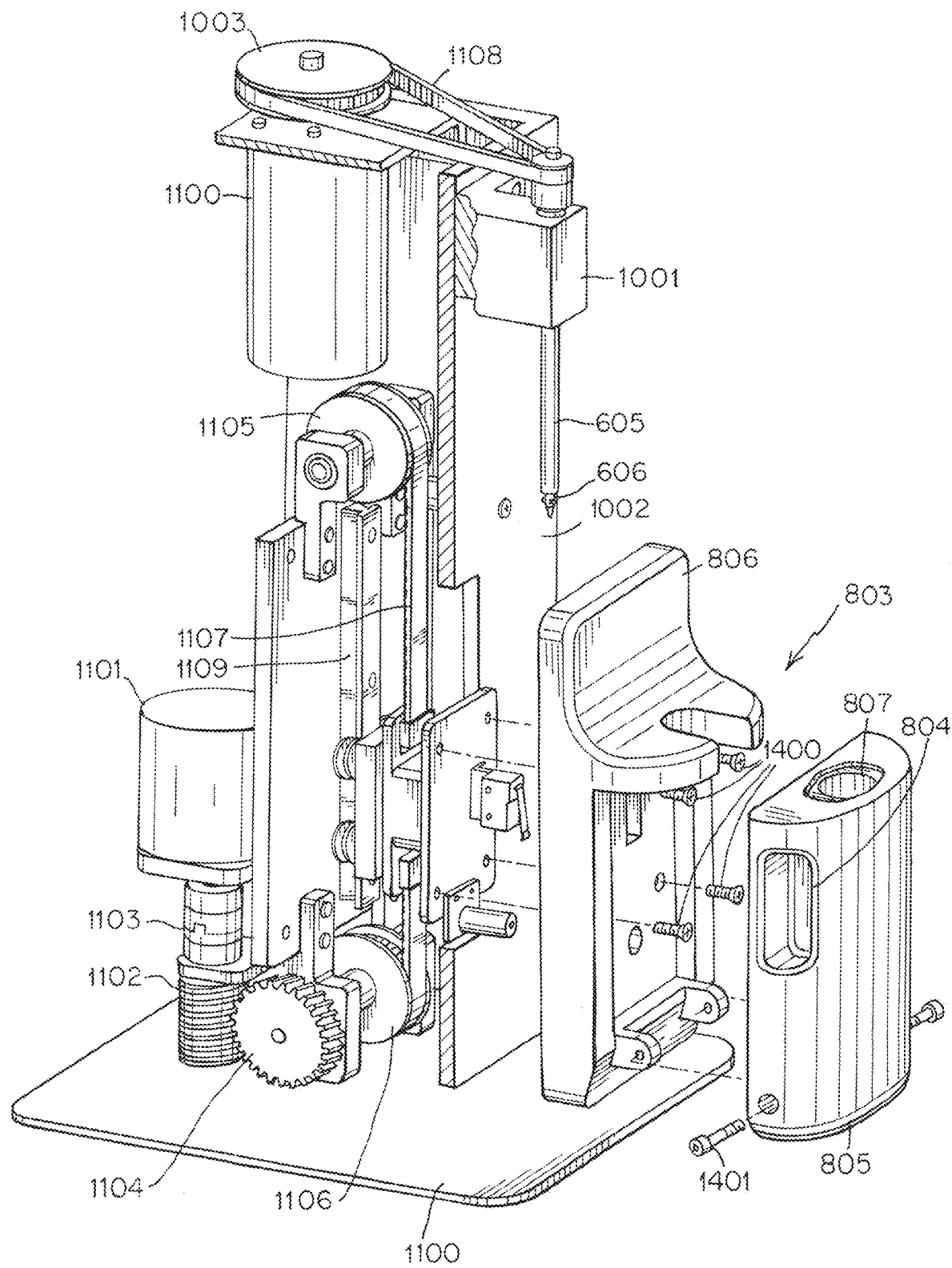
FIG. 14 is an exploded perspective view of the docking station, mount plate, and components of FIGS. 10-13 configured to blend internal contents of a syringe.

FIG. 14 is an exploded perspective view of docking station 803, mount plate 1002, baseplate 1000, and various components that drive the blending of the internal syringe contents. Baseplate 1000 is configured to hold the various components of docking station 803 (such as back holder mount 806), mount plate 1002, and worm 1102. Back holder mount 806 is secured to mount plate 1002 with a plurality of machine screws 1400. Front holder mount 805 is secured to back holder mount 806 with a plurality of screws 1400. Additionally, two shoulder screws 1401 allow front holder mount 805 to rotationally pivot around a horizontal axis from a closed (or locked) position (see FIG. 12) to an open (or unlocked) position (see FIG. 11). A user can move front holder mount 805 from a closed to an open position and from an open to a closed position using handle portion 804. A brushless DC motor 1101 is located above helical shaft 1103 and worm 1102. Worm 1102 engages worm gear 1104. Worm gear 1104 is connected axially to lower timing pulley 1106. Lower timing pulley 1106 is configured to interact with upper timing pulley 1105 via timing belt 1107. When active, brushless DC motor 1101 rotates worm 1102 via shaft 1103. The rotation of worm 1102 causes rotation of worm gear 1104. The rotation of worm gear 1104 in turn causes rotation of lower timing pulley 1106 and upper timing pulley 1105. Rotation of lower timing pulley 1106 and upper timing pulley 1105 moves timing belt 1107 such that back holder mount 806 (which can also be referred to as a sled) moves upward along rails 1109 towards spindle motor 1100. Movement of back holder mount 806 (or sled) towards spindle motor 1100 allows male bayonet connector 606 on lower portion of drive shaft 605 to connect with female bayonet connector 700 (not depicted, see FIGS. 11-13) of the upper portion of blade shaft 701 located within plunger 401 of syringe 400 (not depicted, see FIGS. 11-13). Mounting block 1001 is secured to mount plate 1002 and is configured to hold drive shaft 605. Once blade shaft 701 and drive shaft 605 are engaged (see FIG. 13), the docking station's blending functionality can be initiated by activating a spindle motor 1100. Spindle motor 1100 revolves to cause rotation of spindle pulley 1003 which is attached to drive shaft 605 via a spindle belt 1108. Spindle pulley 1003 rotates and thereby causes rotation of drive shaft 605 to initiate blending of the internal contents of syringe 400 via blade shaft 701 and attached blades 402 (not depicted, see FIGS. 11-13).

Figures 15A, 15B, 15C:
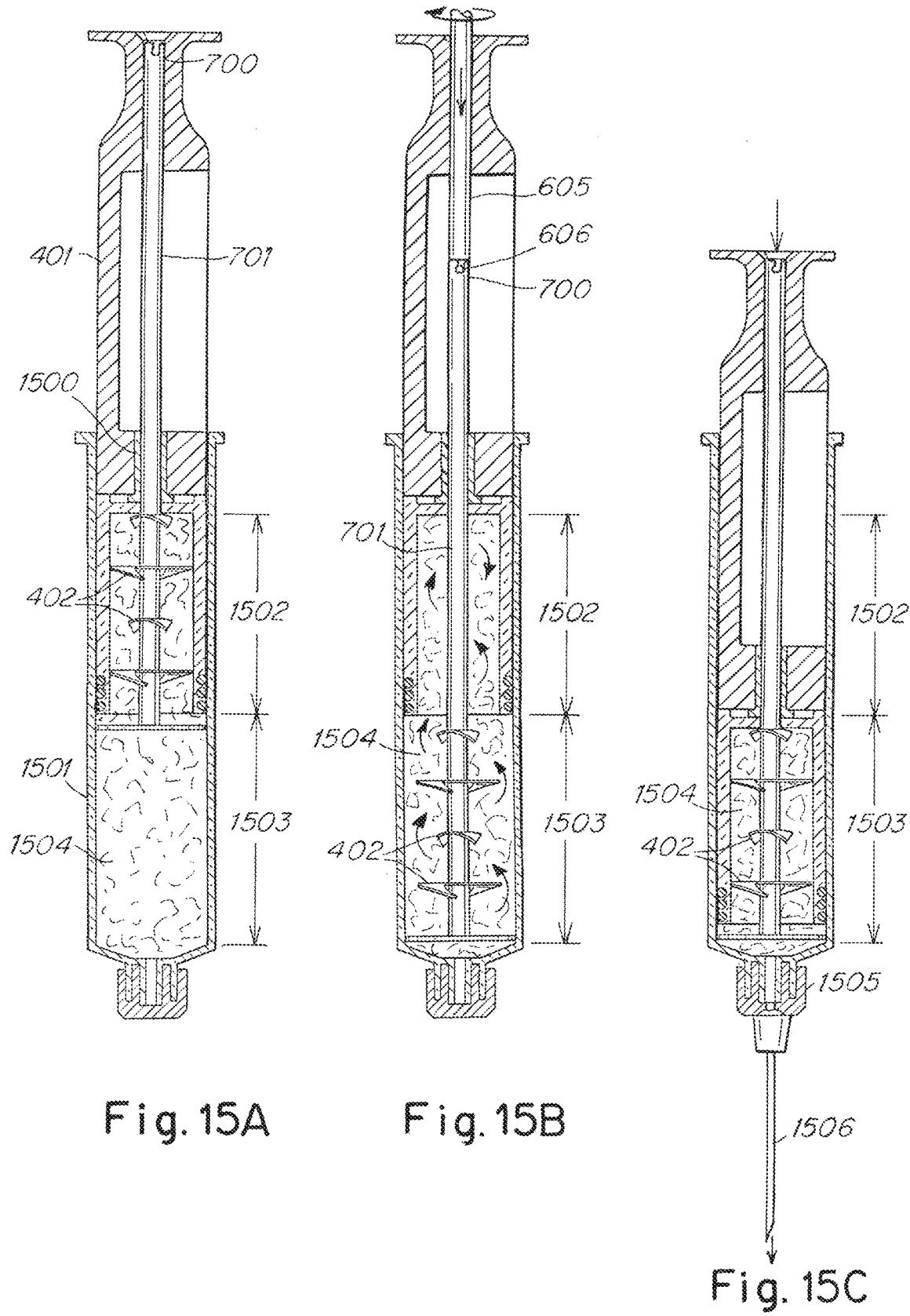
FIGS. 15A-C are side cross-sectional views of a syringe with internal blades configured to blend internal syringe contents.

FIGS. 15A-C depicts a syringe adapted for engaging with a docking station (not depicted) to cause blending for creating an injectable cold slurry. FIG. 15A depicts a syringe showing female bayonet connector 700 located within plunger 401. Male bayonet connector 606 is configured to interact with female bayonet connector 700 (see FIG. 7) to cause the blade shaft 701 and attached blades 402 to spin and therefore cause blending of the syringe's internal contents. Sterility seals 1500 maintain the sterility of the internal syringe environment inside syringe barrel 1501. Therefore, the composition to be transformed into an injectable and flowable cold slurry may be placed inside the syringe prior to shipping the syringe to the point of care and sterility will be maintained throughout shipping and preparation of the injectable and flowable cold slurry. Sterility seals 1500 may be comprised of any suitable material known in the art such as aluminum, low-density polyethylene, polypropylene, polystyrene, polyvinylidine chloride, nylon, metalized film, ethylenevinyl alcohol, ethyleneacrylic acid, and a combination thereof. FIG. 15A shows pre-blend zone 1502 and blend zone 1503. In FIG. 15A, blades 402, attached to blade shaft 701, are positioned within pre-blend zone 1502. FIGS. 15B and 15C show blades 402 advanced into blend zone 1503 which occurs when syringe 400 is engaged with a docking station which has been activated for the purpose of blending. Syringe 400 has a female bayonet connector 700 on blade shaft 701 located within plunger 401 which is adapted to engage with male bayonet connector 606 located at the bottom of drive shaft 605 (see FIG. 7). Drive shaft 605 is part of a docking station (not depicted). The use of male and female bayonet connectors is exemplary, and any known method of connecting components for electrical conduction can be used to connect the syringe with an external docking station.

When blades 402 are advanced into blend zone 1503, an active power source supplied by or through a docking station allows for the blades to spin to cause blending of the internal syringe 400 contents to create slurry 1504, as depicted in FIG. 15B. Blades 402 may spin at any rate suitable for causing blending of a solution to form an injectable cold slurry such as 1,000 to 5,000 RPM, 5,000 to 10,000 RPM, 10,000 to 15,000 RPM, 15,000 to 20,000 RPM, 20,000 to 25,000 RPM, 25,000 to 30,000 RPM, or faster than 30,000 RPM. The more crystallized the state of the internal syringe contents (i.e., frozen), the faster the blending speed required to form an injectable cold slurry. The docking station may also be adapted to provide for various settings with a plurality of blade spin speeds. After blending is complete and syringe 400 is disengaged from the docking station, plunger 401 is advanced into blend zone 1503 as shown in FIG. 15C. This causes slurry 1504 to travel through syringe tip 1505 into and out of syringe needle 1506, while blades 402 remain positioned in blend zone 1503. Plunger 401 will be advanced into blend zone 1503 for the purpose of injecting a patient with cold slurry at a target location.

Blades 402 are depicted as being composed of four blade rows along blade shaft 701 and are configured in rows along the longitudinal portion of the syringe, with two blades in the horizontal plane on each row. However, any number of blade rows can be used with the present disclosure such as one row of blades, two rows of blades, three rows of blades, or more than three rows of blades. Any spacing between blade rows may be used such that the total blade compartment distance along the longitudinal axis of the syringe (without considering the plunger length) may comprise less than about 10% of the total syringe length, between about 10% and 20% of the total syringe length, between about 20% and 30% of the total syringe length, or more than about 30% of the total syringe length. Furthermore, any number of blades can be arranged in the horizontal plane of the syringe on each row including a single blade, two blades (e.g., as depicted in FIGS. 15 A-C), three blades, or more than three blades. The blades may also be comprised of any shape and of any sharpness level known in the art. All blades within a given syringe may be comprised of the same size or may be comprised of more than one size (e.g., FIGS. 15A-C shows two of four blades having a shorter length). Blades 402 are configured to be placed within the syringe such that the blades do not touch the walls of the syringe, including when the blades are spinning. In some embodiments, a distal blade 1801 (see FIG. 18) can further be included to minimize vibrations during blending and to prevent blades 402 from touching the walls of the syringe.

Figure 16:
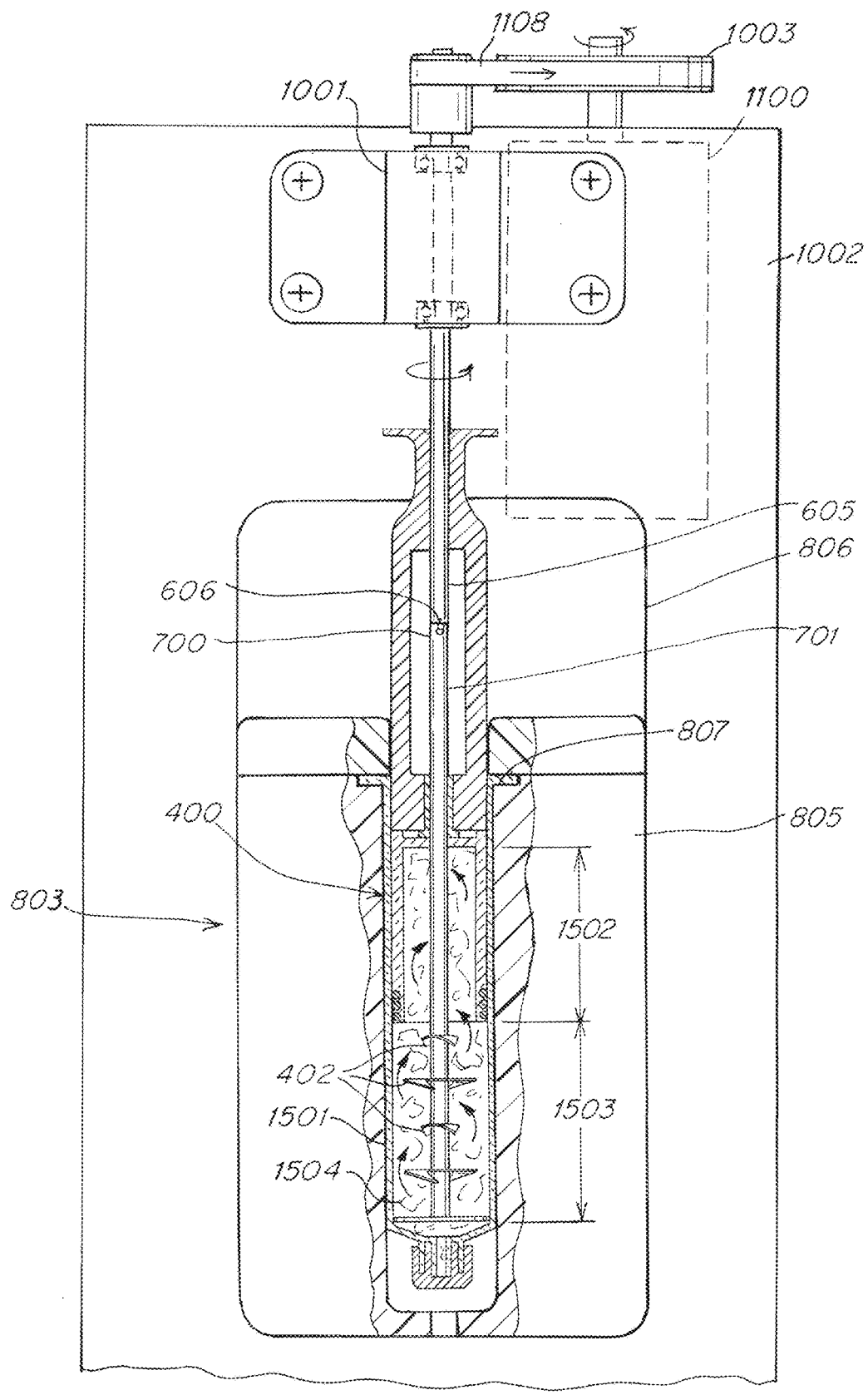
FIG. 16 is fragmentary and partially broken away schematic front view of the docking station of FIG. 14 configured to blend internal contents of a syringe and a syringe during blending mode.

FIG. 16 depicts a fragmentary and partially broken away view of a portion of a docking station 803 and mount plate 1002 with syringe 400 docked and ready for blending. Back holder mount 806 and mounting block 1001 (which holds drive shaft 605) are secured to mount plate 1002. In one embodiment, back holder mount 806 (or sled 404, e.g., see FIG. 4) travels up toward drive shaft 605 while spindle motor 1100 begins to spin, causing rotation of spindle pulley 1003 which in turn moves spindle belt 1108. The rotation of spindle pulley 1003 causes rotation of drive shaft 605 (via spindle belt 1108). The rotational speed ensures smooth engagement and secure locking of male bayonet connector 606 (of drive shaft 605) with female bayonet connector 700 (of blade shaft 701). Drive shaft 605 may be connected with blade shaft 701 through a variety of possible shaft connections known in the art such as beam coupling, bellows coupling, disc coupling, diaphragm coupling, clamp coupling, gear coupling, bushed pin coupling, elastic coupling, elastomer coupling, flexible coupling, Geislinger coupling, Oldham coupling, magnetic coupling, grid coupling, constant velocity coupling, donut coupling, Hirth joint coupling, sleeve coupling, tapered shaft lock coupling, twin spring coupling, rag joint coupling, universal joint coupling, etc. Once such a connection is established, blade shaft 701 (connected to drive shaft 605) is lowered from pre-blend zone 1502 toward blend zone 1503 inside syringe barrel 1501. Spindle motor 1100 is now ready for operation at maximum speed (or lower available speed options) to cause rotation of drive shaft 605 which in turn causes rotation of blades 402 for creation of slurry 1504 of a desired consistency. In any embodiments described herein, upper brushless DC motor 604 (see FIG. 6) can be used in place of spindle motor 1100 to effectuate rotation of drive shaft 605 which will lead to blending of the contents of syringe 400.

Figure 17:
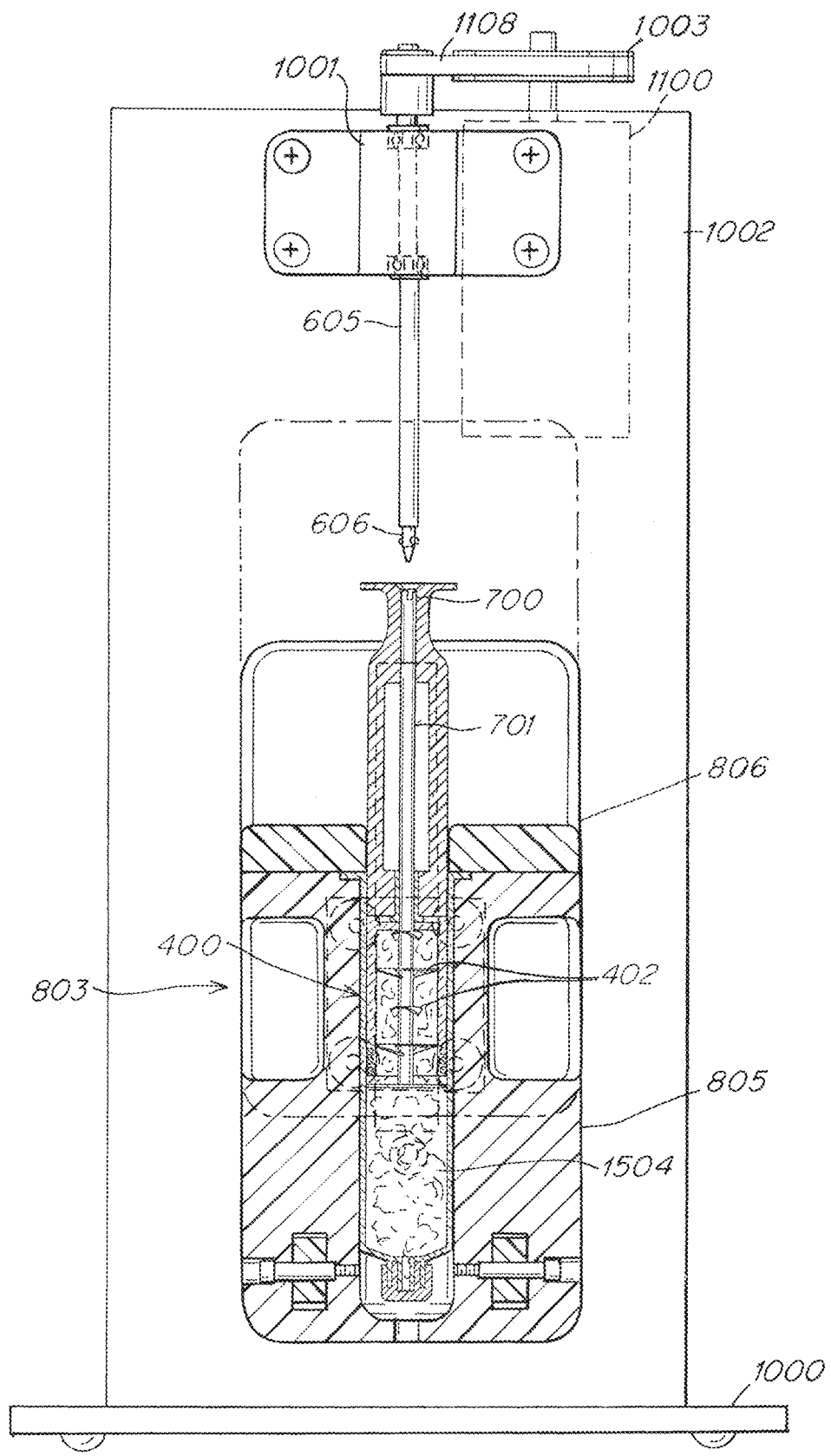
FIG. 17 is a schematic view similar to FIG. 16 but with the syringe ready for removal after completion of blending.

FIG. 17 depicts a portion of docking station 803, mount plate 1002, and baseplate 1000 with syringe 400 ready for removal. Once blending is complete, spindle motor 1100 ceases rotation of spindle pulley 1003 which in turn ceases movement of spindle belt 1108 and drive shaft 605 no longer rotates. This is followed by a slow speed rotation of spindle motor 1100 in a reversed rotational direction from the blending direction which in turn slowly rotates spindle pulley 1003 and moves spindle belt 1108 in the reverse direction from the direction of blending. This causes drive shaft 605 to also rotate in a reversed rotational direction from the blending direction in order to cause disengagement of male bayonet connector 606 from female bayonet connector 700. Alternatively, drive shaft 605 (held by mounting block 1001) can be rotated in the reversed direction simultaneously with lowering of back holder mount 806 (or sled 404, see FIG. 6) which moves along rails 1109 (or rails 405, see FIG. 6). After disengagement, drive shaft 605 is no longer connected to blade shaft 701. Back holder mount 806 (or sled 404, see FIG. 6) is then lowered completely to its ready position and front holder mount 805 can be opened (see FIG. 11) for removal of syringe 400 from docking station 803 for use of slurry 1504.

Docking station 803 may be connected to a power supply through any method known in the art. For example, docking station 803 may have a cord insertion terminal that allows connection of the docking station 803 to a wall outlet power supply via a power cord. The housing 802 (see FIGS. 8 and 9) may have an opening for the power supply cord to allow the power supply cord to run from docking station 803 to a wall outlet. Docking station 803 may be configured to operate using AC power, DC power, and a combination thereof. Alternatively, or in addition, to the wall supplied power, docking station 803 may have an internal battery compartment that can hold one, two, three or more batteries. Any standard battery size may be used with the present disclosure such as 3LR12, D, C, AA, AAA, AAAA, A23, PP3, CR2032, LR44 batteries, etc. Also, any standard battery type may be used with the present disclosure such as lead acid, lithium ion, lithium polymer, nickel metal hydride, nickel cadmium, etc.

Figure 18:
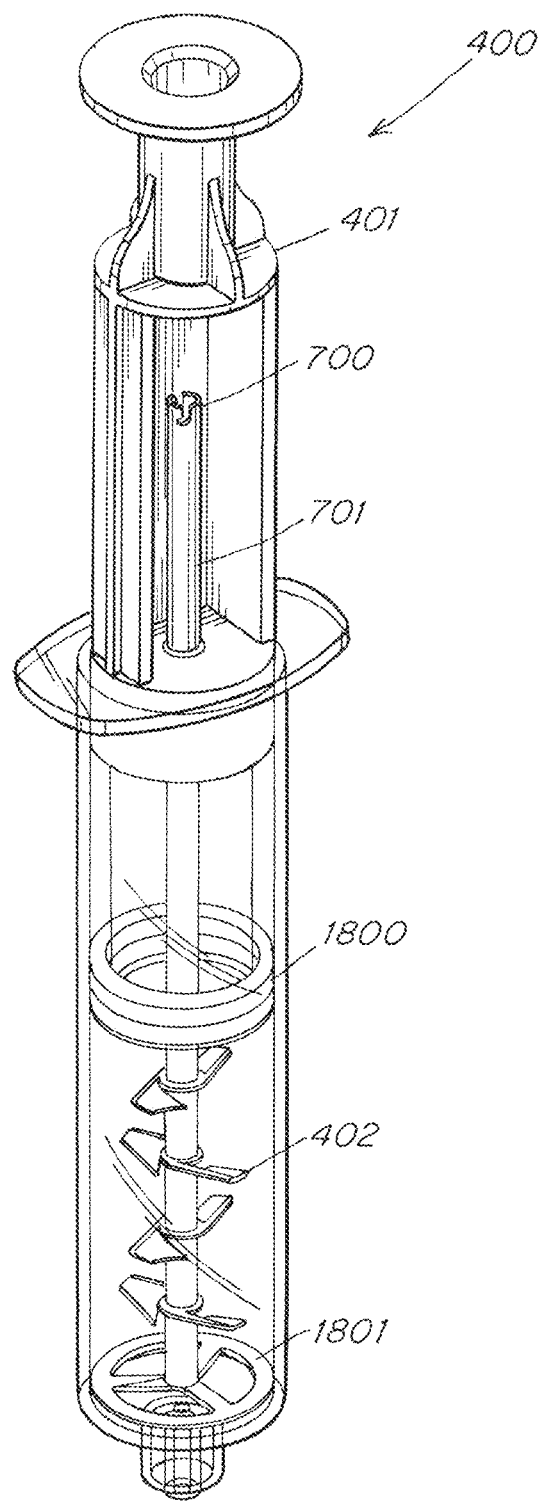
FIG. 18 is a perspective view of a syringe with internal blades configured to blend internal syringe contents.

FIG. 18 is a perspective view of syringe 400 having a plunger 401, blade shaft 701 (including female bayonet connector 700), and blades 402. Blades 402 are designed to generate appropriate flow and chop for creating an injectable and flowable cold slurry. In some embodiments, blades 402 are able to generate significant flow while simultaneously effectively chopping crystallized solution due to the arrangement of the blades being oriented at different points around the center longitudinal axis of the syringe (e.g., one set of two blades is oriented east-west and a different set of two blades is oriented north-south; two rows are at a 90° offset from the other two rows), as depicted in FIG. 18. One or more leading edges of blades 402 is configured to be sharp. In some embodiments, syringe 400 also includes distal blade 1801. Distal blade 1801 provides added stability, by providing a second bearing surface, to prevent or reduce the impacts of resonance caused by certain frequencies of rotations of the blade shaft 701 during blending. The excessive vibration can occur due to natural frequency changes while blade shaft 701 moves up and down vertically during mixing when engaged with a drive shaft of a docking station (e.g., see FIG. 16). Distal blade 1801 also has slots which allow for mixing of the contents of syringe 400 at the distal end. In some embodiments, distal blade 1801 is also formed of a smooth material (e.g., smooth metal) to prevent particulate generation within the internal volume of syringe 400. In some embodiments, syringe 400 also has O-rings 1800 that provide added pressure to the end of plunger 401 to facilitate ejection of cold slurry through the tip of syringe 400.

Plunger 401 can have a partially hollow interior suited to accept blade shaft 701. Additionally, plunger 401 can be hollow and long enough longitudinally such that when plunger 401 is pushed down (towards the tip of syringe 400), blades 402 fully retract into the hollow portion of plunger 401. This allows for a substantial percentage of the internal volume of the syringe (e.g., cold slurry) to be ejected from syringe 400. In some embodiments, between about 60% and about 70%, between about 70% and 80%, or more than about 80% of the cold slurry inside of syringe 400 can be ejected when plunger 401 is pushed maximally toward the tip of syringe 400. In some embodiments, when plunger 401 is pushed maximally toward the tip of syringe 400, distal blade 1801 contacts and engages with O-rings 1800, such that O-rings 1800 provide pressure to hold distal blade 1800. This allows for plunger 401 to be retracted (i.e., moved upward away from the tip of syringe 400), together with blades 402 and distal blade 1801. Therefore, when plunger 401 is pushed down fully to its maximal position, plunger 401 engages with distal blade 1801 allowing a user to then retract (move upward, away from the syringe tip) plunger 401 together with blade shaft 701 (to which blades 402 and distal blade 1801 are attached). However, during blending of the internal syringe volume, plunger 401 is kept at a fixed vertical position (e.g., see FIG. 16), which allows for a drive shaft (e.g., see FIG. 16, drive shaft 605) to move blade shaft 701 (and thus blades 402 and distal blade 1801) up and down longitudinally (vertically), independently of plunger 401.

Blades 402, distal blade 1801, and O-rings 1800, as depicted in FIG. 18, can be sealed within the barrel of syringe 400 and syringe 400 can be sterilized as a whole (with all of its components as shown in FIG. 18), to prevent breaking the sterile barrier of syringe 400. Syringe 400 can also include sterility seals (see FIGS. 15A-C, sterility seals 1500) that seal the internal components of syringe 400 (e.g., blades 402, distal blade 1801, and O-rings 1800) within the sterile barrier. In some embodiments, syringe 400 is disposable after a single use to maintain sterility of syringe 400 for each patient.

Figure 19:
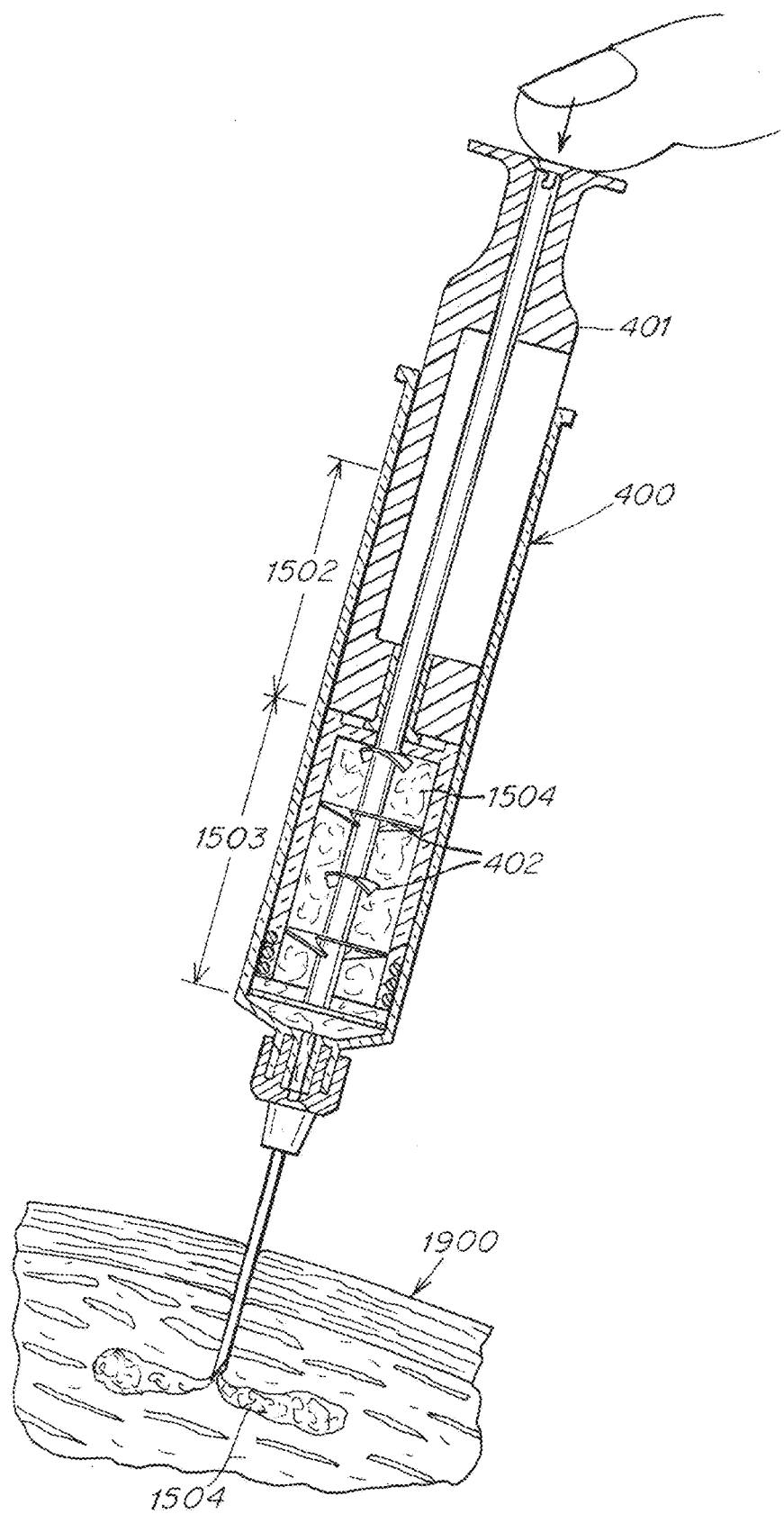
FIG. 19 is a cross-sectional side view of a syringe with the syringe contents being injected into a subject.

FIG. 19 shows syringe 400 after blending is completed, containing slurry 1504 ready for use in a patient 1900. Plunger 401 is pushed (e.g., with a thumb, a different finger, or with a medical device), which causes injection of slurry 1504 into patient 1900. In some embodiments, after removal from the docking station, syringe 400 is subjected to other techniques for preparing an injectable slurry prior to injection such as thawing, further freezing, manual shaking, magnetic agitation, etc. In some embodiments, blades 402 are lowered from pre-blend zone 1502 into blend zone 1503 during lowering of plunger 401 for injection. In some embodiments, a certain percentage of slurry 1504 remains inside the syringe barrel after injection (e.g., less than about 10% of the slurry, between about 10% and 20% of the slurry, or more than 20% of the slurry).

Referring collectively to FIGS. 4-19, in some embodiments, a syringe 400 with a crystallized (i.e., frozen) internal solution is initially secured to sled 404 (or back holder mount 806) of a docking station. Sled 404 (or back holder mount 806) travels upward along rails 405 (or rails 1109) toward upper brushless DC motor 604 (or spindle motor 1100) carrying syringe 400. Drive shaft 605 is rotated slowly via upper brushless DC motor 604 (or via spindle motor 1100) to engage its male bayonet connector 606 with the female bayonet connector 700 of blade shaft 701. Once drive shaft 605 and blade shaft 701 are coupled, blades 402, which are attached to blade shaft 605, are advanced from pre-blend zone 1502 into blend zone 1503. Upper brushless DC motor 604 (or spindle motor 1100) causes rotation of drive shaft 605 and blade shaft 701 to in turn cause spinning of blades 402. Blades 402 spin at high speeds (e.g., about 15,000 RPM) to blend the internal syringe 400 contents to form an injectable cold slurry. After blending is complete, upper brushless DC motor 604 (or spindle motor 1100) begins to slowly spin in the opposite direction from the blending direction to cause disengagement of male bayonet connector 606 of drive shaft 605 from the female bayonet connector 700 of blade shaft 701. Sled 404 (or back holder mount 806) is then moved from its engaged position downward along rails 405 (or rails 1109) to its resting position. Syringe 400 is removed from sled 404 (or back holder mount 806) and is ready for use. Plunger 401 is then advanced into pre-blend zone 1502 to cause ejection of the slurry 1504 from a syringe tip, while blades 402 remain positioned in blend zone 1503. Plunger 401 will be advanced into blend zone 1503 for the purpose of injecting a patient with cold slurry at a target location.

Figure 20A:
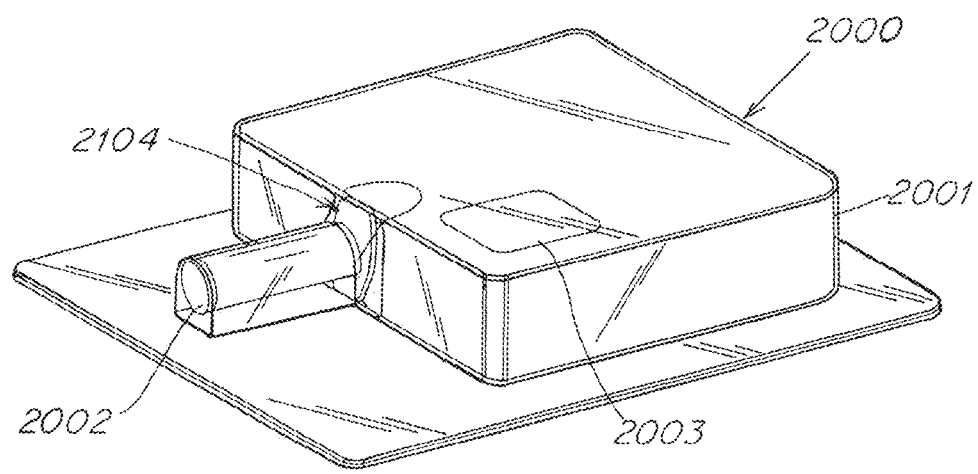
FIGS. 20A-B are perspective views of a docking station configured to blend internal contents of a syringe using magnetic drive.
Figure 20B:
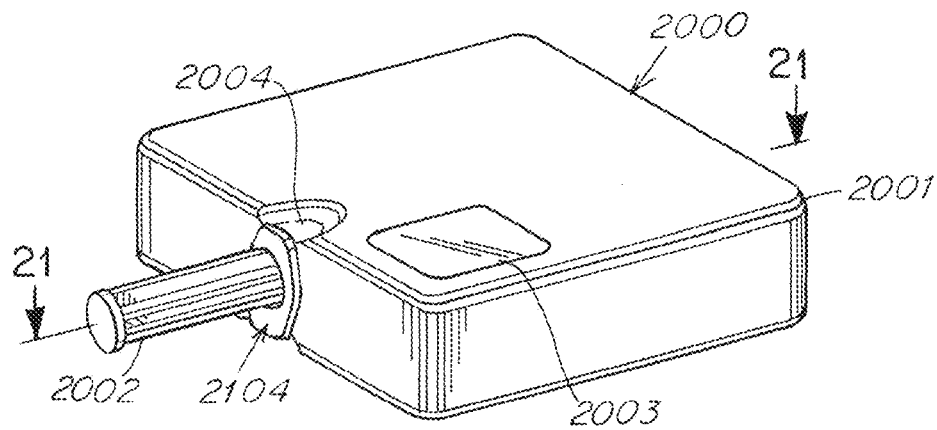

In another embodiment, the blending mechanism may be driven through magnetic coupling by using one or more magnetic components. FIGS. 20A and 20B show docking station 2000 with a syringe 2104 located inside housing 2001 of docking station 2000 for effectuating blending. Plunger 2002 is depicted as located on the outside of housing 2001 while the syringe barrel (not seen in depicted view) is located inside docking station 2000. Control panel 2003 visually displays a variety of operational settings and modes such as blending speed, power, mode, time remaining, slurry temperature, etc. Control panel 2003 can also include buttons or a touch screen to allow a user to change the operational settings/mode. Alternatively, the settings/mode may also be changed using any method known in the art such as a remote control. FIG. 20B shows dish outs 2004 which allow a person to easily insert a syringe and remove a syringe from docking station 2000 by holding onto the syringe barrel flange.

Figure 21:
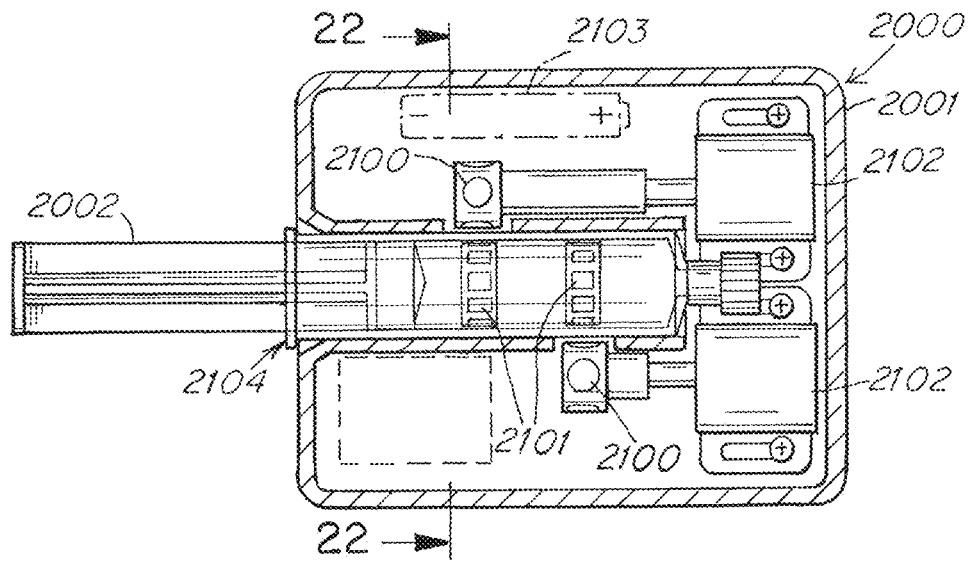
FIG. 21 is a cross-sectional top view of a docking station configured to blend internal contents of a syringe using magnetic drive, shown with and without packaging respectively.

Referring to FIG. 21, a cross-sectional view of docking station 2000 (including housing 2001) is depicted with syringe 2104 secured in place with plunger 2002 in its nondepressed state. Docking station 2000 includes rotating magnets 2100 that drive magnetic components 2101. Magnetic components 2101 are located within syringe 2104. While two magnetic components 2101 are depicted, any number of magnetic components may be used with the present disclosure such as one, two, three, or more than three magnetic components. Rotating magnets 2100 are driven by motors 2102. Motors 2102 may in turn be powered through an internal battery compartment 2103 that can hold one, two, three or more batteries. Any standard battery size may be used with the present disclosure such as 3LR12, D, C, AA, AAA, AAAA, A23, PP3, CR2032, LR44 batteries, etc. Also, any standard battery type may be used with the present disclosure such as lead acid, lithium ion, lithium polymer, nickel metal hydride, nickel cadmium, etc. Alternatively, docking station 2000 may be connected to a power supply through any method known in the art. For example, docking station 2000 may have a cord insertion terminal that allows connection of the docking station 2000 to a wall outlet power supply via a power cord. Docking station 2000 may be configured to operate using AC power, DC power, and a combination thereof. Docking station 2000 may also drive magnetic components 2101 through electromagnetism (e.g., using a brushless motor as described herein).

Figure 22:
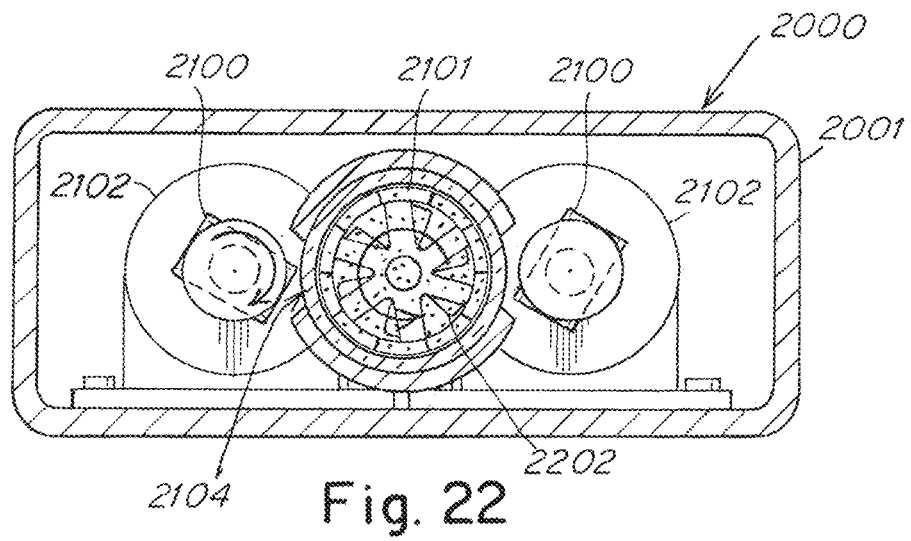
FIG. 22 is a cross-sectional front view, taken along line 22-22 of FIG. 21.
Figure 23:
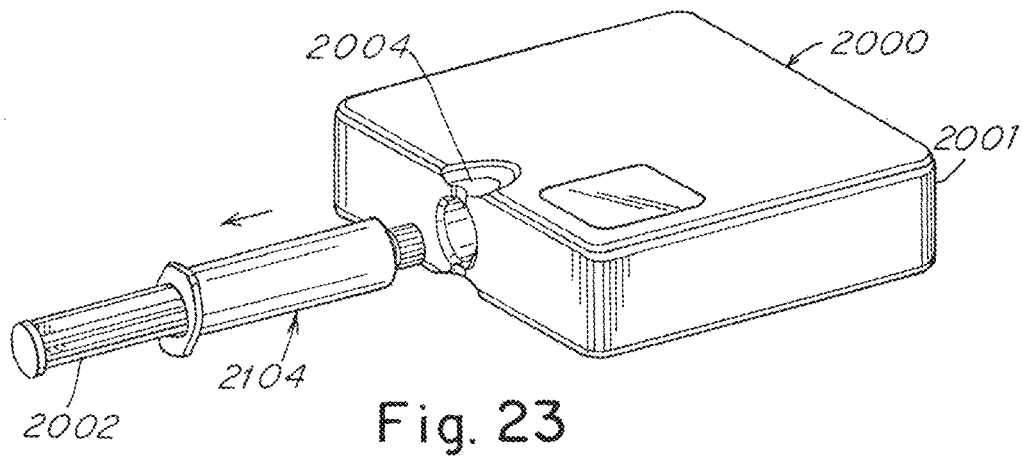
FIG. 23 is an exploded perspective view of a docking station configured to blend internal contents of a syringe using magnetic drive showing a syringe being removed after completion of blending.
Figure 24:
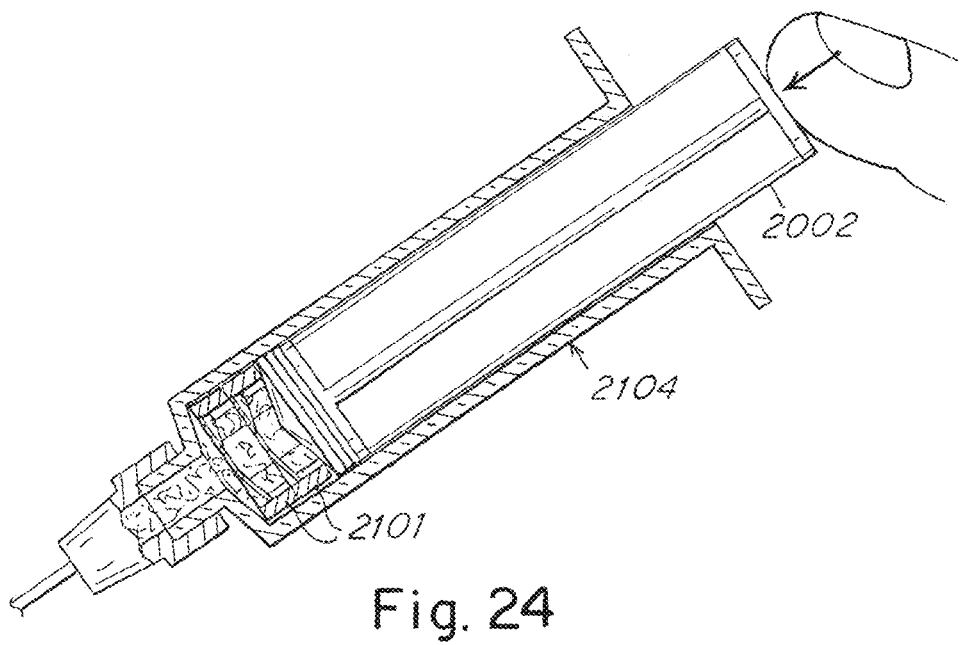
FIG. 24 is a cross-sectional schematic side view of slurry being injected through a syringe into a patient after completion of blending.

FIG. 22 shows a cross-sectional view of docking station 2000 (having a housing 2001) with rotating magnets 2100 driven by motors 2102 external to syringe 2104, and magnetic component 2101 located inside of syringe 2104 containing blades 2202. FIG. 23 shows syringe 2104 (having a plunger 2002) removed from docking station 2000 (having a housing 2001 and dish outs 2004) after blending is complete. FIG. 24 shows syringe 2104 with plunger 2002 advanced toward the syringe tip to cause slurry solution to be injected into a patient. Magnetic components 2101 are pushed toward the bottom portion of the syringe barrel near the tip pf syringe 2104 when plunger 2002 is in its most advanced position. In some embodiments, a certain percentage of slurry remains inside the syringe barrel after injection (e.g., less than about 10% of the slurry, between about 10% and 20% of the slurry, or more than 20% of the slurry).

Figure 25:
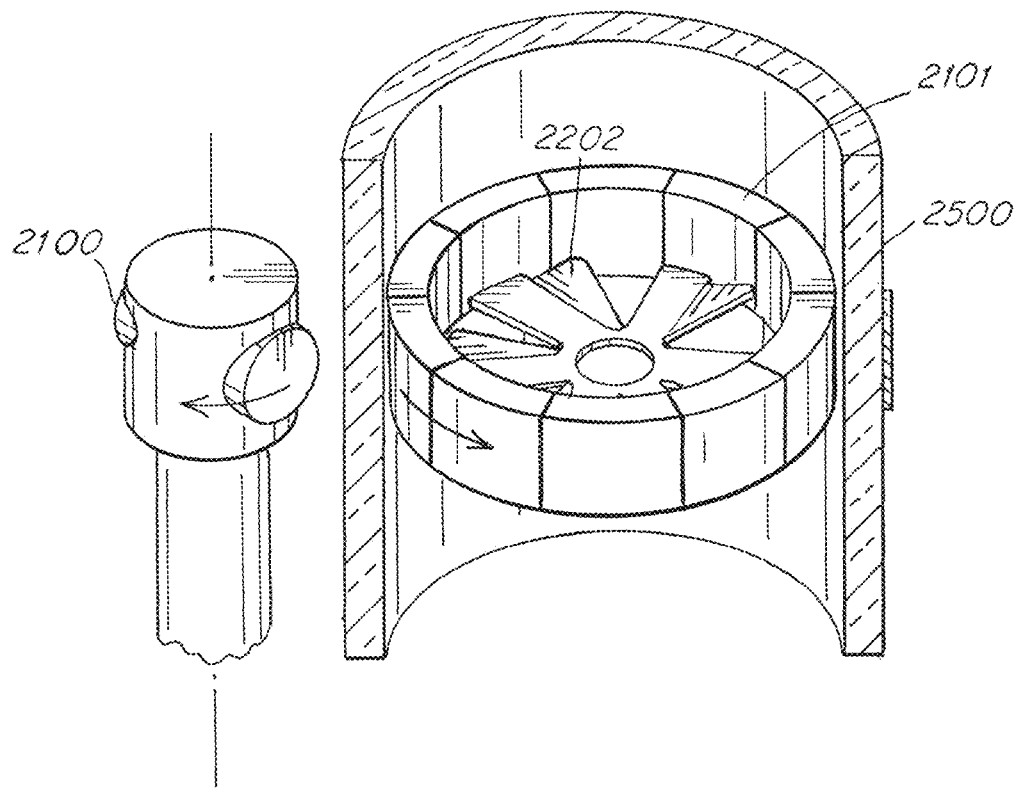
FIG. 25 is a fragmentary partially broken away perspective view of a syringe barrel with an internal magnetic component and an external rotating magnet.
Figure 26:
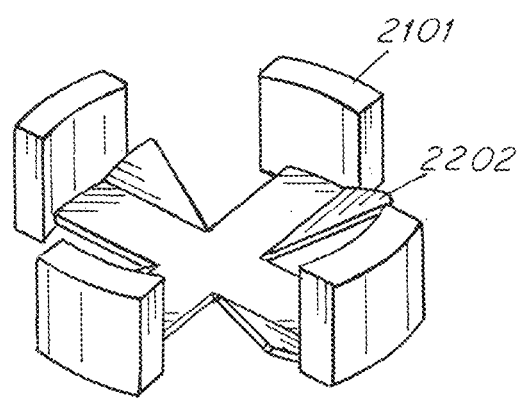
FIG. 26 is a perspective view of a cross shaped magnetic component that can be placed inside a syringe to blend the internal contents of the syringe.
Figures 27, 28:
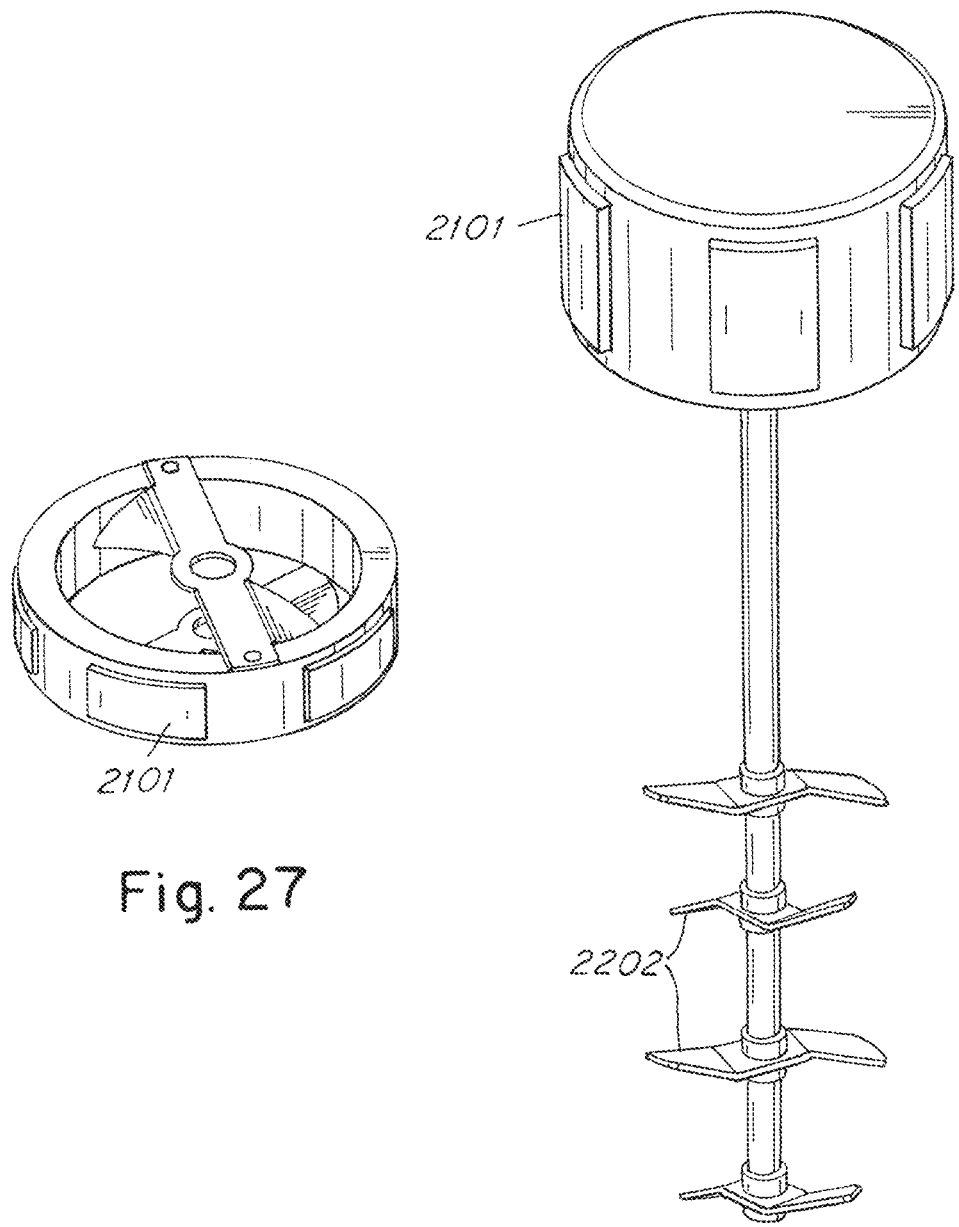
FIG. 27 is a perspective view of a magnetic component with a circular portion and two elongated portions extending along the diameter forming an "X" shape that can be placed inside a syringe to blend the internal contents of the syringe.
FIG. 28 is a perspective view of a magnetic component with a long shaft and four blades that can be placed inside a syringe to blend the internal contents of the syringe.

Various designs and configurations of magnetic components may be internal to a syringe for effectuating blending. The magnetic component may be comprised entirely of magnetic materials or may be comprised of a combination of magnetic and non-magnetic components such as magnets coupled to non-magnetic blades. FIG. 25 illustrates a cross-sectional view of syringe barrel 2500 with magnetic component 2101 and rotating magnet 2100 which is part of a docking station (not shown). Magnetic component 2101 is comprised of a circular magnetic perimeter with multiple magnetic blades 2202 arranged in a circular pattern. Rotation of rotating magnet 2100 causes rotation of magnetic component 2101 which causes creation of slurry inside of syringe barrel 2500. FIG. 26 shows an alternative magnet design comprised of four extended blades forming a cross shape with magnetic component 2101 coupled to blade 2202. FIG. 27 shows magnetic components 2101 with a circular frame and two elongated portions extending along the diameter forming an "X" shape. FIG. 28 depicts a magnetic configuration with magnetic components 2101 and a long central shaft with several rows of non-magnetic blades 2202. Other shapes and configurations of the magnetic components can include magnets shaped like stars, spheres, squares, or any other shape.

Figure 29:
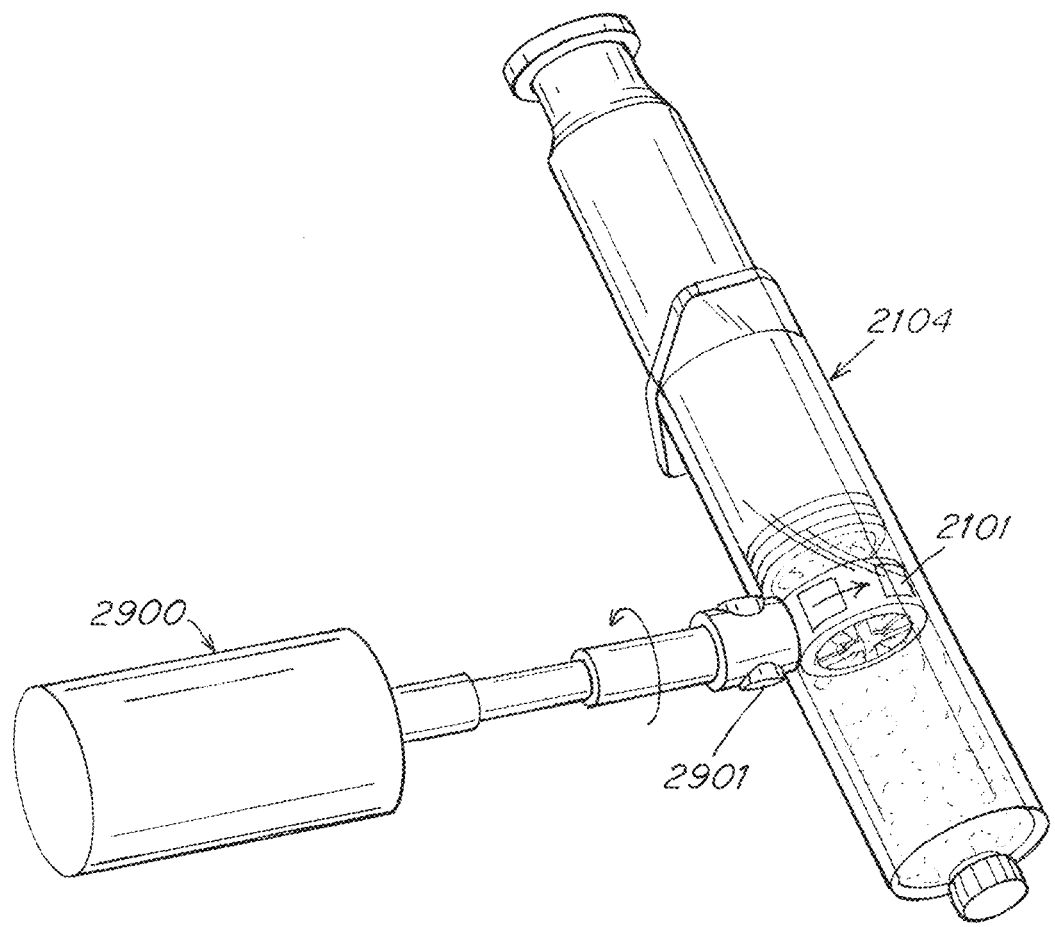
FIG. 29 is a perspective view of a handheld magnetic stirrer and a syringe with internal magnetic components.

Referring to FIG. 29, an alternative embodiment of a magnetic drive blending mechanism is depicted. Handheld magnetic stirrer 2900 has a rotating magnet 2901 extended toward the body of syringe 2104. Rotating magnet 2901 rotates to cause magnetic components 2101 inside of syringe 2104 to be agitated which in turn blends the internal syringe contents to form cold slurry. Handheld magnetic stirrer 2900 may be connected to a power supply through any method known in the art. For example, handheld magnetic stirrer 2900 may have a cord insertion terminal that allows connection of the handheld magnetic stirrer 2900 to a wall outlet power supply via a power cord. Handheld magnetic stirrer 2900 may be configured to operate using AC power, DC power, and a combination thereof. Alternatively, or in addition, to the wall supplied power, handheld magnetic stirrer 2900 may have an internal battery compartment that can hold one, two, three or more batteries. Any standard battery size or type may be used with the present disclosure as previously described herein.

Figure 30:
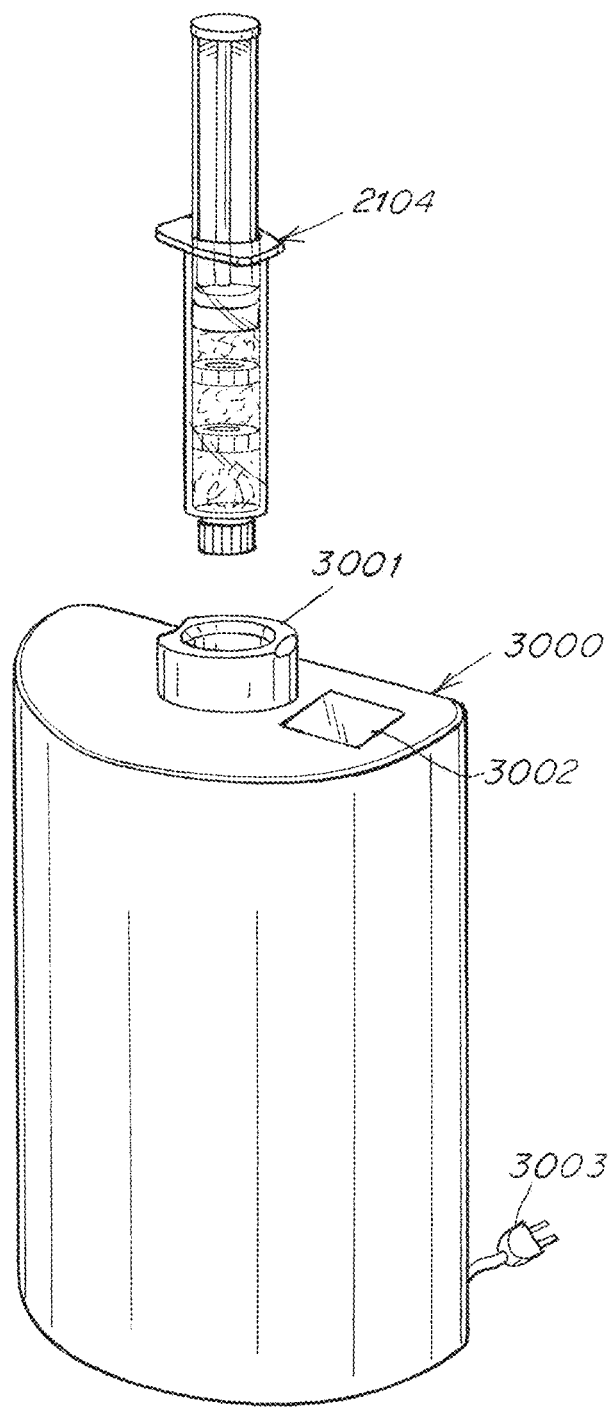
FIG. 30 is an exploded perspective view of a docking station configured to blend internal contents of a syringe using magnetic drive and a syringe.

Referring to FIG. 30, another embodiment of a magnetic drive blending system is depicted showing docking station 3000 with dock 3001 configured to accept syringe 2104. Docking station 3000 may have a control panel 3002 that can visually display a variety of operational settings and modes such as blending speed, power, mode, time remaining, slurry temperature, etc. Control panel 3002 can also include buttons or a touch screen to allow a user to change the operational settings/mode. Alternatively, the settings/mode may also be changed using any method known in the art such as a remote control. Docking station 3000 may be connected to a power supply through any method known in the art. For example, docking station 3000 may have a cord insertion terminal that allows connection of the docking station 3000 to a wall outlet power supply via power cord 3003. Docking station 3000 may be configured to operate using AC power, DC power, and a combination thereof. Alternatively, or in addition, to the wall supplied power, docking station 3000 may have an internal battery compartment that can hold one, two, three or more batteries. Any standard battery size may be used with the present disclosure as described herein.

Figure 31:
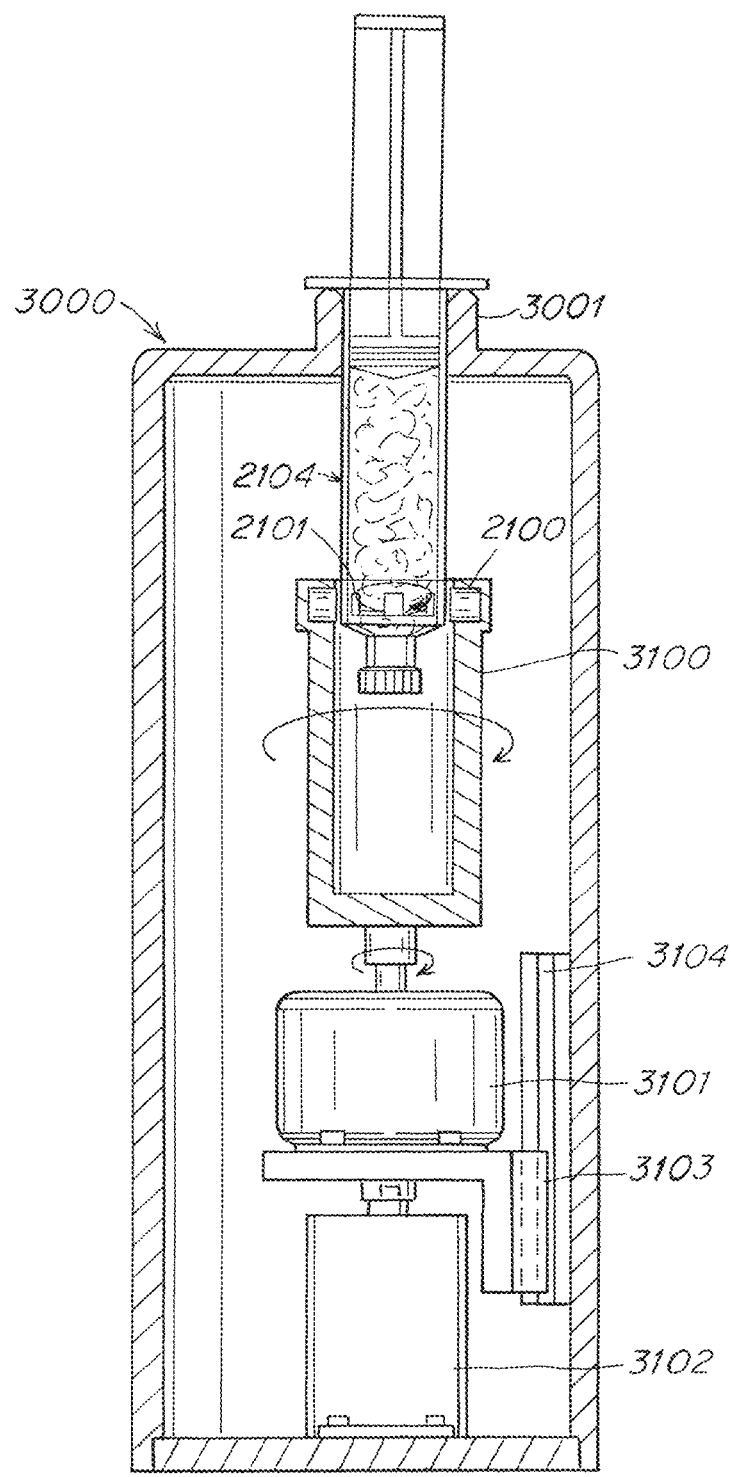
FIG. 31 is a cross-sectional schematic side view of a docking station configured to blend internal contents of a syringe using magnetic drive with a linear actuator in its retracted position and a syringe in the docked position.
Figure 32:
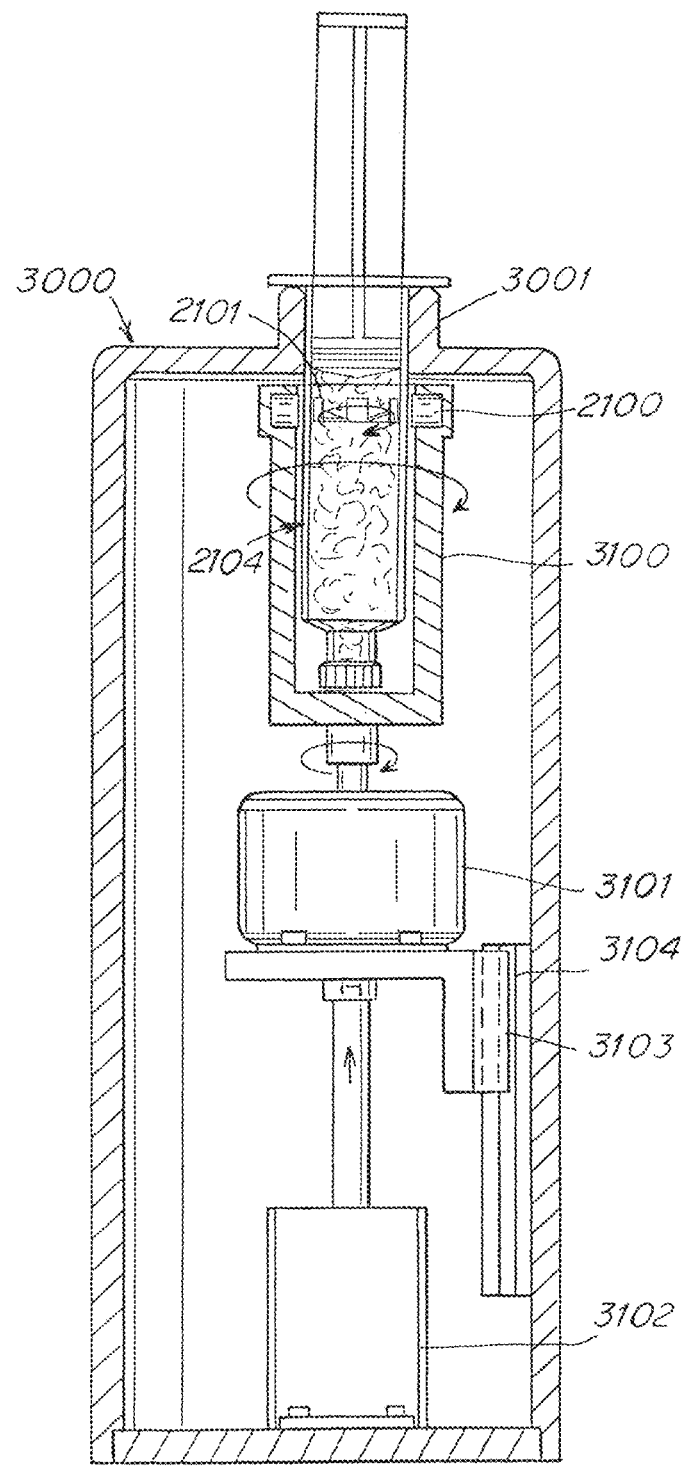
FIG. 32 is a cross-sectional schematic side view similar to FIG. 32 but with the linear actuator in its extended position and a syringe in the process of having its internal contents blended.

Referring to FIGS. 31 and 32, cross-sectional schematic views of docking station 3000 are illustrated with syringe 2104 placed in dock 3001. A portion of syringe 2104 sits within magnetic cup 3100 which in turn sits on top of motor 3101. When the blending functionality of docking station 3000 is initiated, motor 3101 causes magnetic cup 3100 to rotate which causes rotation of rotating magnet 2100 inside magnetic cup 3100 and in turn engages magnetic component 2101 located inside of syringe 2104, thus effectuating blending of the internal contents of syringe 2104. In some embodiments, during blending, linear actuator 3102 extends and retracts in a linear motion causing sled 3103 to move up and down guide rails 3104 which in turn moves motor 3101 and magnetic cup 3100 along the longitudinal axis of syringe 2104 to allow for a more homogenous blending of the syringe 2104 contents. The linear motion of magnetic cup 3100 caused by linear actuator 3102 can be coupled with the rotational motion of magnetic cup 3100 caused by motor 3101. Alternatively, the linear and rotational motions can be effectuated separately or in various combinations/cycles throughout blending. FIG. 31 shows linear actuator 3102 in its most retracted position, while FIG. 32 shows linear actuator 3102 in its most extended/upward position. Linear actuator 3102 can proceed through a cycle of retraction and extension for a plurality of cycles during any given blending episode.

The magnetic component can be integrated within the syringe in a manner that maintains sterility of the internal syringe contents. The magnetic component may be fixed to the bottom portion of the plunger, to the internal walls of the syringe barrel, to the distal portion of the syringe barrel near the syringe tip, etc. For example, a magnetic component that includes blades may be fixed in the vertical plane such that the blades are allowed to spin solely in the horizontal plane. The magnetic component can be fixed inside the syringe barrel using any technique known in the art, for example, by using magnetic tape. Alternatively, the magnetic component may be located inside of the syringe body without attachment such that magnetic drive will cause the magnetic component to move freely within the internal syringe space and through the internal syringe contents. In another embodiment, the magnetic component may be fixed in a position within the syringe initially, and activation of magnetic drive may create force that causes dissociation of the magnetic component from its fixed position to allow free movement of the magnetic component during blending. Magnetic components of different sizes, shapes, and configurations can be used to achieve a desired cold slurry consistency.

Figure 33:
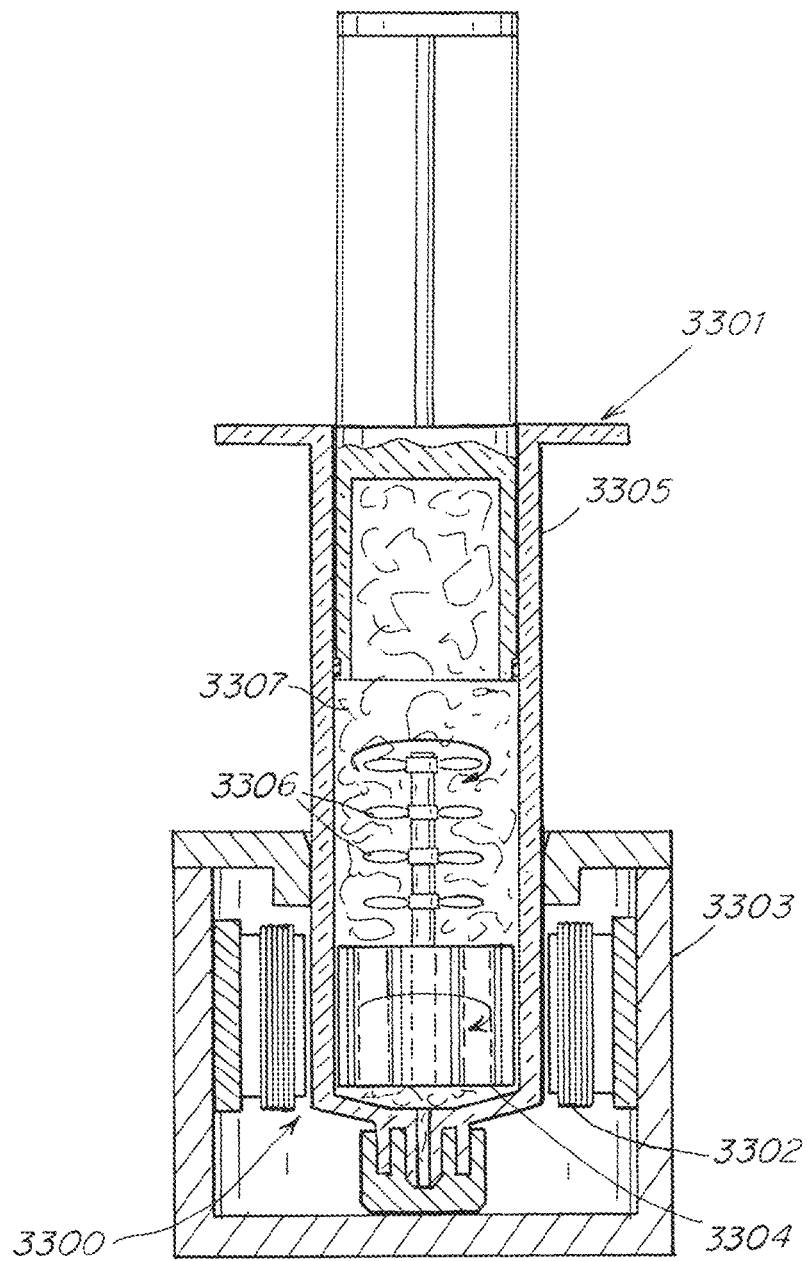
FIG. 33 is a cross-sectional schematic front view of an inrunner brushless motor configured to blend internal contents of a syringe with a rotor located inside of the syringe barrel.

In another embodiment, blending of internal syringe content may be effectuated using electromagnetism. Referring to FIG. 33, a cross-sectional view of a brushless motor 3300 that is configured to accept syringe 3301 is depicted. Brushless motor 3300 is an inrunner with stator coils 3302 located inside housing 3303. Stator coils 3302 are on the outside of rotor 3304 that is located inside of syringe barrel 3305. Rotor 3304 has magnets with north and south poles (not shown). Brushless motor 3300 is connected to a power source using any method known in the art as described herein. When brushless motor 3300 is activated using a power source, electricity runs through and excites the stator coils 3302 which in turn cause the rotor 3304, which contains magnets, to spin. The spinning of rotor 3304 causes blades 3306 to spin and to blend a solution located inside of syringe 3301 to create cold slurry 3307.

Figures 34, 35:
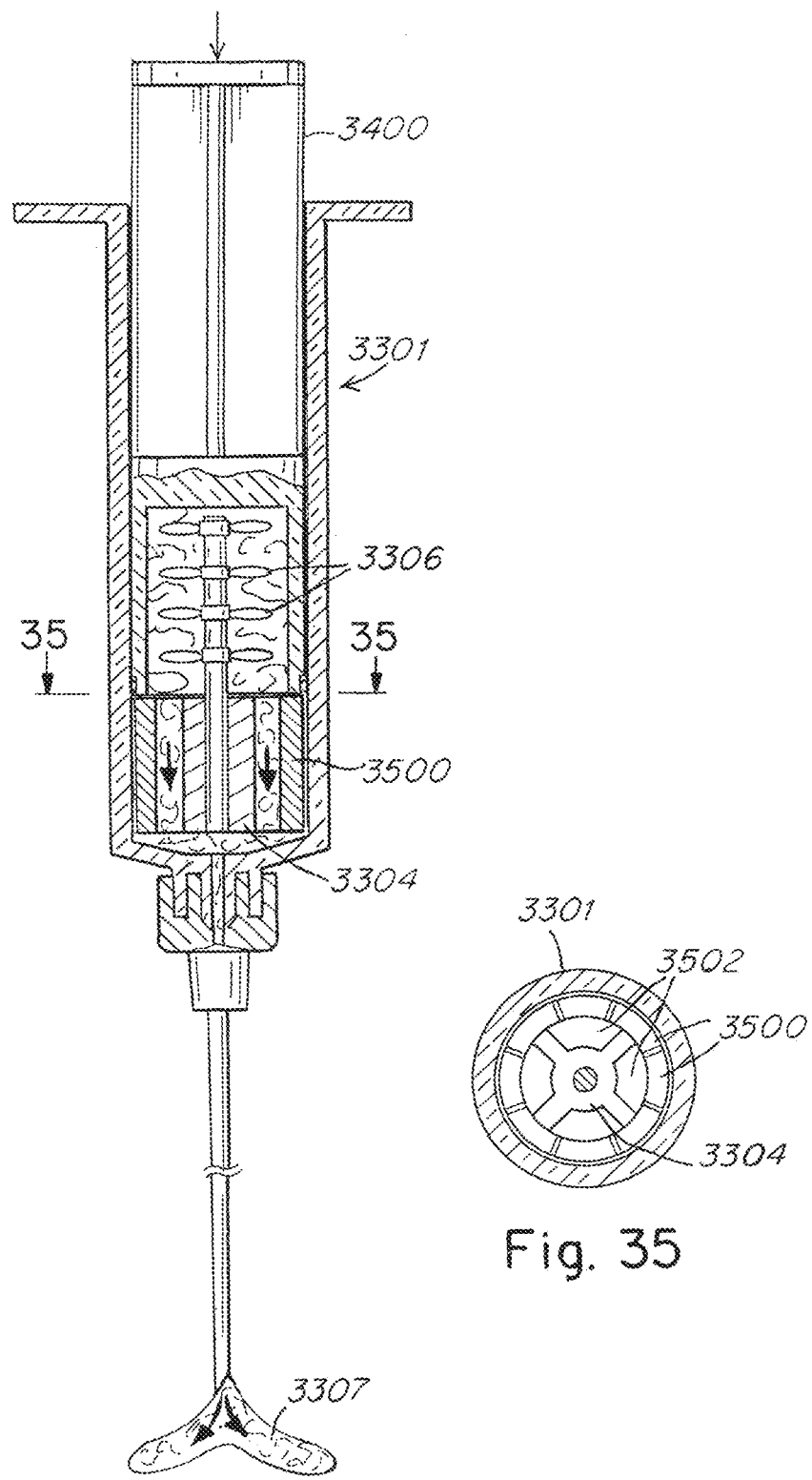

FIG. 34 depicts a cross-sectional side view of syringe 3301 with plunger 3400 advanced toward the tip of syringe 3301 to eject cold slurry 3307 for administration to a patient. As plunger 3400 is advanced toward the tip of syringe 3301, blades 3306 move toward rotor 3304 located just above the syringe tip. Rotor 3304 is stationary along the longitudinal axis of syringe 3301 during active blending (see FIG. 33) and during ejection of slurry for administration to a patient as depicted in FIG. 34. FIG. 35 depicts a cross-sectional plan view of rotor 3304 with magnets 3500. When cold slurry is ejected from a syringe (see FIG. 34), the cold slurry passes through fluid passages 3502 in rotor 3304.

Figure 36:
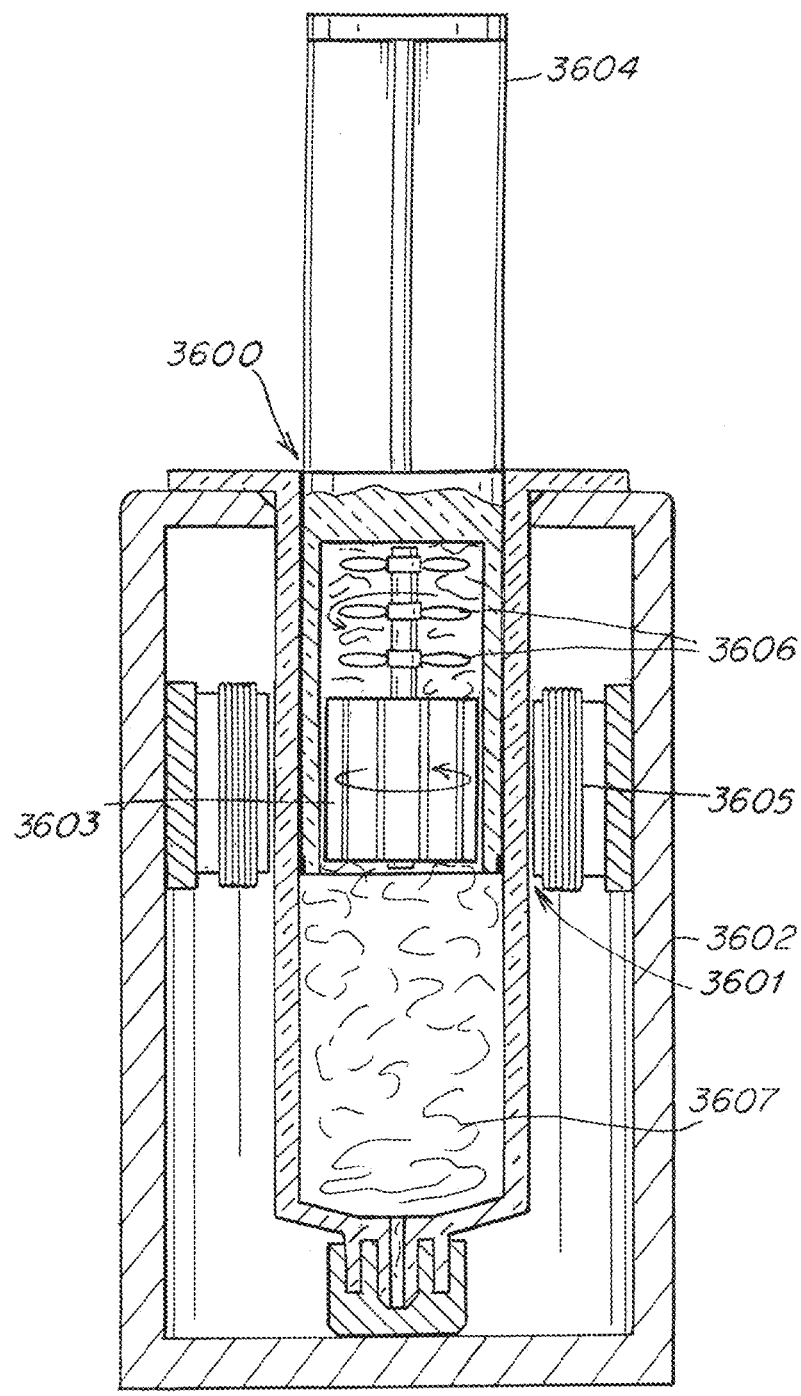
FIG. 36 is a cross-sectional schematic front view of an inrunner brushless motor configured to blend internal contents of a syringe with a rotor located inside of the syringe plunger.

In an alternative embodiment of a brushless motor, a rotor may be located inside of a syringe plunger. Referring to FIG. 36, a cross-sectional schematic front view of syringe 3600 is depicted inside a housing 3602 of brushless motor 3601. Brushless motor 3601 is an inrunner that includes rotor 3603 located inside of plunger 3604 and stator coils 3605 located within housing 3602. Rotor 3603 has magnets with north and south poles (not shown). Brushless motor 3601 is connected to a power source using any method known in the art as described herein. When brushless motor 3601 is activated using a power source, electricity runs through and excites stator coils 3605 which in turn cause the rotor 3603, which contains magnets, to spin. The spinning of rotor 3603 causes blades 3606 to spin and to blend a solution located inside of syringe 3600 to create cold slurry 3607.

Figure 37:
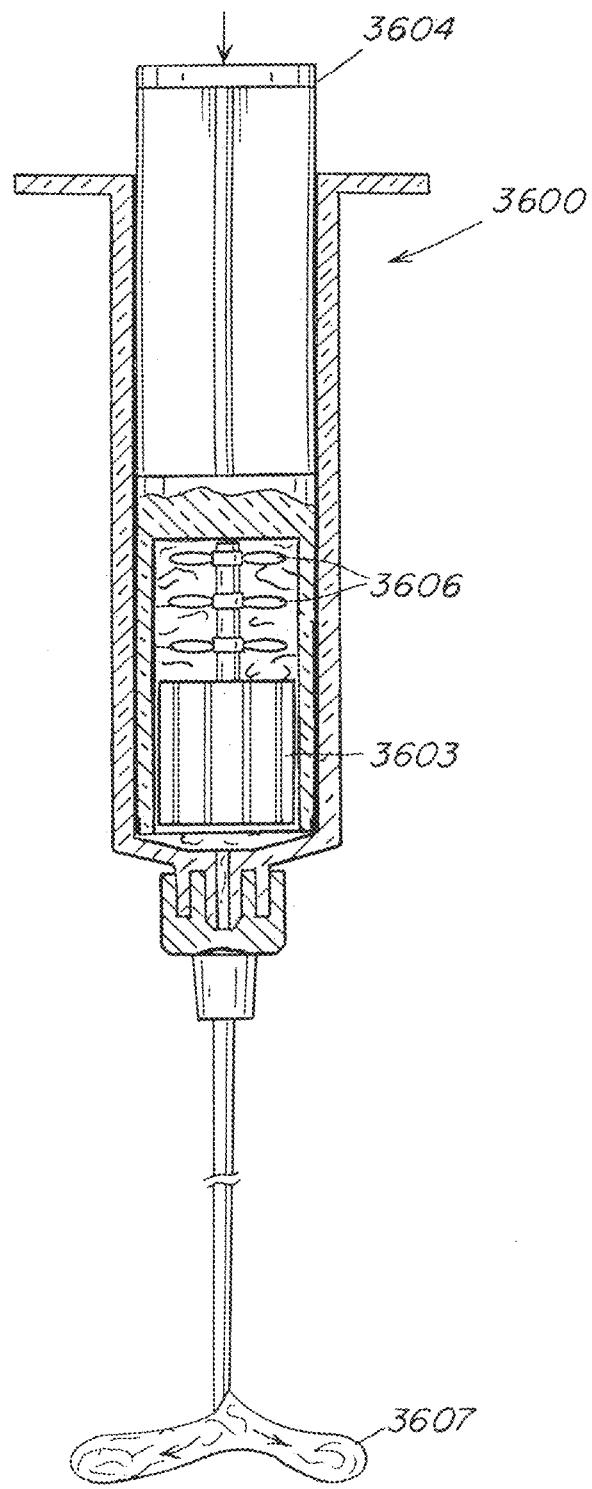
FIG. 37 is a cross-sectional view of a syringe dispensing slurry for administration to a patient with a rotor located inside of the syringe plunger.

FIG. 37 depicts a cross-sectional side view of syringe 3600 with plunger 3604 advanced toward the tip of syringe 3600 to eject cold slurry 3607 for administration to a patient.

As plunger 3604 is advanced toward the tip of syringe 3600, blades 3606 move toward rotor 3603 located just above the syringe tip. Rotor 3603 is stationary along the longitudinal axis of syringe 3600 during active blending (see FIG. 36) and during ejection of slurry for administration to a patient as depicted in FIG. 37.

In some embodiments, a filter or a plurality of filters may be used with the present disclosure to create an injectable and flowable cold slurry. In such embodiments, a syringe that includes an internal filter is initially subjected to cooling to at least partially crystallize the internal syringe contents. The syringe is then subjected to one or more of the above described blending methods to create a cold slurry. When the plunger of the syringe is advanced, the cold slurry passes through the internal syringe filter to turn the cold slurry into a more flowable and injectable form. In some embodiments, a syringe includes a plastic mesh, or a metal mesh filter located within the internal syringe space just above the syringe tip. When the plunger is advanced toward the syringe tip, the cold slurry passes through the filter, which can be used to prevent clogging of ice particles through a needle connected to the syringe at the syringe tip. One or more filters may be located anywhere within the internal space of the syringe body such that when the plunger is advanced, the cold slurry is pushed through the filter(s). The filter can be used to ensure that only ice particles below a particular size may pass through the filter and out of the needle. The filter may be comprised of mesh with a variety of pore sizes that are suitable for allowing passage of ice particles smaller than about 0.5 to 1.5 mm in diameter, smaller than between about 1.5 mm in diameter and 2.5 mm in diameter, smaller than between about 2.5 mm and 3.5 mm diameter, or smaller than about 3.5 mm in diameter. The filter may be comprised of mesh or foam and can be made of any suitable material known in the art including metal and metal alloys (e.g., steel, stainless steel, nickel, aluminum, brass, copper), fiberglass, plastics and polymers (e.g., polyethylene, polypropylene, PVC, PTFE, nylon, elastomers), natural fibers, etc.

Figure 38:
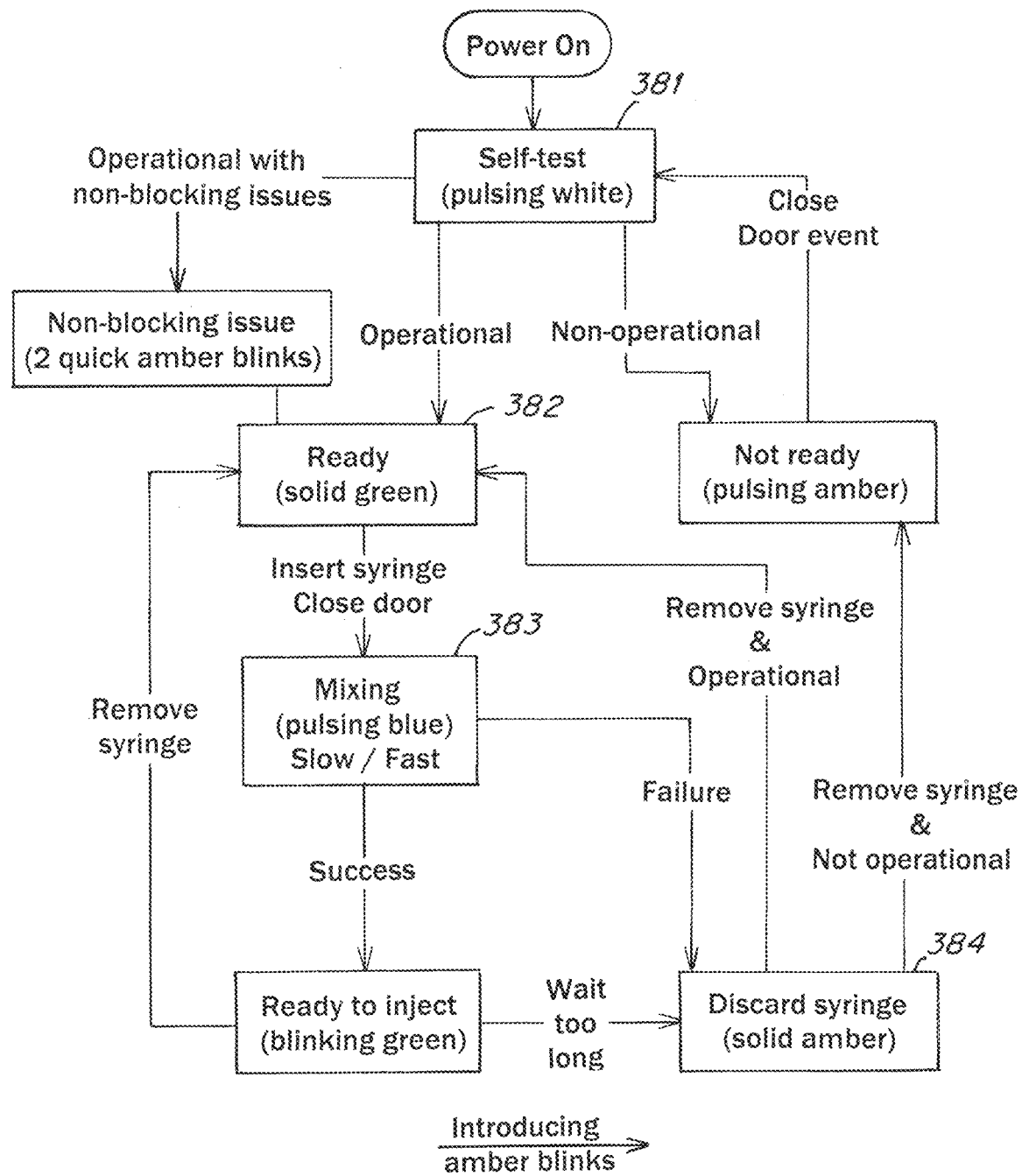
FIG. 38 is an operational flow diagram showing various device operational states and corresponding LED light status.

Referring to FIGS. 38-41, operation flow diagrams are depicted showing different operational states of the docking stations of the present disclosure and corresponding LED status. The operation can be controlled by a system that includes a processor or a plurality of processors located within the apparatus/device itself and/or located separate from the device and in communication with the device by way of any communications network known in the art such as an intranet, the Internet, a local area network (LAN), a wide area network (WAN), a wireless fidelity (WiFi) network, a cellular network, and the like. The operational flow begins when a power switch on the device (e.g., docking station 403, 803, 2000, or 3000) is turned on ("Power On"). The device has one or more LED lights located on any part of the device that is visible to a user during operation. Reference is made to various colors of the LED light during device operation, but any colors can be used in place of the colors discussed with reference to FIGS. 38-41. Referring to FIG. 38, at step 381, the system initiates a self-test to determine if the device is operational and the LED light pulses with a white color during the self-test. The decision output at this step is whether the device is operational, operational with non-blocking issues, or not operational. Depending on which of these three states is detected following the self-test phase, a different operational flow path follows, as described in greater detail below.

At step 381, if the system determines that the device is operational, the operational flow moves to step 382 during which the LED light turns to a sold green color indicating a ready state. If the device is operational with a non-blocking issue (at step 381), the LED light blinks quickly twice with an amber color to indicate to the user that there is a non-blocking issue and then moves to the ready state at step 382. A non-blocking issue is a detected problem with the device which will not affect the mixing/blending operation of the device. Examples of non-blocking issues include detecting that an SD card is not present, and a discrepancy between printed-circuit board (PCB) temperature sensors. The one or more PCB temperature sensors can be used to detect whether a main control circuit board of the docking station is overheating. In some embodiments, if overheating is detected (e.g., one or more PCB temperature sensor detects a temperature above a predetermined threshold such as above 40° C.), the power to the docking station is automatically shut off to prevent damage to the main control circuit board. The main control circuit board can be located anywhere within or outside of the docking station (e.g., behind the brushless DC motor of FIG. 14; main control circuit board not depicted). If two PCB temperature sensors on the main control circuit board show a discrepancy in the temperature reading of approximately 5° C. or more of each other, a non-blocking issue is detected.

If the device is not operational (at step 381), the LED light pulses with an amber color indicating that a syringe cannot be inserted for initiating a mixing/blending operation. At this point, in some embodiments, the user may open and close a safety door of the device to return the operational flow status of the device back to step 381 which during a self-test can begin again (LED pulses white). If there is no safety door on the device, the user may press a button on the device to return the device operational flow status back to step 381. At step 381, if the device is determined to be operational or operational with a non-blocking issues, the operational flow moves to step 382.

At 382, during which the LED light is a sold green color indicating a ready state, a syringe can be inserted into a syringe dock of the device. In some embodiments, the user must close a safety door after inserting the syringe and prior to continuing to the next step (e.g., safety door 801, see FIGS. 8 and 9). Once the system determines the presence of a syringe (e.g., using a sensor on the device), and in some embodiments also determines that the safety door is closed, the operational flow continues to step 383. At step 383, the blending operation of the device is initiated to transform the contents of the syringe into an injectable cold/ice slurry and the LED light pulses with a blue color (the pulsing may be slow or fast) during the blending or mixing operation. When the blending or mixing operation is complete, it is determined whether the blending or mixing operation was a success or failure. If the blending or mixing operation was a success, the LED light blinks with a green color to indicate success. Blending or mixing success or failure can be determined based on one or more factors such as (but not limited to) temperature of the slurry (e.g., measured with an infrared sensor located on the docking station), detected maximum RPM achieved by motor, reading on PCB temperature sensors, blending time achieved at predetermined blending speeds, and the like. Once the LED light is blinking green indicating mixing or blending success, the user removes the syringe from the device, and the injectable and flowable cold slurry is ready to be injected into a patient at a target location. After the syringe is successfully removed from the device, the operational flow returns to the ready state at step 382 during which the LED light is a solid green color. At this point, a new syringe may be inserted into the docking station and the operational flow can continue again to step 383, as previously described. If the device senses that the syringe has not been removed from the device for a predetermined period of time (e.g., 1 minute, 2 minutes, 3 minutes, 4 minutes, 5 minutes, or more than 5 minutes), the LED light blinks with an amber color and the operation moves to step 384 during which the LED light turns a sold amber color and indicates that the syringe should be discarded and the slurry is not in a useable state. In some embodiments, the syringe will not need to be discarded and instead can be removed from the docking station and subjected to refreezing before attempting to initiate another blending operation. The operational flow can alternately move onto step 384 if a mixing failure is detected at step 383 (e.g., based on the mixing success/failure factors described above).

If a failure is detected, the operation moves to step 384 during which the LED light turns a sold amber color and indicates that the syringe should be discarded (or removed and refrozen), and the slurry is not in a useable state. At step 384, a user must remove the syringe from the device. Once the syringe is removed, a determination is made as to whether the device is operational or not operational. If the device is operational, the operational flow moves to step 382 during which the LED light is a solid green color indicating that the device is in a ready state for mixing and the operational flow steps continue from step 382, as previously described (e.g., move to step 383, etc.). If at step 384, after syringe removal, the device is determined not to be operational, the LED light pulses with an amber color to indicate that the device is not in a ready state and mixing or blending cannot take place. At this juncture, in some embodiments, the user may open the safety door and close the safety door which will move the operational flow back to step 381 during which the self-test is initiated again and the LED light pulses white. From step 381, the operation flow can begin again as described above (e.g., move to step 382).

Figure 39:
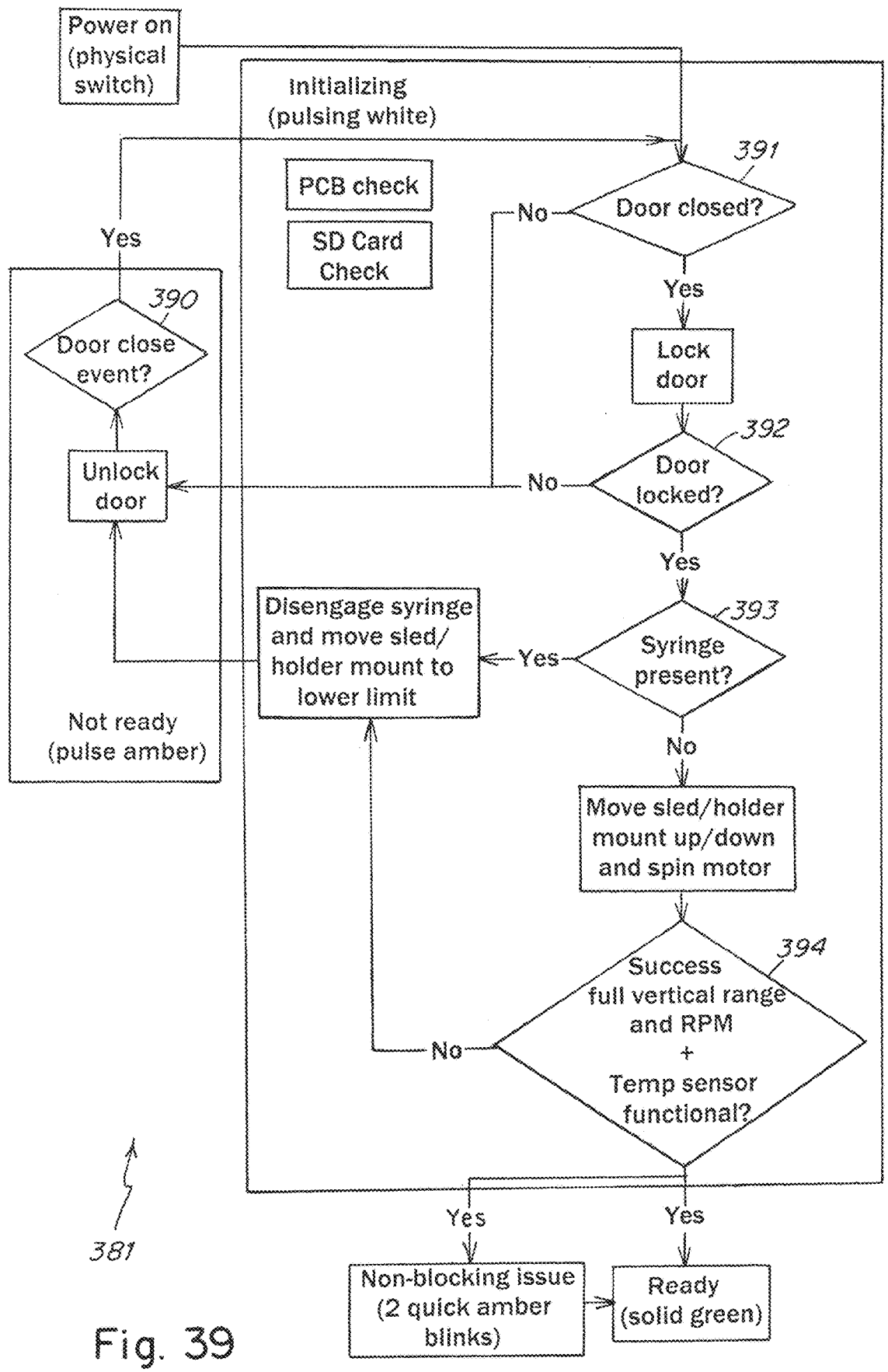
FIG. 39 is an operational flow diagram showing device operational steps during device self-test mode and corresponding LED light status.

FIG. 39 depicts the operational flow steps that take place during the self-test state of the device at step 381 as described above with respect to FIG. 38. Once the device is powered on, the operational flow moves to step 381 during which the LED light pulses white and a self-test is initiated to determine whether the device is operational, operational with a non-blocking issue, or not operational. In embodiments that have a safety door (e.g., see FIGS. 8 and 9), the self-test begins at step 391 during which a sensor on the device may detect whether the safety door is closed. If the door is closed, a signal is sent to the device to automatically lock the door and then the operational flow moves to step 392. If it is detected that the door is not closed, a signal is sent to the device to unlock the door, and another assessment is made to determine whether the door is closed at step 390 during which the LED light on the device pulses with an amber color. If the door is determined to be closed, a signal is sent to lock the door and the operational flow proceeds to step 392. At step 392, the system determines if the safety door is locked. If it is determined that the safety door is not locked, the system sends a signal to automatically unlock the safety door and the operational flow moves to step 390 during which the system checks again whether the door is closed (the operational flow can then move to step 391 and/or 392 as described above). If the door is determined to be closed, the operational flow moves to step 393. At step 393, the system determines if a syringe is present in the appropriate location within the device (e.g., using a sensor to determine if the syringe is docked). If the syringe is present, a signal is sent to the device to disengage the syringe and move the sled/holder mount to its lowest position (e.g., sled 404, see FIG. 6, or back holder mount 806, see FIG. 13), followed by unlocking the safety door, and moving to operational step 390 to determine again if the door is closed (the operational flow can then move to step 391 and/or 392 as described above). A syringe that is present at step 393 suggests that the syringe was not removed in time from a previous operation of the device and the syringe likely needs to be discarded. If it is determined that a syringe is not present, a test of the operation of the docking station is initiated which can involve sending a signal to cause vertical movement of the sled and holder mount, engagement of one or more motors, and obtaining temperature readings from PCB temperature sensors.

The operational flow moves next to step 394 during which the system determines if the device is operational, operational with non-blocking issue, or not operational. The determination is based on one or more factors such as whether a sufficient vertical range of motion was achieved for the movement of the sled/holder mount, whether a sufficient range of RPM values were achieved for the motor, whether a syringe temperature sensor (e.g., infrared sensor) was able to obtain temperature reads, whether a PCB temperature sensor (e.g., heat sensor) is functional and/or whether there is a discrepancy between temperature readings between two or more PCB temperature sensors, and whether an SD card is present and/or functional. The PCB check and SD card check may also be performed at any time during the entirety of self-test (step 381). If it is determined at step 394 based on one or more of the above-mentioned factors (or any other factors) that the device is operational, the LED light turns to a solid green color to indicate that the device is ready for use. If it is determined at step 394 based on one or more of these factors that the device is not operational, a signal is sent to the device to disengage the syringe and move the sled/holder mount to its lowest position (e.g., sled 404, see FIG. 6, or back holder mount 806, see FIG. 13), followed by unlocking the safety door, and moving to operational step 390 to determine again if the door is closed (the operational flow can then move to step 391 and/or 392 as described above). At step 390, the LED pulses in an amber color to indicate that the device is not ready for use. If it is determined at step 394 based on one or more of the above-mentioned factors (or any other factors) that the device is operational with a non-blocking issue, the LED light blinks twice with an amber color to alert the user that there may be one or more non-blocking issues, and then switches to a solid green color to indicate a ready state of the device. Examples of non-blocking issues include detecting that an SD card is not present, and a discrepancy between PCB temperature sensors. When the LED light is solid green, the operational flow moves to step 382 as described with respect to FIG. 38.

Figure 40:
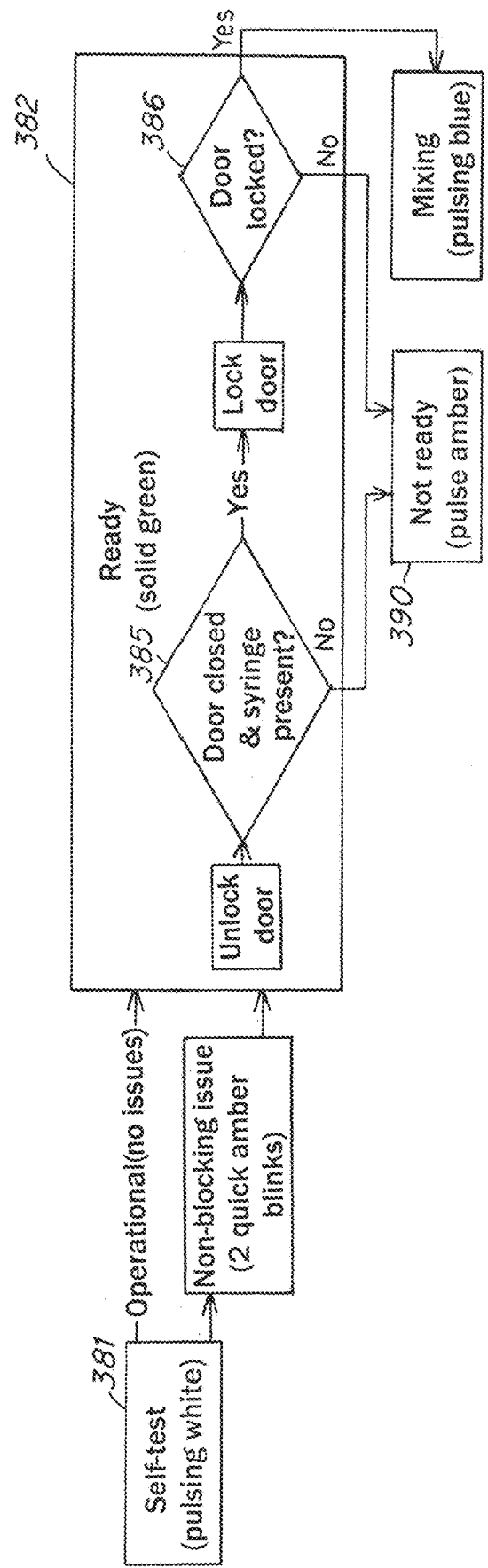
FIG. 40 is an operational flow diagram showing device operational steps during device ready state and corresponding LED light status.

Referring to FIG. 40, ready state operational flow step 382 (from FIG. 38) is described in more detail. As described herein, the operational flow of the system begins at step 381 with a self-test (during which the LED pulses with a white color) to determine if the device is operational, operational with a non-blocking issue, or not operational. If it is determined that the device is operational with a non-blocking issue, the LED pulses twice with an amber color and then turns solid green. If it is determined that the device is operational, the LED turns solid green without intermediary amber colored blinks. The solid green LED color indicates a ready state of the system which corresponds to operational flow step 382. At step 382, the system sends a signal to the device to unlock a safety door (in embodiments that have a safety door). The user then places a syringe in the device at an appropriate location, such as inserting the syringe into a dock that is configured to hold the syringe. At step 385, the system determines if the safety door is closed (in embodiments with a safety door) and the system determines whether a syringe is present within the device (e.g., using a sensor that detects a docked syringe). If it is determined that the safety door is closed and/or the syringe is present, the system sends a signal to automatically lock the safety door. At step 386, the system checks whether the safety door is locked (e.g., using a sensor located on the device). If the safety door is determined to be locked, the operational flow can proceed to step 383 (see FIG. 38) and the mixing/blending operation of the device can be initiated. On the other hand, if it is determined at step 385 that the safety door is not closed and/or that the syringe is not present, the operational flow continues to step 390 during which the LED pulses with an amber color and the device is not ready for use (see FIGS. 38 and 39). Likewise, if it is determined at step 386 that the safety door is not locked, the operational flow continues to step 390 during which the LED pulses with an amber color and the device is not ready for use (see FIGS. 38 and 39).

Figure 41:
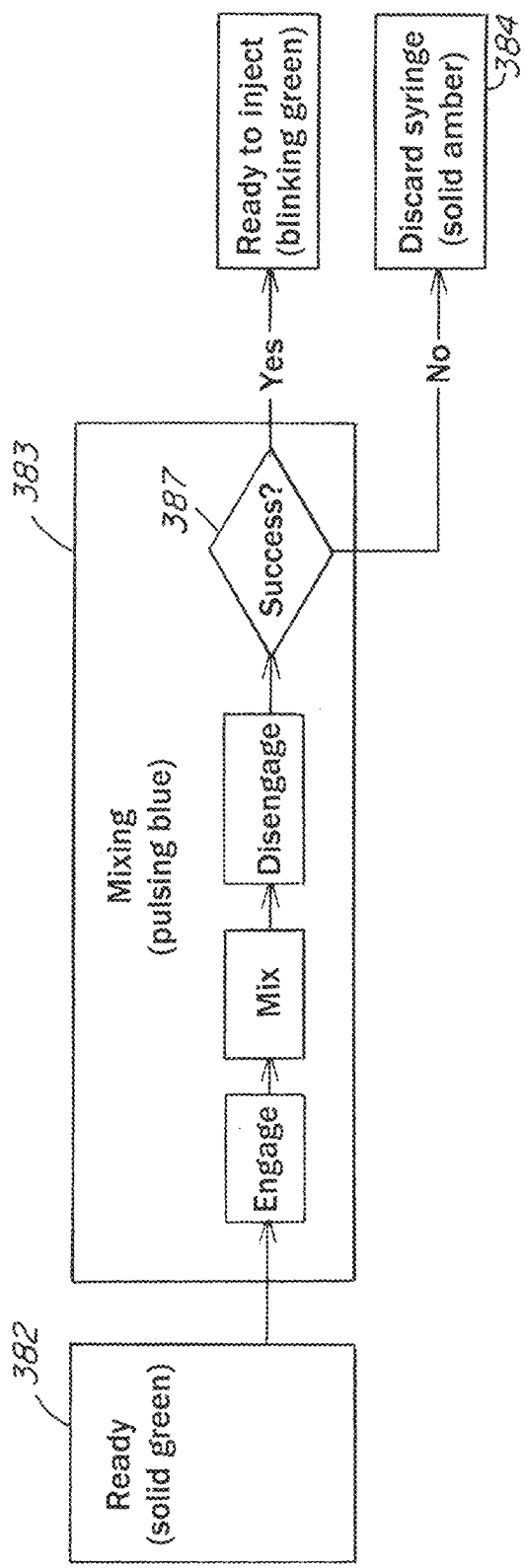
FIG. 41 is an operational flow diagram showing device operational steps during device mixing/blending state and corresponding LED light status.

Referring to FIG. 41, mixing state 383 (see FIG. 38), is described in more detail. Once the system is in a ready state at step 382 and no further operational issues are detected (see FIG. 40 and corresponding description), the operational flow moves to step 383 during which the LED pulses in a blue color and the mixing/blending operation of the device begins. During this step, the sled/holder mount (e.g., sled 404 or back holder mount 806, see FIGS. 4-19) holds the syringe having at least partially crystallized internal contents and travels upward along rails (e.g., rails 405 or rails 1106, see FIGS. 4-19) toward a motor. A drive shaft (e.g., drive shaft 605, see FIGS. 4-19) is rotated via a motor to engage with a blade shaft (e.g., blade shaft 701, see FIGS. 4-19). The motor (e.g., upper brushless DC motor 604 or spindle motor 1100, see FIGS. 4-19) causes rotation of the drive shaft and spins blades on the blade shaft (e.g., blades 402, see FIGS. 4-19) to blend the internal syringe contents to form an injectable cold slurry. After blending is complete, the motor (e.g., upper brushless DC motor 604 or spindle motor 1100, see FIGS. 4-19) spins in the opposite direction from the blending direction to cause disengagement of the drive shaft from the blade shaft (e.g., drive shaft 605 and blade shaft 701, see FIGS. 4-19). The sled/holder mount (e.g., sled 404 or back holder mount 806, see FIGS. 4-19) is then moved from its engaged position downward along the rails (e.g., rails 405 or rails 1106, see FIGS. 4-19) to its resting position. Following completion of the mixing/blending operation, the operational flow moves to step 387 during which the system determines whether the mixing or blending procedure was a success or failure. Mixing success or failure can be determined based on one or more factors such as (but not limited to) temperature of the slurry (e.g., measured with an IR sensor located on the device), detected maximum RPM achieved by motor, readings on PCB heat sensors, blending time achieved at predetermined blending speeds, and the like. If it is determined that the mixing operation was a success, the LED light blinks green to indicate success and the user may remove the syringe for injection into a patient at a target location. If the mixing operation is determined to be a failure, the LED light turns to a sold amber color (step 384, see FIG. 38) indicating to the user that the syringe should be discarded, and the syringe contents should not be injected into a patient.

Figure 42:
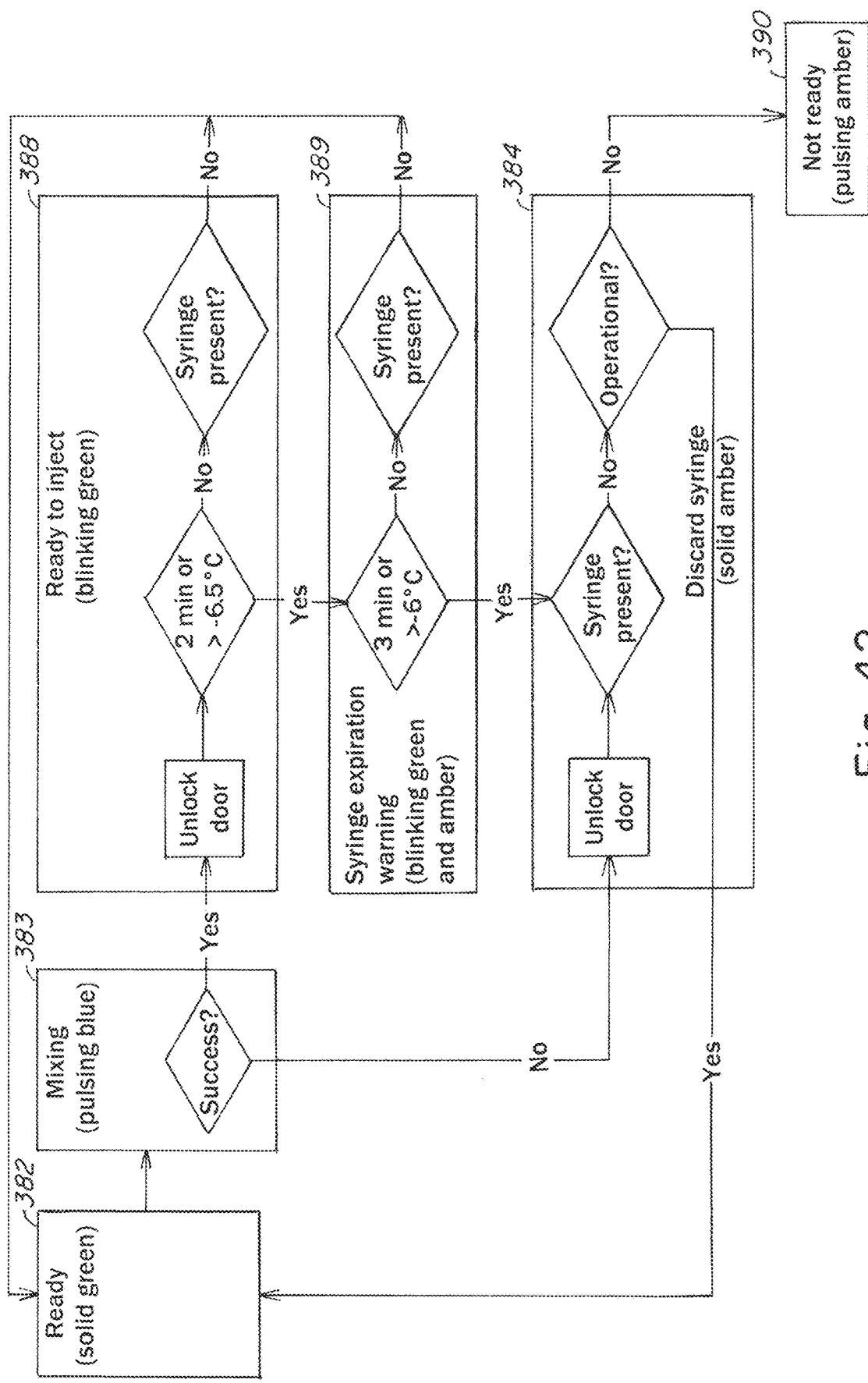
FIG. 42 is an operational flow diagram showing device operational steps after mixing/blending operation success and after mixing/blending operation failure and corresponding LED light status.

Referring to FIG. 42, once the system is in a ready state at step 382 and no further operational issues are detected (see FIG. 40 and corresponding description), the operational flow moves to step 383 (as in FIG. 38) during which the mixing or blending operation takes place and the LED light pulses blue (see FIG. 41 and corresponding description). If it is determined at step 383 that the mixing/blending operation was a failure/not successful, the operational flow moves to step 384 (e.g., see FIG. 38) during which the LED light turns to a solid amber color indicating to the user that the syringe should be discarded, and the syringe contents should not be injected into a patient. Additionally, the system sends a signal to the device to unlock the safety door. At the same time, at step 384, the system is continuously/periodically monitoring whether the syringe is still present (e.g., docked). As long as the syringe is still present, the operational flow will remain at step 384, the LED light will continue to display a solid amber color, and the system will monitor continuously or periodically if the syringe is still present. If it is determined that the syringe is no longer present (e.g., a user has removed the syringe for injection into a patient), the system queries whether the device is operational (e.g., see step 384 at FIG. 38). If it is determined that the device is not operational, the operational flow moves to step 390 (e.g., see FIG. 39) during which the LED light pulses in an amber color indicating to the user that the device is not ready to accept a syringe and the blending or mixing operation cannot be initiated. If it is determined at step 384 that the device is operational, the operational flow moves back to step 382 during which the LED light turns to a solid green color indicating to the user that the device is in a ready state and the user may now place a syringe into the device and initiate the mixing or blending operation at step 383.

If it is determined at step 383 that the mixing operation was a success, the system sends a signal to the device to unlock the safety door (in embodiments with a safety door, e.g., see FIGS. 8 and 9) and the LED light blinks with a green color to indicate to a user that the syringe is ready for injection of a cold slurry into a patient at a target location. At the same time, the system moves to operational step 388 during which the system is continuously or periodically monitoring whether the syringe is still present (e.g., docked). If it is determined that the syringe is no longer present (e.g., a user has removed the syringe for injection into a patient), the operational flow moves back to the ready state at step 382 and the LED light turns to a solid green to indicate to a user that a new syringe is ready to be placed in the device for mixing or blending. Alternatively, if the syringe is determined to be present at step 388, the system continuously or periodically monitors the time that has elapsed since the ready to inject state (LED blinking green) has been achieved, and also continuously or periodically monitors the syringe temperature (e.g., using an IR sensor on the device). The system continuously or periodically checks whether the syringe is still present and as long as it is still present, the system will continue to periodically/continuously monitor the elapsed time and syringe temperature. If it is determined at step 388 that a predetermined amount of time has elapsed and the syringe is still present (e.g., less than about 1 minute, between 1 minute and 2 minutes, between 2 minutes and 3 minutes, or more than about 3 minutes), the operational flow moves to step 389. Likewise, if it is determined at step 388 that the slurry inside the syringe (e.g., using an IR sensor on the device) has warmed up to a predetermined temperature threshold (e.g., warmer than about −7° C., warmer than about −6.5° C., warmer than about −6° C., warmer than about −5.5° C., or warmer than about −5° C.), the operational flow moves to step 389.

At step 389, the LED light blinks with alternating green and amber colors indicating to the user as a warning that syringe expiration is approaching (e.g., because the syringe has been sitting in the docking station for too long following blending and/or the slurry temperature is too warm). During step 389, the system continuously or periodically checks whether the syringe is still present and as long as it is still present, the system will continue to periodically or continuously monitor the elapsed time and syringe temperature as previously described for step 388. If it is determined at step 389 that the syringe is no longer present (e.g., a user has removed the syringe for injection into a patient), the operational flow moves back to the ready state at step 382 and the LED light turns to a solid green to indicate to a user that a new syringe is ready to be placed in the device for mixing or blending. Alternatively, if it is determined at step 389 that a predetermined amount of time has elapsed and the syringe is still present (e.g., less than about 1 minute, between 1 minute and 2 minutes, between 2 minutes and 3 minutes, or more than about 3 minutes), the operational flow moves to step 384. Likewise, if it is determined at step 389 that the slurry inside the syringe (e.g., using an IR sensor on the device) has warmed up to a predetermined temperature threshold (e.g., warmer than about −7° C., warmer than about −6.5° C., warmer than about −6° C., warmer than about −5.5° C., or warmer than about −5° C.), the operational flow moves to step 384.

At step 384, the LED light turns to a sold amber color (also see FIG. 38) indicating to the user that the syringe should be discarded, and the syringe contents should not be injected into a patient. Additionally, at step 384, the system monitors continuously/periodically if the syringe is still present in the device. As long as the syringe is still present, the operational flow will remain at step 384, the LED light will continue to display a solid amber color, and the system will monitor continuously or periodically if the syringe is still present. If it is determined that the syringe is no longer present (e.g., a user has removed the syringe for injection into a patient), the system queries whether the device is operational (e.g., see step 384 at FIG. 38). If it is determined that the device is not operational, the operational flow moves to step 390 (e.g., see FIG. 39) during which the LED light pulses in an amber color indicating to the user that the device is not ready to accept a syringe and the blending or mixing operation cannot be initiated. If it is determined at step 384 that the device is operational, the operational flow moves back to step 382 during which the LED light turns to a solid green color indicating to the user that the device is in a ready state, the user may now place a syringe into the device to initiate the mixing/blending operation at step 383, and the operational flow proceeds from step 383 to other operational flow steps as previously described herein.

The systems, devices, apparatuses, and methods of the present disclosure may be used in the following ways. A user may receive a sterilized syringe at a point of care that has been prefilled with components such those shown and described in FIG. 2, the prefilled composition being configured to allow the internal volume of the syringe to form into an injectable and flowable cold slurry based on the freezing point of the composition (e.g., FIG. 1). The syringe can be stored by any means known in the art at the point of care until the user needs to prepare the injectable and flowable cold slurry. When a user is ready to begin preparing an injectable and flowable cold slurry, the user can place the syringe into a freezer to cause an internal volume of the syringe to at least partially crystallize. In some embodiments, the docking station described herein (e.g., see docking stations 403, 803, 2000, or 3000 in FIGS. 4-14, 16-17, 20-23, 30-33, and 36) can include one or more refrigeration elements that when activated would expose the syringe to freezing temperatures for a set period of time to cause at least partial crystallization of the syringe contents. Once the slurry has been exposed to freezing temperatures, e.g., less than about 0° C., less than about −5° C., less than about −10° C., or less than about −15° C., the syringe can be place in the docking station (or maintained in the docking station if the docking station has refrigeration elements) and the contents of the syringe can be blended or mixed using any of the embodiments disclosed herein (e.g., see FIGS. 4-18, 20-23, 25-33, and 35-36). After the syringe contents have been blended or mixed, an injectable and flowable cold slurry is formed and is ready for injection into a patient. The user can remove the syringe from the docking station and, if necessary, attach a needle to the syringe. The user can then inject the cold slurry into a target location in a subject or patient (e.g., FIGS. 19, 24, 34, and 37). Throughout this process, the user does not need to measure, determine, or modify the contents of the syringe. In some embodiments, the user does not need to take any extra steps to maintain sterility of the syringe contents.

Although a syringe is used in the examples described herein, any container known in the art may be used in place of a syringe. Suitable containers other than a syringe include a vial, a bag, or a plastic or glass vessel. The container is configured to interact with the apparatuses, devices, and systems of the present invention to transform an internal volume of the container into an injectable and flowable cold slurry.

The injectable slurry described herein can be utilized to target all tissue types including, but not limited to, connective, epithelial, neural, joint, cardiac, adipose, hepatic, renal, vascular, cutaneous, and muscle tissues. The injectable slurry advantageously can focus a cooling effect directly at the site of the targeted tissue through injection directly into interstitial tissue, without the challenges of diffusion of heat or perfusion tissue, as described in U.S. Application No. 2017/0274011 and incorporated in its entirety herein. As described in U.S. Application No. 2017/0274078 and incorporated in its entirety herein, the injectable slurry can be used as a treatment for pain. Injection/infusion of the slurry near nerves causes crystallization of lipids in the myelin sheath, or direct cooling of non-myelinated nerves, thereby resulting in a site-specific relief of pain through inhibition of nerve conduction. The inhibition of peripheral nerve conduction is reversible (e.g., inhibition can occur for a period of minutes, days, weeks or months after a single administration of the slurry) (see U.S. Application No. 2017/0274078). In addition to pain relief applications, the injectable slurry can also be administered to target parts of the somatic and/or autonomic nervous system to treat a variety of conditions (e.g., inhibition of motor nerves to reduce muscle spasms, inhibition of sympathetic fibers that innervate the eccrine glands to reduce hyperhidrosis, inhibition of renal sympathetic nerves as a treatment for hypertension, and inhibition of neural input to the bladder to treat incontinence) (see U.S. Application No. 2017/0274078).

The devices, systems, and methods disclosed herein are not to be limited in scope to the specific embodiments described herein. Indeed, various modifications of the devices, systems, and methods in addition to those described will become apparent to those of skill in the art from the foregoing description and accompanying figures. Such modifications are intended to fall within the scope of the appended claims.

The invention claimed is:

1. A system for creating an injectable and flowable cold slurry, the system comprising:
   a syringe comprising a blade shaft;
   a housing;
   a mount operatively connected to the housing configured to accept the syringe;
   a first motor configured to move the mount from a first position to a second position;
   a second motor; and
   a drive shaft in communication with the second motor, wherein the drive shaft is configured to rotate to cause an internal volume of the syringe to be transformed into the injectable and flowable cold slurry.

2. The system of claim 1, wherein the blade shaft comprises a plurality of blades.

3. The system of claim 1, wherein the blade shaft is configured to engage with the drive shaft, and wherein the blade shaft is configured to rotate to cause the internal volume of the syringe to be transformed into the injectable and flowable cold slurry.

4. The system of claim 1, further comprising one or more rails, wherein the mount is configured to move along the one or more rails from the first position to the second position.

5. The system of claim 1, wherein the first motor is selected from a brushless DC motor or a linear actuator.

6. The system of claim 1, wherein the second motor is selected from a brushless DC motor or a spindle motor.

7. The system of claim 1, further comprising a pulley in communication with the second motor, wherein the pulley is configured to rotate the drive shaft.

8. The system of claim 1, further comprising one or more pulleys in communication with the first motor, wherein the one or more pulleys are configured to move the mount from the first position to the second position.

9. The system of claim 1, wherein the first motor is configured to move the mount from the first position to the second position along a longitudinal axis.

10. The system of claim 1, further comprising a worm and a worm gear, wherein the worm is in communication with the worm gear, and wherein the worm gear is configured to rotate a pulley to move the mount from the first position to the second position.

11. A system for creating an injectable and flowable cold slurry, the system comprising:
   a sled configured to accept a syringe;
   a first motor configured to move the sled from a first position to a second position;
   a second motor;
   a drive shaft in communication with the second motor; and
   a pulley in communication with the second motor and the drive shaft, wherein the drive shaft is configured to rotate to cause an internal volume of the syringe to be transformed into the injectable and flowable cold slurry.

12. The system of claim 11, further comprising the syringe, wherein the syringe comprises a blade shaft.

13. The system of claim 12, wherein the blade shaft comprises a plurality of blades.

14. The system of claim 12, wherein the syringe further comprises a plunger, wherein the plunger comprises a hollow portion, and wherein the blade shaft is configured to retract into the hollow portion of the plunger.

15. The system of claim 11, further comprising one or more rails, wherein the one of more rails are configured to move the sled from the first position to the second position.

16. The system of claim 11, wherein the first motor is selected from a brushless DC motor or a linear actuator.

17. The system of claim 11, wherein the second motor is selected from a brushless DC motor or a spindle motor.

18. The system of claim 11, further comprising one or more pulleys in communication with the first motor, wherein the one or more pulleys are configured to move the sled from the first position to the second position.

19. The system of claim 11, further comprising a safety door.

20. An apparatus for creating an injectable and flowable cold slurry, the apparatus comprising:
   a sled configured to accept a syringe;
   a first motor configured to move the sled from a first position to a second position;
   a drive shaft; and
   a second motor configured to cause rotation of the drive shaft, wherein the rotation of the drive shaft causes an internal volume of the syringe to be formed into the injectable and flowable cold slurry.

21. The apparatus of claim 20, wherein the sled further comprises a dock, wherein the dock is configured to accept the syringe.

22. The apparatus of claim 20, wherein the sled comprises a front holder mount and a back holder mount, and wherein the front holder mount is configured to be moved to an open position to accept the syringe.

23. The apparatus of claim 20, further comprising one or more pulleys in communication with the first motor, wherein the one or more pulleys are configured to move the sled from the first position to the second position.

24. An apparatus for transforming an internal volume of a syringe into an injectable and flowable cold slurry, the apparatus comprising:
   the syringe comprising a blade shaft, wherein the blade shaft comprises a first bayonet connector configured to engage with a second bayonet connector,
   a mount configured to accept the syringe;
   a drive shaft, wherein the drive shaft comprises the second bayonet connector;
   a first motor in communication with the drive shaft, wherein the first motor is configured to rotate the drive shaft to transform the internal volume of the syringe into the injectable and flowable cold slurry; and
   a second motor configured to move the mount from a first position to a second position.

25. The apparatus of claim 24, further comprising one or more pulleys in communication with the second motor, wherein the one or more pulleys are configured to move the mount from the first position to the second position.

26. The apparatus of claim 24, further comprising one or more rails, wherein the mount is configured to move along the one or more rails from the first position to the second position.

* * * * *